US012742169B2

(12) United States Patent
Wu et al.

(10) Patent No.: US 12,742,169 B2
(45) Date of Patent: Sep. 22, 2026

(54) RNAi CONSTRUCTS AND METHODS FOR INHIBITING LPA EXPRESSION

(71) Applicant: AMGEN INC., Thousand Oaks, CA (US)

(72) Inventors: Bin Wu, Thousand Oaks, CA (US); Michael Ollmann, San Carlos, CA (US); Oliver Homann, Berkeley, CA (US); Yuan Cheng, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 970 days.

(21) Appl. No.: 17/783,232

(22) PCT Filed: Dec. 8, 2020

(86) PCT No.: PCT/US2020/063844

§ 371 (c)(1),
(2) Date: Jun. 7, 2022

(87) PCT Pub. No.: WO2021/119034

PCT Pub. Date: Jun. 17, 2021

(65) Prior Publication Data

US 2023/0078200 A1 Mar. 16, 2023

Related U.S. Application Data

(60) Provisional application No. 62/945,777, filed on Dec. 9, 2019.

(51) Int. Cl.
*C12N 15/113* (2010.01)
*A61P 9/10* (2006.01)

(52) U.S. Cl.
CPC .............. *C12N 15/113* (2013.01); *A61P 9/10* (2018.01); *C12N 2310/14* (2013.01); *C12N 2310/315* (2013.01); *C12N 2310/321* (2013.01); *C12N 2310/322* (2013.01); *C12N 2310/346* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,877,022 | A | 3/1999 | Stinchcomb |
| 5,885,968 | A | 3/1999 | Biessen |
| 7,741,305 | B2 | 6/2010 | Crooke |
| 8,084,599 | B2 | 12/2011 | Rossi |
| 8,349,809 | B2 | 1/2013 | Brown |
| 8,513,207 | B2 | 8/2013 | Brown |
| 9,023,820 | B2 | 5/2015 | Macdonald |
| 9,932,586 | B2 | 4/2018 | Melquist |
| 10,662,427 | B2 | 5/2020 | Melquist |
| 2004/0259248 | A1 | 12/2004 | Tuschl |
| 2008/0108801 | A1 | 5/2008 | Manoharan |
| 2008/0281044 | A1 | 11/2008 | Monahan |
| 2008/0281074 | A1 | 11/2008 | Rozema |
| 2009/0131360 | A1 | 5/2009 | Woolf |
| 2009/0264636 | A1 | 10/2009 | Vargeese |
| 2010/0015218 | A1 | 1/2010 | Jadhav |
| 2010/0144831 | A1 | 6/2010 | Fakhral |
| 2011/0039910 | A1 | 2/2011 | Crooke |
| 2011/0207799 | A1 | 8/2011 | Rozema |
| 2012/0157509 | A1 | 6/2012 | Hadwiger |
| 2012/0230938 | A1 | 9/2012 | Rozema et al. |
| 2014/0045922 | A1 | 2/2014 | Soutschek |
| 2015/0045573 | A1 | 2/2015 | Cheng et al. |
| 2015/0126720 | A1 | 5/2015 | Prakash |
| 2016/0102120 | A1 | 4/2016 | Hadwiger |
| 2016/0272970 | A1 | 9/2016 | Rozema |
| 2017/0029817 | A1 | 2/2017 | Zimmermann |
| 2017/0253875 | A1 | 9/2017 | Rozema |
| 2022/0049252 | A1 * | 2/2022 | Murray ................ C12N 15/111 |

FOREIGN PATENT DOCUMENTS

| | | | |
|---|---|---|---|
| CN | 103547272 | A | 1/2014 |
| CN | 104411338 | A | 3/2015 |
| CN | 104080794 | A | 3/2018 |
| CO | 16113531 | A2 | 12/2006 |
| CO | 7540374 | A2 | 3/2016 |
| CO | 16108382 | A2 | 9/2016 |
| JP | 2011155914 | A | 8/2011 |
| JP | 2014504295 | A | 2/2014 |
| JP | 2015522255 | A | 8/2015 |
| WO | 199609392 | A1 | 3/1996 |
| WO | 2000053722 | A2 | 9/2000 |
| WO | 2003014307 | A2 | 2/2003 |

(Continued)

OTHER PUBLICATIONS

Kliuchnikov et al. Molecular Therapy:Nucleic Acids vol. 36, pp. 1-14 (Year: 2025).*

Dar et al. Sci. Rep. 6:20031 pp. 1-8 (Year: 2016).*

Hean et al., "Inhibition of heptatis B virus replication in vivo using lipoplexes containing altritol-modified antiviral SiRNAs," Artificial DNA: PNA & XNA, vol. 1(1), pp. 17-26 (2010).

Pascut et al., "Silencing efficacy prediction: a retrospective study on target mRNA features," Bioscience Reports, vol. 35, e00185, 8 pages (2015).

Wolfrum et al., "Mechanisms and optimization of in vivo delivery of lipophilic siRNAs," Nature Biotechnology, vol. 25, No. 10, pp. 1149-1157 (2007).

Xue et al., "Lipid-Based Nanocarriers for RNA Delivery", Current Pharmaceutical Design, vol. 21, pp. 3140-3147 (2015).

Baenziger and Fiete, "Galactose and N-Acetylgalactosamine-Specific Endocytosis of Glycopeptides by Isolated Rat Hepatocytes", Cell, vol. 22, pp. 611-620 (1980).

(Continued)

*Primary Examiner* — Brian Whiteman
(74) *Attorney, Agent, or Firm* — Angela L. Purcell

(57) ABSTRACT

The present invention relates to RNAi constructs for reducing expression of the LPA gene, which encodes apolipoprotein(a), a component of lipoprotein(a) (Lp(a)) particles. Methods of using such RNAi constructs to treat or prevent cardiovascular disease, such as coronary artery disease, peripheral artery disease, stroke, and myocardial infarction, and to reduce serum Lp(a) levels are also described.

36 Claims, 6 Drawing Sheets

Specification includes a Sequence Listing.

(56) References Cited

FOREIGN PATENT DOCUMENTS

| | | | |
|---|---|---|---|
| WO | 2004081198 | A2 | 9/2004 |
| WO | 2005000201 | A2 | 1/2005 |
| WO | 2008022309 | A2 | 2/2008 |
| WO | 2009126933 | A2 | 10/2009 |
| WO | 2011029016 | A1 | 3/2011 |
| WO | 2011104169 | A1 | 9/2011 |
| WO | 2011141703 | A1 | 11/2011 |
| WO | 2012083046 | A2 | 6/2012 |
| WO | 2012083185 | A2 | 6/2012 |
| WO | 2012092373 | A2 | 7/2012 |
| WO | 2013032829 | A1 | 3/2013 |
| WO | 2013075035 | A1 | 5/2013 |
| WO | 2013151666 | A2 | 10/2013 |
| WO | 2013158141 | A1 | 10/2013 |
| WO | 2013177468 | A2 | 11/2013 |
| WO | 2014134483 | A2 | 9/2014 |
| WO | 2014160129 | A2 | 10/2014 |
| WO | 2014179625 | A1 | 11/2014 |
| WO | 2014182661 | A2 | 11/2014 |
| WO | 2014205451 | A2 | 12/2014 |
| WO | 2015050990 | A1 | 4/2015 |
| WO | 2015051318 | A1 | 4/2015 |
| WO | 2016149020 | A1 | 9/2016 |
| WO | 2016196239 | A1 | 12/2016 |
| WO | 2017059223 | A2 | 4/2017 |
| WO | 2019092283 | A1 | 5/2019 |
| WO | 2019118638 | A2 | 6/2019 |
| WO | 2020099476 | A1 | 5/2020 |
| WO | 2022032288 | A1 | 2/2022 |
| WO | 2022079221 | A1 | 4/2022 |

OTHER PUBLICATIONS

Biessen et al., "Synthesis of Cluster Galactosides with High Affinity for the Hepatic Asialoglycoprotein Receptor", J. Med. Chem., vol. 38 (9), pp. 1538-1546 (1995).
Callow et al., "Expression of human apolipoprotein B and assembly of lipoprotein(a) in transgenic mice", Proc. Natl. Acad. Sci. USA, vol. 91, pp. 2130-2134 (1994).
Chinese Office Action 201680057095.8 dated Jan. 15, 2021 (English Translation).
Connolly et al., "Binding and Endocytosis of Cluster Glycosides by Rabbit Hepatocytes", J. Biol. Chem., vol. 257 (2), pp. 939-945 (1982).
Frazer et al., "The apolipoprotein(a) gene is regulated by sex hormones and acute-phase inducers in YAC transgenic mice", Nature Gen., vol. 9, pp. 424-431 (1995).
Haussecker, D., "Current Issues of RNAi Therapeutics Delivery and Development", J. Controlled Release, vol. 195, pp. 49-54 (2014).
Huang and Cai, "Asialoglycoprotein Receptor and Its Application in Live-targeted Drug Delivery", Prog. Biochem. Biophys., vol. 42 (6), pp. 501-510 (2015).
Integrated DNA Technologies, Inc., "Dicer Substrate RNAi Design", pp. 1-6 (2005).
International Search Report and Written Opinion for PCT/US16/54729 dated Mar. 20, 2017.
Iobst and Drickamer, "Selective Sugar Binding to the Carbohydrate Recognition Domains of the Rat Hepatic and Macrophage Asialoglycoprotein Receptors", J. Biol. Chem., vol. 271 (12), pp. 6686-6693 (1996).
Koren et al., "Preclinical development and phase 1 trial of a novel siRNA targeting lipoprotein(a)", Nature Medicine, vol. 28, pp. 96-103 (2022).
Kurt et al., "Lipoprotein(a): clinical aspects and future challenges", Clin. Res. Cardiol. Suppl., Vol. (Suppl.) 10, pp. 26-32 (2015).
Merki et al., "Antisense Oligonucleotide Lowers Plasma Levels of Apolipoprotein (a) and Lipoprotein (a) in Transgenic Mice", J. Amer. College Cardiol., vol. 57 (15), pp. 1611-1621 (2011).
Miles et al., "Genome-wide screen for modulation of hepatic apolipoprotein A-I (ApoA-I) secretion", J. Biol. Chem., vol. 288 (9), pp. 6386-6396 (2013).
Nair et al., "Multivalent N-Acetylgalactosamine-Conjugated siRNA Localizes in Hepatocytes and Elicits Robust RNAi-Mediate Gene Silencing," J. Am. Chem. Soc., 2014, 136, 16958-16961.
NCBI, "*Homo sapiens* lipoprotein(a) (LPA), mRNA", NM_005577.2 (May 28, 2017).
NCBI, "*Homo sapiens* lipoprotein, Lp(a), (LPA), mRNA", NM_005577.1 (Sep. 19, 2006).
Partial Supplemental Search Report from European Application No. 16852695 dated Apr. 23, 2019.
Setten et al., "The current state and future directions of RNAi-based therapeutics," Nature Reviews Drug Discovery, vol. 18, pp. 421-446 (2019).
Tadin-Strapps et al., "Development of Lipoprotein(a) siRNAs for Mechanism of Action Studies in Non-Human Primate Models of Atherosclerosis", J. Cardiovasc. Trans. Res., vol. 8, pp. 44-53 (2015).
Tadin-Strapps et al., "siRNA-induced liver ApoB knockdown lowers serum LDL-cholesterol in a mouse model with human-like serum lipids", J. Lipid Res., vol. 52, pp. 1084-1097 (2011).
Tomita et al., "631. Novel Therapeutic Approach Using siRNA to Reduce Plasma High Concentration of Lp(a)", Molec. Therapy: J. Amer. Soc. Gene Therapy, vol. 11, pp. 245 (2005).
Written Opinion and International Search Report for Appln. No. PCT/US2020/063844 mailed May 21, 2021.
International Preliminary Report on Patentability for PCT/US2016/054729 dated Dec. 11, 2017.
O'Donoghue et al., "Small Interfering RNA to Reduce Lipoprotein (a) in Cardiovascular Disease", New England Journal of Medicine, vol. 387, pp. 1855-1864 (2022).

* cited by examiner

FIG. 1

```
1     gtaagtcaac aatgtcctgg gattgggaca cactttctgg gcactgctgg ccagtcccaa aatggaacat aaggaagtgg ttcttctact
91    tcttttattt ctgaaatcag cagcacctga gcaaagccat gtggtccagg attgctacca tggtgatgga cagagttatc gaggcacgta
181   ctccaccact gtcacaggaa ggacctgcca agcttggtca tctatgacac cacatcaaca taataggacc acagaaaact acccaaatgc
271   tggcttgatc atgaactact gcaggaatcc agatgctgtg gcagctcctt attgttatac gagggatccc ggtgtcaggt gggagtactg
361   caacctgacg caatgctcag acgcagaagg gactgccgtc gcgcctccga ctgttacccc ggttccaagc ctagaggctc cttccgaaca
451   agcaccgact gagcaaaggc ctggggtgca ggagtgctac catggtaatg gacagagtta tcgaggcaca tactccacca ctgtcacagg
541   aagaacctgc caagcttggt catctatgac accacactcg catagtcgga ccccagaata ctacccaaat gctggcttga tcatgaacta
631   ctgcaggaat ccagatgctg tggcagctcc ttattgttat acgagggatc ccggtgtcag gtgggagtac tgcaacctga cgcaatgctc
721   agacgcagaa gggactgccg tcgcgcctcc gactgttacc ccggttccaa gcctagaggc tccttccgaa caagcaccga ctgagcaaag
811   gcctggggtg caggagtgct accatggtaa tggacagagt tatcgaggca catactccac cactgtcaca ggaagaacct gccaagcttg
901   gtcatctatg acaccacact cgcatagtcg gaccccagaa tactacccaa atgctggctt gatcatgaac tactgcagga atccagatgc
991   tgtggcagct ccttattgtt atacgaggga tcccggtgtc aggtgggagt actgcaacct gacgcaatgc tcagacgcag aagggactgc
1081  cgtcgcgcct ccgactgtta ccccggttcc aagcctagag gctccttccg aacaagcacc gactgagcag aggcctgggg tgcaggagtg
1171  ctaccacggt aatggacaga gttatcgagg cacatactcc accactgtca ctggaagaac ctgccaagct tggtcatcta tgacaccaca
1261  ctcgcatagt cggaccccag aatactaccc aaatgctggc ttgatcatga actactgcag gaatccagat gctgtggcag ctccttattg
1351  ttatacgagg gatcccggtg tcaggtggga gtactgcaac ctgacgcaat gctcagacgc agaagggact gccgtcgcgc ctccgactgt
1441  taccccggtt ccaagcctag aggctccttc cgaacaagca ccgactgagc aaaggcctgg ggtgcaggag tgctaccatg gtaatggaca
1531  gagttatcga ggcacatact ccaccactgt cacaggaaga acctgccaag cttggtcatc tatgacacca cactcgcata gtcggacccc
1621  agaatactac ccaaatgctg gcttgatcat gaactactgc aggaatccag atgctgtggc agctccttat tgttatacga gggatcccgg
1711  tgtcaggtgg gagtactgca acctgacgca atgctcagac gcagaaggga ctgccgtcgc gcctccgact gttaccccgg ttccaagcct
1801  agaggctcct tccgaacaag caccgactga gcaaaggcct ggggtgcagg agtgctacca tggtaatgga cagagttatc gaggcacata
1891  ctccaccact gtcacaggaa gaacctgcca agcttggtca tctatgacac cacactcgca tagtcggacc ccagaatact acccaaatgc
```

FIG. 1 (cont.)

```
1981  tggcttgatc atgaactact gcaggaatcc agatgctgtg gcagctcctt attgttatac gagggatccc ggtgtcaggt gggagtactg
2071  caacctgacg caatgctcag acgcagaagg gactgccgtc gcgcctccga ctgttacccc ggttccaagc ctagaggctc cttccgaaca
2161  agcaccgact gagcaaaggc ctggggtgca ggagtgctac catggtaatg gacagagtta tcgaggcaca tactccacca ctgtcacagg
2251  aagaacctgc caagcttggt catctatgac accacactcg catagtcgga ccccagaata ctacccaaat gctggcttga tcatgaacta
2341  ctgcaggaat ccagatgctg tggcagctcc ttattgttat acgagggatc ccggtgtcag gtgggagtac tgcaacctga cgcaatgctc
2431  agacgcagaa gggactgccg tcgcgcctcc gactgttacc ccggttccaa gcctagaggc tccttccgaa caagcaccga ctgagcagag
2521  gcctggggtg caggagtgct accacggtaa tggacagagt tatcgaggca catactccac cactgtcact ggaagaacct gccaagcttg
2611  gtcatctatg acaccacact cgcatagtcg gaccccagaa tactacccaa atgctggctt gatcatgaac tactgcagga atccagatcc
2701  tgtggcagcc ccttattgtt atacgaggga tcccagtgtc aggtgggagt actgcaacct gacacaatgc tcagacgcag aagggactgc
2791  cgtcgcgcct ccaactatta ccccgattcc aagcctagag gctccttctg aacaagcacc aactgagcaa aggcctgggg tgcaggagtg
2881  ctaccacgga aatggacaga gttatcaagg cacatacttc attactgtca caggaagaac ctgccaagct tggtcatcta tgacaccaca
2971  ctcgcatagt cggaccccag catactaccc aaatgctggc ttgatcaaga actactgccg aaatccagat cctgtggcag ccccttggtg
3061  ttatacaaca gatcccagtg tcaggtggga gtactgcaac ctgacacgat gctcagatgc agaatggact gccttcgtcc ctccgaatgt
3151  tattctggct ccaagcctag aggctttttt tgaacaagca ctgactgagg aaaccccccgg ggtacaggac tgctactacc attatggaca
3241  gagttaccga ggcacatact ccaccactgt cacaggaaga acttgccaag cttggtcatc tatgacacca caccagcata gtcggacccc
3331  agaaaactac ccaaatgctg gcctgaccag gaactactgc aggaatccag atgctgagat tcgcccttgg tgttacacca tggatcccag
3421  tgtcaggtgg gagtactgca acctgacaca atgcctggtg acagaatcaa gtgtccttgc aactctcacg gtggtcccag atccaagcac
3511  agaggcttct tctgaagaag caccaacgga gcaaagcccc ggggtccagg attgctacca tggtgatgga cagagttatc gaggctcatt
3601  ctctaccact gtcacaggaa ggacatgtca gtcttggtcc tctatgacac cacactggca tcagaggaca acagaatatt atccaaatgg
3691  tggcctgacc aggaactact gcaggaatcc agatgctgag attagtcctt ggtgttatac catggatccc aatgtcagat gggagtactg
3781  caacctgaca caatgtccag tgacagaatc aagtgtcctt gcgacgtcca cggctgtttc tgaacaagca ccaacggagc aaagccccac
3871  agtccaggac tgctaccatg gtgatggaca gagttatcga ggctcattct ccaccactgt tacaggaagg acatgtcagt cttggtcctc
```

FIG. 1 (cont.)

```
3961  tatgacacca cactggcatc agagaaccac agaatactac ccaaatggtg gcctgaccag gaactactgc aggaatccag atgctgagat
4051  tcgcccttgg tgttatacca tggatcccag tgtcagatgg gagtactgca acctgacgca atgtccagtg atggaatcaa ctctcctcac
4141  aactcccacg gtggtcccag ttccaagcac agagcttcct tctgaagaag caccaactga aaacagcact ggggtccagg actgctaccg
4231  aggtgatgga cagagttatc gaggcacact ctccaccact atcacaggaa gaacatgtca gtcttggtcg tctatgacac cacattggca
4321  tcggaggatc ccattatact atccaaatgc tggcctgacc aggaactact gcaggaatcc agatgctgag attcgccctt ggtgttacac
4411  catggatccc agtgtcaggt gggagtactg caacctgaca cgatgtccag tgacagaatc gagtgtcctc acaactccca cagtggcccc
4501  ggttccaagc acagaggctc cttctgaaca agcaccacct gagaaaagcc ctgtggtcca ggattgctac catggtgatg gacggagtta
4591  tcgaggcata tcctccacca ctgtcacagg aaggacctgt caatcttggt catctatgat accacactgg catcagagga ccccagaaaa
4681  ctacccaaat gctggcctga ccgagaacta ctgcaggaat ccagattctg ggaaacaacc ctggtgttac acaaccgatc cgtgtgtgag
4771  gtgggagtac tgcaatctga cacaatgctc agaaacagaa tcaggtgtcc tagagactcc cactgttgtt ccagttccaa gcatggaggc
4861  tcattctgaa gcagcaccaa ctgagcaaac ccctgtggtc cggcagtgct accatggtaa tggccagagt tatcgaggca cattctccac
4951  cactgtcaca ggaaggacat gtcaatcttg gtcatccatg acaccacacc ggcatcagag gaccccagaa aactacccaa atgatggcct
5041  gacaatgaac tactgcagga atccagatgc cgatacaggc ccttggtgtt ttaccatgga ccccagcatc aggtgggagt actgcaacct
5131  gacgcgatgc tcagacacag aagggactgt ggtcgctcct ccgactgtca tccaggttcc aagcctaggg cctccttctg aacaagactg
5221  tatgtttggg aatgggaaag gataccgggg caagaaggca accactgtta ctgggacgcc atgccaggaa tgggctgccc aggagcccca
5311  tagacacagc acgttcattc cagggacaaa taaatgggca ggtctggaaa aaaattactg ccgtaaccct gatggtgaca tcaatggtcc
5401  ctggtgctac acaatgaatc caagaaaact ttttgactac tgtgatatcc ctctctgtgc atcctcttca tttgattgtg ggaagcctca
5491  agtggagccg aagaaatgtc ctggaagcat tgtagggggg tgtgtggccc acccacattc ctggccctgg caagtcagtc tcagaacaag
5581  gtttggaaag cacttctgtg gaggcacctt aatatcccca gagtgggtgc tgactgctgc tcactgcttg aagaagtcct caaggccttc
5671  atcctacaag gtcatcctgg gtgcacacca agaagtgaac ctcgaatctc atgttcagga aatagaagtg tctaggctgt tcttggagcc
5761  cacacaagca gatattgcct tgctaaagct aagcaggcct gccgtcatca ctgacaaagt aatgccagct tgtctgccat ccccagacta
5851  catggtcacc gccaggactg aatgttacat cactggctgg ggagaaaccc aaggtacctt tgggactggc cttctcaagg aagcccagct
```

FIG. 1 (cont.)

```
5941  ccttgttatt gagaatgaag tgtgcaatca ctataagtat atttgtgctg agcatttggc cagaggcact gacagttgcc agggtgacag
6031  tggagggcct ctggtttgct tcgagaagga caaatacatt ttacaaggag tcacttcttg gggtcttggc tgtgcacgcc ccaataagcc
6121  tggtgtctat gctcgtgttt caaggtttgt tacttggatt gagggaatga tgagaaataa ttaattggac gggagacaga gtgaagcatc
6211  aacctactta gaagctgaaa cgtgggtaag gatttagcat gctggaaata atagacagca atcaaacgaa gacactgttc ccagctacca
6301  gctatgccaa accttggcat ttttggtatt tttgtgtata agcttttaag gtctgactga caaattctgt attaaggtgt catagctatg
6391  acatttgtta aaaataaact ctgcacttat tttgatttga a  (SEQ ID NO: 1)
```

RNAi CONSTRUCTS AND METHODS FOR INHIBITING LPA EXPRESSION

CROSS-REFERENCE TO RELATED APPLICATIONS

This application claims the benefit of U.S. Provisional Application No. 62/945,777, filed Dec. 9, 2019, which is hereby incorporated by reference in its entirety.

DESCRIPTION OF THE TEXT FILE SUBMITTED ELECTRONICALLY

The present application contains a Sequence Listing, which has been submitted electronically in ASCII format and is hereby incorporated by reference in its entirety. The computer readable format copy of the Sequence Listing, which was created on Dec. 8, 2020, is named A-2425-WO-PCT_ST25 and is 190 kilobytes in size.

FIELD OF THE INVENTION

The present invention relates to compositions and methods for modulating liver expression of the LPA gene, which encodes apolipoprotein (a) (apo(a)). In particular, the present invention relates to nucleic acid-based therapeutics for reducing LPA gene expression via RNA interference and methods of using such nucleic acid-based therapeutics to reduce circulating levels of lipoprotein (a) (Lp(a)) and to treat or prevent cardiovascular disease.

BACKGROUND OF THE INVENTION

Lp(a) is a low-density lipoprotein consisting of an LDL particle and the glycoprotein apo(a), which is linked to the apolipoprotein B of the LDL particle by a disulfide bond. Apo(a) is encoded by the LPA gene and is expressed almost exclusively in primates, including humans. Apo(a) exhibits homology to plasminogen and is present in various isoforms due to a size polymorphism in the gene, which is caused by a variable number of kringle-IV, type 2 (KIV-2) domain repeats (see Kronenberg and Utermann, J. Intern. Med., Vol. 273:6-30, 2013). An inverse correlation has been observed between the size of the apo(a) isoform and the plasma levels of Lp(a) particles (Sandholzer et al., Hum. Genet., Vol. 86: 607-614, 1991).

The physiological function of Lp(a) is unclear, but Lp(a) has been shown to have a pathogenic role in atherosclerosis and thrombosis formation (Nordestgaard and Langsted, Lipid Res., Vol. 57:1953-75, 2016). The connection between Lp(a) levels and coronary artery disease, myocardial infarction, stroke, peripheral vascular disease, and aortic valve stenosis has been described in several genetic and observational studies (Schmidt et al., J. Lipid Res., Vol. 57:1339-1359, 2016). It has been noted that this risk relationship is continuous and becomes proportionally more impactful with higher Lp(a) levels. The association persists after correction for other lipid parameters (Emerging Risk Factors Collaboration, JAMA, Vol. 302:412-423, 2009).

High plasma Lp(a) concentration is genetically defined, remains at stable levels, cannot be controlled by habit modifications (diet, exercise, or other environmental factors), and is not effectively controlled by any of the currently available lipid reducing medications. Currently, there are no approved therapies indicated to reduce the risk of cardiovascular events through reductions in Lp(a). Moderate decreases in Lp(a) have been observed with proprotein convertase subtilisin/kexin type 9 (PCSK9) inhibitors, niacin, and mipomersen (Santos et al., Arterioscler. Thromb. Vasc. Biol., Vol. 35:689-699, 2015; Yeang et al., Curr. Opin. Lipidol., Vol. 26:169-178, 2015; and Landray et al., N. Engl. J. Med., Vol. 371:203-212, 2014). While apheresis is effective in lowering Lp(a), it is currently used only in a few countries with limited access (Julius, J. Cardiovasc. Dev. Dis., Vol. 5:27-37, 2018). In addition, it is an invasive, very expensive procedure requiring frequent visits, which makes it unfeasible as a long-term treatment for subjects who need lifelong therapy (Khan et al., Eur. Heart J., Vol. 38:1561-1569, 2017; Roeseler et al., Arterioscler. Thromb. Vasc. Biol., Vol. 36:2019-2027, 2016; Leebmann et al., Circulation, Vol. 128:2567-2576, 2013; Safarova et al., Atheroscler. Suppl., Vol. 14:93-99, 2013).

Accordingly, there is a need in the art for novel agents that potently lower high Lp(a) concentrations for prolonged durations to confer additional protection against cardiovascular disease.

SUMMARY OF THE INVENTION

The present invention is based, in part, on the design and generation of RNAi constructs that target the LPA gene and reduce expression of the encoded apo(a) protein in liver cells. The sequence-specific inhibition of LPA gene expression is useful for treating or preventing conditions associated with elevated Lp(a) levels, such as cardiovascular disease. Accordingly, in one embodiment, the present invention provides an RNAi construct comprising a sense strand and an antisense strand, wherein the antisense strand comprises a region having a sequence that is complementary to an LPA mRNA sequence. In certain embodiments, the antisense strand comprises or consists of a sequence selected from any of the antisense sequences listed in Table 1 or Table 2.

In some embodiments, the sense strand of the RNAi constructs described herein comprises a sequence that is sufficiently complementary to the sequence of the antisense strand to form a duplex region of about 15 to about 30 base pairs in length. In these and other embodiments, the sense and antisense strands are each independently about 19 to about 30 nucleotides in length. In some embodiments, the RNAi constructs comprise one or two blunt ends. In other embodiments, the RNAi constructs comprise one or two nucleotide overhangs. Such nucleotide overhangs may comprise 1 to 6 unpaired nucleotides and can be located at the 3' end of the sense strand, the 3' end of the antisense strand, or the 3' end of both the sense and antisense strand. In certain embodiments, the RNAi constructs comprise an overhang of two unpaired nucleotides at the 3' end of the sense strand and the 3' end of the antisense strand. In other embodiments, the RNAi constructs comprise an overhang of two unpaired nucleotides at the 3' end of the antisense strand and a blunt end at the 3' end of the sense strand/5' end of the antisense strand.

The RNAi constructs of the invention may comprise one or more modified nucleotides, including nucleotides having modifications to the ribose ring, nucleobase, or phosphodiester backbone. In some embodiments, the RNAi constructs comprise one or more 2'-modified nucleotides. Such 2'-modified nucleotides can include 2'-fluoro modified nucleotides, 2'-O-methyl modified nucleotides, 2'-O-methoxyethyl modified nucleotides, 2'-O-alkyl modified nucleotides, 2'-O-allyl modified nucleotides, bicyclic nucleic acids (BNA), deoxyribonucleotides, or combinations thereof. In one particular embodiment, the RNAi constructs comprise one or more 2'-fluoro modified nucleotides, 2'-O-methyl modified nucleotides, or combinations thereof. In some embodiments, all of the nucleotides in the sense and antisense strand of the RNAi construct are modified nucleotides. Abasic nucleotides may be incorporated into the RNAi constructs of the invention, for example, as the terminal nucleotide at the 3' end, the 5' end, or both the 3' end and the 5' end of the sense strand. In such embodiments, the abasic nucleotide may be inverted, e.g. linked to the adjacent nucleotide through a 3'-3' internucleotide linkage or a 5'-5' internucleotide linkage.

In some embodiments, the RNAi constructs comprise at least one backbone modification, such as a modified internucleotide or internucleoside linkage. In certain embodiments, the RNAi constructs described herein comprise at least one phosphorothioate internucleotide linkage. In particular embodiments, the phosphorothioate internucleotide linkages may be positioned at the 3' or 5' ends of the sense and/or antisense strands.

In certain embodiments, the antisense strand and/or the sense strand of the RNAi constructs of the invention may comprise or consist of a sequence from the antisense and sense sequences listed in Table 1 or Table 2. In certain embodiments, the RNAi construct may be any one of the duplex compounds listed in any one of Tables 1 to 15. In one embodiment, the RNAi construct is 4601, 4613, 4930, 4970, 6150, 6182, 6247, 8395, 8401, 10927, 11318, 11344, 11351, 11374, 11580, 17188, 17205, 18436, 18444, or 18446. In another embodiment, the RNAi construct is 4601, 4613, 10927, 11351, 11374, 11580, 18436, or 18444.

The RNAi constructs may further comprise a ligand to facilitate delivery or uptake of the RNAi constructs to specific tissues or cells, such as liver cells. In certain embodiments, the ligand targets delivery of the RNAi constructs to hepatocytes. In these and other embodiments, the ligand may comprise galactose, galactosamine, or N-acetyl-galactosamine (GalNAc). In certain embodiments, the ligand comprises a multivalent galactose or multivalent GalNAc moiety, such as a trivalent or tetravalent galactose or GalNAc moiety. The ligand may be covalently attached to the 5' or 3' end of the sense strand of the RNAi construct, optionally through a linker. In certain embodiments, the ligand comprises a structure of Structure 1 as described herein. In one such embodiment, the ligand having this structure is covalently attached to the 5' end of the sense strand, optionally via a linker, such as an aminohexyl linker. In some embodiments, the RNAi constructs comprise a ligand and linker having a structure according to any one of Formulas I to IX described herein. In certain embodiments, the RNAi constructs comprise a ligand and linker having a structure according to Formula VII. In other embodiments, the RNAi constructs comprise a ligand and linker having a structure according to Formula IV.

The present invention also provides pharmaceutical compositions comprising any of the RNAi constructs described herein and a pharmaceutically acceptable carrier, excipient, or diluent. Such pharmaceutical compositions are particularly useful for reducing expression of the LPA gene in the cells (e.g. liver cells) of a patient in need thereof. Patients who may be administered a pharmaceutical composition of the invention can include patients with a history of myocardial infarction, patients diagnosed with or at risk for coronary artery disease or other form of cardiovascular disease, and patients with elevated levels of serum or plasma Lp(a). Accordingly, the present invention includes methods of treating or preventing cardiovascular disease in a patient in need thereof by administering an RNAi construct or pharmaceutical composition described herein. In certain embodiments, the present invention provides methods for reducing Lp(a) levels in a patient in need thereof by administering an RNAi construct or pharmaceutical composition described herein.

The use of LPA-targeting RNAi constructs in any of the methods described herein or for preparation of medicaments for administration according to the methods described herein is specifically contemplated. For instance, the present invention includes an LPA-targeting RNAi construct for use in a method for treating or preventing cardiovascular disease, including coronary artery disease, peripheral artery disease, myocardial infarction, or stroke, in a patient in need thereof. The present invention also includes an LPA-targeting RNAi construct for use in a method for reducing Lp(a) levels in a patient in need thereof. In some embodiments, the present invention provides an LPA-targeting RNAi construct for use in a method for reducing the risk of myocardial infarction in a patient in need thereof.

The present invention also encompasses the use of an LPA-targeting RNAi construct in the preparation of a medicament for treating or preventing cardiovascular disease, including coronary artery disease, peripheral artery disease, myocardial infarction, or stroke, in a patient in need thereof. In certain embodiments, the present invention provides the use of an LPA-targeting RNAi construct in the preparation of a medicament for reducing Lp(a) levels in a patient in need thereof. In certain other embodiments, the present invention provides the use of an LPA-targeting RNAi construct in the preparation of a medicament for reducing the risk of myocardial infarction in a patient in need thereof.

BRIEF DESCRIPTION OF THE DRAWINGS

FIG. 1 shows the nucleotide sequence of a transcript of human LPA (NCBI Reference Sequence No. NM_005577.4; SEQ ID NO: 1). The transcript sequence is depicted as the complementary DNA (cDNA) sequence with thymine bases replacing uracil bases.

DETAILED DESCRIPTION

Figure 2:
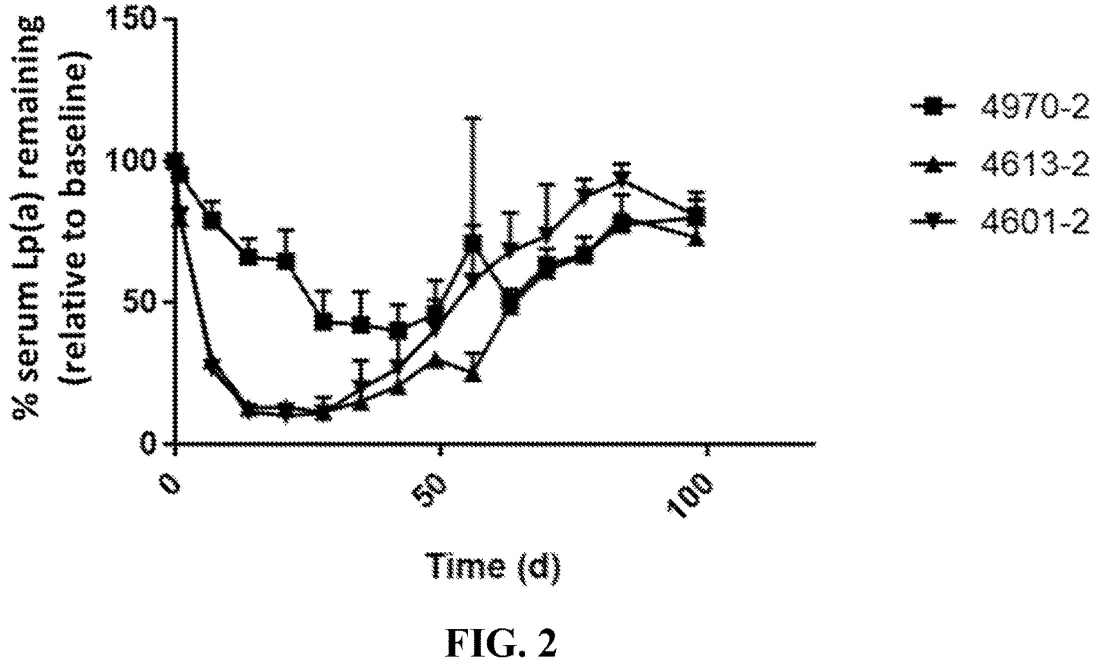
FIG. 2 shows the percentage of serum Lp(a) remaining relative to pre-dose baseline levels in cynomolgus monkeys following administration of a single subcutaneous injection of 2 mg/kg of the indicated LPA RNAi constructs on day 1.

The present invention is directed to compositions and methods for regulating the expression of the LPA gene in a cell or mammal. In some embodiments, compositions of the invention comprise RNAi constructs that target a mRNA transcribed from the LPA gene, which encodes the apo(a) protein, and reduce apo(a) expression in a cell or mammal. Such RNAi constructs are useful for reducing Lp(a) serum levels and treating or preventing various forms of cardiovascular disease, such as atherosclerosis, coronary artery disease, peripheral artery disease, aortic stenosis, and reducing the risk of myocardial infarction or stroke.

As used herein, the term “RNAi construct” refers to an agent comprising an RNA molecule that is capable of downregulating expression of a target gene (e.g. LPA gene)

via an RNA interference mechanism when introduced into a cell. RNA interference is the process by which a nucleic acid molecule induces the cleavage and degradation of a target RNA molecule (e.g. messenger RNA or mRNA molecule) in a sequence-specific manner, e.g. through an RNA-induced silencing complex (RISC) pathway. In some embodiments, the RNAi construct comprises a double-stranded RNA molecule comprising two antiparallel strands of contiguous nucleotides that are sufficiently complementary to each other to hybridize to form a duplex region. "Hybridize" or "hybridization" refers to the pairing of complementary polynucleotides, typically via hydrogen bonding (e.g. Watson-Crick, Hoogsteen or reversed Hoogsteen hydrogen bonding) between complementary bases in the two polynucleotides. The strand comprising a region having a sequence that is substantially complementary to a target sequence (e.g. target mRNA) is referred to as the "antisense strand." The "sense strand" refers to the strand that includes a region that is substantially complementary to a region of the antisense strand. In some embodiments, the sense strand may comprise a region that has a sequence that is substantially identical to the target sequence.

A double-stranded RNA molecule may include chemical modifications to ribonucleotides, including modifications to the ribose sugar, base, or backbone components of the ribonucleotides, such as those described herein or known in the art. Any such modifications, as used in a double-stranded RNA molecule (e.g. siRNA, shRNA, or the like), are encompassed by the term "double-stranded RNA" for the purposes of this disclosure.

As used herein, a first sequence is "complementary" to a second sequence if a polynucleotide comprising the first sequence can hybridize to a polynucleotide comprising the second sequence to form a duplex region under certain conditions, such as physiological conditions. Other such conditions can include moderate or stringent hybridization conditions, which are known to those of skill in the art. A first sequence is considered to be fully complementary (100% complementary) to a second sequence if a polynucleotide comprising the first sequence base pairs with a polynucleotide comprising the second sequence over the entire length of one or both nucleotide sequences without any mismatches. A sequence is "substantially complementary" to a target sequence if the sequence is at least about 80%, 85%, 90%, 95%, 96%, 97%, 98%, or 99% complementary to a target sequence. Percent complementarity can be calculated by dividing the number of bases in a first sequence that are complementary to bases at corresponding positions in a second or target sequence by the total length of the first sequence. A sequence may also be said to be substantially complementary to another sequence if there are no more than 5, 4, 3, or 2 mismatches over a 30 base pair duplex region when the two sequences are hybridized. Generally, if any nucleotide overhangs, as defined herein, are present, the sequence of such overhangs is not considered in determining the degree of complementarity between two sequences. By way of example, a sense strand of 21 nucleotides in length and an antisense strand of 21 nucleotides in length that hybridize to form a 19 base pair duplex region with a 2-nucleotide overhang at the 3' end of each strand would be considered to be fully complementary as the term is used herein.

In some embodiments, a region of the antisense strand comprises a sequence that is substantially or fully complementary to a region of the target RNA sequence (e.g. LPA mRNA). In such embodiments, the sense strand may comprise a sequence that is fully complementary to the sequence of the antisense strand. In other such embodiments, the sense strand may comprise a sequence that is substantially complementary to the sequence of the antisense strand, e.g. having 1, 2, 3, 4, or 5 mismatches in the duplex region formed by the sense and antisense strands. In certain embodiments, it is preferred that any mismatches occur within the terminal regions (e.g. within 6, 5, 4, 3, or 2 nucleotides of the 5' and/or 3' ends of the strands). In one embodiment, any mismatches in the duplex region formed from the sense and antisense strands occur within 6, 5, 4, 3, or 2 nucleotides of the 5' end of the antisense strand.

In certain embodiments, the sense strand and antisense strand of the double-stranded RNA may be two separate molecules that hybridize to form a duplex region but are otherwise unconnected. Such double-stranded RNA molecules formed from two separate strands are referred to as "small interfering RNAs" or "short interfering RNAs" (siRNAs). Thus, in some embodiments, the RNAi constructs of the invention comprise an siRNA.

In other embodiments, the sense strand and the antisense strand that hybridize to form a duplex region may be part of a single RNA molecule, i.e. the sense and antisense strands are part of a self-complementary region of a single RNA molecule. In such cases, a single RNA molecule comprises a duplex region (also referred to as a stem region) and a loop region. The 3' end of the sense strand is connected to the 5' end of the antisense strand by a contiguous sequence of unpaired nucleotides, which will form the loop region. The loop region is typically of a sufficient length to allow the RNA molecule to fold back on itself such that the antisense strand can base pair with the sense strand to form the duplex or stem region. The loop region can comprise from about 3 to about 25, from about 5 to about 15, or from about 8 to about 12 unpaired nucleotides. Such RNA molecules with at least partially self-complementary regions are referred to as "short hairpin RNAs" (shRNAs). In certain embodiments, the RNAi constructs of the invention comprise a shRNA. The length of a single, at least partially self-complementary RNA molecule can be from about 40 nucleotides to about 100 nucleotides, from about 45 nucleotides to about 85 nucleotides, or from about 50 nucleotides to about 60 nucleotides and comprise a duplex region and loop region each having the lengths recited herein.

In some embodiments, the RNAi constructs of the invention comprise a sense strand and an antisense strand, wherein the antisense strand comprises a region having a sequence that is substantially or fully complementary to an LPA messenger RNA (mRNA) sequence. As used herein, an "LPA mRNA sequence" refers to any messenger RNA sequence, including allelic variants and splice variants, encoding an apo(a) protein, including apo(a) protein variants or isoforms from any species (e.g. non-human primate, human). The LPA gene (also known as AK38, APOA, and LP) encodes the apo(a) protein, which is a primary component of the low-density lipoprotein particle known as lipoprotein (a) or Lp(a). In humans, the LPA gene is found on chromosome 6 at locus 6q25.3-q26. The LPA gene is highly polymorphic with alleles of the gene differing in numbers of copies of the kringle IV type 2 (KIV-2) domain, which can range from two to over 40 copies among individuals (see, e.g., Kronenberg and Utermann, J. Intern. Med., Vol. 273: 6-30, 2013).

An LPA mRNA sequence also includes the transcript sequence expressed as its complementary DNA (cDNA) sequence. A cDNA sequence refers to the sequence of an mRNA transcript expressed as DNA bases (e.g. guanine, adenine, thymine, and cytosine) rather than RNA bases (e.g.

guanine, adenine, uracil, and cytosine). Thus, the antisense strand of the RNAi constructs of the invention may comprise a region having a sequence that is substantially or fully complementary to a target LPA mRNA sequence or LPA cDNA sequence. An LPA mRNA or cDNA sequence can include, but is not limited to, any LPA mRNA or cDNA sequence selected from the NCBI Reference sequences NM_005577.4 (human; FIG. 1, SEQ ID NO: 1), XM_015448520.1 (cynomolgus monkey), XM_028847001.1 (rhesus monkey), XM_024357489.1 (chimpanzee), and XM_031012244.1 (gorilla). In certain embodiments, the LPA mRNA sequence is the human transcript listed in the NCBI database as Reference Sequence NM_005577.4 (see FIG. 1; SEQ ID NO: 1).

A region of the antisense strand can be substantially complementary or fully complementary to at least 15 consecutive nucleotides of the LPA mRNA sequence. In some embodiments, the target region of the LPA mRNA sequence to which the antisense strand comprises a region of complementarity can range from about 15 to about 30 consecutive nucleotides, from about 16 to about 28 consecutive nucleotides, from about 18 to about 26 consecutive nucleotides, from about 17 to about 24 consecutive nucleotides, from about 19 to about 30 consecutive nucleotides, from about 19 to about 25 consecutive nucleotides, from about 19 to about 23 consecutive nucleotides, or from about 19 to about 21 consecutive nucleotides. In certain embodiments, the region of the antisense strand comprising a sequence that is substantially or fully complementary to an LPA mRNA sequence may, in some embodiments, comprise at least 15 contiguous nucleotides from an antisense sequence listed in Table 1 or Table 2. In other embodiments, the antisense sequence comprises at least 16, at least 17, at least 18, or at least 19 contiguous nucleotides from an antisense sequence listed in Table 1 or Table 2.

The sense strand of the RNAi construct typically comprises a sequence that is sufficiently complementary to the sequence of the antisense strand such that the two strands hybridize under physiological conditions to form a duplex region. A "duplex region" refers to the region in two complementary or substantially complementary polynucleotides that form base pairs with one another, either by Watson-Crick base pairing or other hydrogen bonding interaction, to create a duplex between the two polynucleotides. The duplex region of the RNAi construct should be of sufficient length to allow the RNAi construct to enter the RNA interference pathway, e.g. by engaging the Dicer enzyme and/or the RISC complex. For instance, in some embodiments, the duplex region is about 15 to about 30 base pairs in length. Other lengths for the duplex region within this range are also suitable, such as about 15 to about 28 base pairs, about 15 to about 26 base pairs, about 15 to about 24 base pairs, about 15 to about 22 base pairs, about 17 to about 28 base pairs, about 17 to about 26 base pairs, about 17 to about 24 base pairs, about 17 to about 23 base pairs, about 17 to about 21 base pairs, about 19 to about 25 base pairs, about 19 to about 23 base pairs, or about 19 to about 21 base pairs. In certain embodiments, the duplex region is about 17 to about 24 base pairs in length. In other embodiments, the duplex region is about 19 to about 21 base pairs in length. In one embodiment, the duplex region is about 19 base pairs in length. In another embodiment, the duplex region is about 21 base pairs in length.

For embodiments in which the sense strand and antisense strand are two separate molecules (e.g. RNAi construct comprises an siRNA), the sense strand and antisense strand need not be the same length as the length of the duplex region. For instance, one or both strands may be longer than the duplex region and have one or more unpaired nucleotides or mismatches flanking the duplex region. Thus, in some embodiments, the RNAi construct comprises at least one nucleotide overhang. As used herein, a "nucleotide overhang" refers to the unpaired nucleotide or nucleotides that extend beyond the duplex region at the terminal ends of the strands. Nucleotide overhangs are typically created when the 3' end of one strand extends beyond the 5' end of the other strand or when the 5' end of one strand extends beyond the 3' end of the other strand. The length of a nucleotide overhang is generally between 1 and 6 nucleotides, 1 and 5 nucleotides, 1 and 4 nucleotides, 1 and 3 nucleotides, 2 and 6 nucleotides, 2 and 5 nucleotides, or 2 and 4 nucleotides. In some embodiments, the nucleotide overhang comprises 1, 2, 3, 4, 5, or 6 nucleotides. In one particular embodiment, the nucleotide overhang comprises 1 to 4 nucleotides. In certain embodiments, the nucleotide overhang comprises 2 nucleotides. In certain other embodiments, the nucleotide overhang comprises a single nucleotide.

The nucleotides in the overhang can be ribonucleotides or modified nucleotides as described herein. In some embodiments, the nucleotides in the overhang are 2'-modified nucleotides (e.g. 2'-fluoro modified nucleotides, 2'-O-methyl modified nucleotides), deoxyribonucleotides, abasic nucleotides, inverted nucleotides (e.g. inverted abasic nucleotides, inverted deoxyribonucleotides), or combinations thereof. For instance, in one embodiment, the nucleotides in the overhang are deoxyribonucleotides, e.g. deoxythymidine. In another embodiment, the nucleotides in the overhang are 2'-O-methyl modified nucleotides, 2'-fluoro modified nucleotides, 2'-methoxyethyl modified nucleotides, or combinations thereof. In other embodiments, the overhang comprises a 5'-uridine-uridine-3' (5'-UU-3') dinucleotide. In such embodiments, the UU dinucleotide may comprise ribonucleotides or modified nucleotides, e.g. 2'-modified nucleotides. In other embodiments, the overhang comprises a 5'-deoxythymidine-deoxythymidine-3' (5'-dTdT-3') dinucleotide. When a nucleotide overhang is present in the antisense strand, the nucleotides in the overhang can be complementary to the target gene sequence, form a mismatch with the target gene sequence, or comprise some other sequence (e.g. polypyrimidine or polypurine sequence, such as UU, TT, AA, GG, etc.).

The nucleotide overhang can be at the 5' end or 3' end of one or both strands. For example, in one embodiment, the RNAi construct comprises a nucleotide overhang at the 5' end and the 3' end of the antisense strand. In another embodiment, the RNAi construct comprises a nucleotide overhang at the 5' end and the 3' end of the sense strand. In some embodiments, the RNAi construct comprises a nucleotide overhang at the 5' end of the sense strand and the 5' end of the antisense strand. In other embodiments, the RNAi construct comprises a nucleotide overhang at the 3' end of the sense strand and the 3' end of the antisense strand.

The RNAi constructs may comprise a single nucleotide overhang at one end of the double-stranded RNA molecule and a blunt end at the other. A "blunt end" means that the sense strand and antisense strand are fully base-paired at the end of the molecule and there are no unpaired nucleotides that extend beyond the duplex region. In some embodiments, the RNAi construct comprises a nucleotide overhang at the 3' end of the sense strand and a blunt end at the 5' end of the sense strand and 3' end of the antisense strand. In other embodiments, the RNAi construct comprises a nucleotide overhang at the 3' end of the antisense strand and a blunt end at the 5' end of the antisense strand and the 3' end of the sense strand. In certain embodiments, the RNAi construct comprises a blunt end at both ends of the double-stranded RNA molecule. In such embodiments, the sense strand and antisense strand have the same length and the duplex region is the same length as the sense and antisense strands (i.e. the molecule is double stranded over its entire length).

The sense strand and antisense strand in the RNAi constructs of the invention can each independently be about 15 to about 30 nucleotides in length, about 19 to about 30 nucleotides in length, about 18 to about 28 nucleotides in length, about 19 to about 27 nucleotides in length, about 19 to about 25 nucleotides in length, about 19 to about 23 nucleotides in length, about 19 to about 21 nucleotides in length, about 21 to about 25 nucleotides in length, or about 21 to about 23 nucleotides in length. In certain embodiments, the sense strand and antisense strand are each independently about 18, about 19, about 20, about 21, about 22, about 23, about 24, or about 25 nucleotides in length. In some embodiments, the sense strand and antisense strand have the same length but form a duplex region that is shorter than the strands such that the RNAi construct has two nucleotide overhangs. For instance, in one embodiment, the RNAi construct comprises (i) a sense strand and an antisense strand that are each 21 nucleotides in length, (ii) a duplex region that is 19 base pairs in length, and (iii) nucleotide overhangs of 2 unpaired nucleotides at both the 3' end of the sense strand and the 3' end of the antisense strand. In another embodiment, the RNAi construct comprises (i) a sense strand and an antisense strand that are each 23 nucleotides in length, (ii) a duplex region that is 21 base pairs in length, and (iii) nucleotide overhangs of 2 unpaired nucleotides at both the 3' end of the sense strand and the 3' end of the antisense strand. In other embodiments, the sense strand and antisense strand have the same length and form a duplex region over their entire length such that there are no nucleotide overhangs on either end of the double-stranded molecule. In one such embodiment, the RNAi construct is blunt ended and comprises (i) a sense strand and an antisense strand, each of which is 21 nucleotides in length, and (ii) a duplex region that is 21 base pairs in length. In another such embodiment, the RNAi construct is blunt ended and comprises (i) a sense strand and an antisense strand, each of which is 23 nucleotides in length, and (ii) a duplex region that is 23 base pairs in length. In still another such embodiment, the RNAi construct is blunt ended and comprises (i) a sense strand and an antisense strand, each of which is 19 nucleotides in length, and (ii) a duplex region that is 19 base pairs in length.

In other embodiments, the sense strand or the antisense strand is longer than the other strand and the two strands form a duplex region having a length equal to that of the shorter strand such that the RNAi construct comprises at least one nucleotide overhang. For example, in one embodiment, the RNAi construct comprises (i) a sense strand that is 19 nucleotides in length, (ii) an antisense strand that is 21 nucleotides in length, (iii) a duplex region of 19 base pairs in length, and (iv) a nucleotide overhang of 2 unpaired nucleotides at the 3' end of the antisense strand. In another embodiment, the RNAi construct comprises (i) a sense strand that is 21 nucleotides in length, (ii) an antisense strand that is 23 nucleotides in length, (iii) a duplex region of 21 base pairs in length, and (iv) a nucleotide overhang of 2 unpaired nucleotides at the 3' end of the antisense strand.

The antisense strand of the RNAi constructs of the invention can comprise or consist of the sequence of any one of the antisense sequences listed in Table 1 or Table 2, the sequence of nucleotides 1-19 of any of these antisense sequences, or the sequence of nucleotides 2-19 of any of these antisense sequences. Thus, in some embodiments, the antisense strand comprises or consists of a sequence selected from SEQ ID NOs: 134-241, 437-601, 611, or 617-619. In other embodiments, the antisense strand comprises or consists of a sequence of nucleotides 1-19 of any one of SEQ ID NOs: 134-241, 437-601, 611, or 617-619. In still other embodiments, the antisense strand comprises or consists of a sequence of nucleotides 2-19 of any one of SEQ ID NOs: 134-241, 437-601, 611, or 617-619. In certain embodiments, the antisense strand comprises or consists of a sequence selected from SEQ ID NO: 137, SEQ ID NO: 145, SEQ ID NO: 164, SEQ ID NO: 175, SEQ ID NO: 177, SEQ ID NO: 178, SEQ ID NO: 189, SEQ ID NO: 194, SEQ ID NO: 196, SEQ ID NO: 198, SEQ ID NO: 200, SEQ ID NO: 205, SEQ ID NO: 216, SEQ ID NO: 224, SEQ ID NO: 225, SEQ ID NO: 440, SEQ ID NO: 448, SEQ ID NO: 471, SEQ ID NO: 492, SEQ ID NO: 497, SEQ ID NO: 499, SEQ ID NO: 515, SEQ ID NO: 525, SEQ ID NO: 530, SEQ ID NO: 536, SEQ ID NO: 540, SEQ ID NO: 546, SEQ ID NO: 547, SEQ ID NO: 550, SEQ ID NO: 568, SEQ ID NO: 576, or SEQ ID NO: 577. In some embodiments, the antisense strand comprises or consists of a sequence selected from SEQ ID NO: 145, SEQ ID NO: 175, SEQ ID NO: 177, SEQ ID NO: 194, SEQ ID NO: 196, SEQ ID NO: 198, SEQ ID NO: 200, SEQ ID NO: 448, SEQ ID NO: 492, SEQ ID NO: 497, SEQ ID NO: 525, SEQ ID NO: 530, SEQ ID NO: 536, or SEQ ID NO: 540.

In these and other embodiments, the sense strand of the RNAi constructs of the invention can comprise or consist of the sequence of any one of the sense sequences listed in Table 1 or Table 2, the sequence of nucleotides 1-19 of any of these sense sequences, or the sequence of nucleotides 2-19 of any of these sense sequences. Thus, in some embodiments, the sense strand comprises or consists of a sequence selected from SEQ ID NOs: 2-133, 242-436, 610, or 612-616. In other embodiments, the sense strand comprises or consists of a sequence of nucleotides 1-19 of any one of SEQ ID NOs: 2-133, 242-436, 610, or 612-616. In still other embodiments, the sense strand comprises or consists of a sequence of nucleotides 2-19 of any one of SEQ ID NOs: 2-133, 242-436, 610, or 612-616. In certain embodiments, the sense strand comprises or consists of a sequence selected from SEQ ID NO: 5, SEQ ID NO: 13, SEQ ID NO: 35, SEQ ID NO: 49, SEQ ID NO: 51, SEQ ID NO: 53, SEQ ID NO: 54, SEQ ID NO: 71, SEQ ID NO: 78, SEQ ID NO: 79, SEQ ID NO: 83, SEQ ID NO: 85, SEQ ID NO: 86, SEQ ID NO: 91, SEQ ID NO: 106, SEQ ID NO: 115, SEQ ID NO: 117, SEQ ID NO: 245, SEQ ID NO: 253, SEQ ID NO: 282, SEQ ID NO: 304, SEQ ID NO: 307, SEQ ID NO: 312, SEQ ID NO: 314, SEQ ID NO: 341, SEQ ID NO: 350, SEQ ID NO: 357, SEQ ID NO: 362, SEQ ID NO: 364, SEQ ID NO: 370, SEQ ID NO: 372, SEQ ID NO: 377, SEQ ID NO: 378, SEQ ID NO: 404, SEQ ID NO: 413, or SEQ ID NO: 415. In certain other embodiments, the sense strand comprises or consists of a sequence selected from SEQ ID NO: 13, SEQ ID NO: 49, SEQ ID NO: 51, SEQ ID NO: 53, SEQ ID NO: 78, SEQ ID NO: 79, SEQ ID NO: 83, SEQ ID NO: 85, SEQ ID NO: 106, SEQ ID NO: 253, SEQ ID NO: 304, SEQ ID NO: 307, SEQ ID NO: 312, SEQ ID NO: 350, SEQ ID NO: 357, SEQ ID NO: 362, SEQ ID NO: 370, or SEQ ID NO: 404.

In certain embodiments of the invention, the RNAi constructs comprise (i) a sense strand comprising or consisting of a sequence selected from 2-133, 242-436, 610, or 612-616 and (ii) an antisense strand comprising or consisting of a sequence selected from SEQ ID NOs: 134-241, 437-601, 611, or 617-619. In some embodiments, the RNAi constructs comprise (i) a sense strand comprising or consisting of a sequence selected from SEQ ID NO: 5, SEQ ID NO: 13, SEQ ID NO: 35, SEQ ID NO: 49, SEQ ID NO: 51, SEQ ID NO: 53, SEQ ID NO: 54, SEQ ID NO: 71, SEQ ID NO: 78, SEQ ID NO: 79, SEQ ID NO: 83, SEQ ID NO: 85, SEQ ID NO: 86, SEQ ID NO: 91, SEQ ID NO: 106, SEQ ID NO: 115, SEQ ID NO: 117, SEQ ID NO: 245, SEQ ID NO: 253, SEQ ID NO: 282, SEQ ID NO: 304, SEQ ID NO: 307, SEQ ID NO: 312, SEQ ID NO: 314, SEQ ID NO: 341, SEQ ID NO: 350, SEQ ID NO: 357, SEQ ID NO: 362, SEQ ID NO: 364, SEQ ID NO: 370, SEQ ID NO: 372, SEQ ID NO: 377, SEQ ID NO: 378, SEQ ID NO: 404, SEQ ID NO: 413, or SEQ ID NO: 415 and (ii) an antisense strand comprising or consisting of a sequence selected from SEQ ID NO: 137, SEQ ID NO: 145, SEQ ID NO: 164, SEQ ID NO: 175, SEQ ID NO: 177, SEQ ID NO: 178, SEQ ID NO: 189, SEQ ID NO: 194, SEQ ID NO: 196, SEQ ID NO: 198, SEQ ID NO: 200, SEQ ID NO: 205, SEQ ID NO: 216, SEQ ID NO: 224, SEQ ID NO: 225, SEQ ID NO: 440, SEQ ID NO: 448, SEQ ID NO: 471, SEQ ID NO: 492, SEQ ID NO: 497, SEQ ID NO: 499, SEQ ID NO: 515, SEQ ID NO: 525, SEQ ID NO: 530, SEQ ID NO: 536, SEQ ID NO: 540, SEQ ID NO: 546, SEQ ID NO: 547, SEQ ID NO: 550, SEQ ID NO: 568, SEQ ID NO: 576, or SEQ ID NO: 577. In other embodiments, the RNAi constructs comprise (i) a sense strand comprising or consisting of a sequence selected from SEQ ID NO: 13, SEQ ID NO: 49, SEQ ID NO: 51, SEQ ID NO: 53, SEQ ID NO: 78, SEQ ID NO: 79, SEQ ID NO: 83, SEQ ID NO: 85, SEQ ID NO: 106, SEQ ID NO: 253, SEQ ID NO: 304, SEQ ID NO: 307, SEQ ID NO: 312, SEQ ID NO: 350, SEQ ID NO: 357, SEQ ID NO: 362, SEQ ID NO: 370, or SEQ ID NO: 404 and (ii) an antisense strand comprising or consisting of a sequence selected from SEQ ID NO: 145, SEQ ID NO: 175, SEQ ID NO: 177, SEQ ID NO: 194, SEQ ID NO: 196, SEQ ID NO: 198, SEQ ID NO: 200, SEQ ID NO: 448, SEQ ID NO: 492, SEQ ID NO: 497, SEQ ID NO: 525, SEQ ID NO: 530, SEQ ID NO: 536, or SEQ ID NO: 540.

In certain embodiments, the RNAi constructs of the invention comprise: (i) a sense strand comprising or consisting of the sequence of SEQ ID NO: 13 and an antisense strand comprising or consisting of the sequence of SEQ ID NO: 145; (ii) a sense strand comprising or consisting of the sequence of SEQ ID NO: 35 and an antisense strand comprising or consisting of the sequence of SEQ ID NO: 164; (iii) a sense strand comprising or consisting of the sequence of SEQ ID NO: 53 and an antisense strand comprising or consisting of the sequence of SEQ ID NO: 177; (iv) a sense strand comprising or consisting of the sequence of SEQ ID NO: 91 and an antisense strand comprising or consisting of the sequence of SEQ ID NO: 205; (v) a sense strand comprising or consisting of the sequence of SEQ ID NO: 49 and an antisense strand comprising or consisting of the sequence of SEQ ID NO: 175; (vi) a sense strand comprising or consisting of the sequence of SEQ ID NO: 71 and an antisense strand comprising or consisting of the sequence of SEQ ID NO: 189; (vii) a sense strand comprising or consisting of the sequence of SEQ ID NO: 51 and an antisense strand comprising or consisting of the sequence of SEQ ID NO: 175; (viii) a sense strand comprising or consisting of the sequence of SEQ ID NO: 79 and an antisense strand comprising or consisting of the sequence of SEQ ID NO: 194; (ix) a sense strand comprising or consisting of the sequence of SEQ ID NO: 85 and an antisense strand comprising or consisting of the sequence of SEQ ID NO: 198; (x) a sense strand comprising or consisting of the sequence of SEQ ID NO: 106 and an antisense strand comprising or consisting of the sequence of SEQ ID NO: 216; (xi) a sense strand comprising or consisting of the sequence of SEQ ID NO: 83 and an antisense strand comprising or consisting of the sequence of SEQ ID NO: 200; (xii) a sense strand comprising or consisting of the sequence of SEQ ID NO: 78 and an antisense strand comprising or consisting of the sequence of SEQ ID NO: 196; (xiii) a sense strand comprising or consisting of the sequence of SEQ ID NO: 5 and an antisense strand comprising or consisting of the sequence of SEQ ID NO: 137; (xiv) a sense strand comprising or consisting of the sequence of SEQ ID NO: 117 and an antisense strand comprising or consisting of the sequence of SEQ ID NO: 225; (xv) a sense strand comprising or consisting of the sequence of SEQ ID NO: 115 and an antisense strand comprising or consisting of the sequence of SEQ ID NO: 224; (xvi) a sense strand comprising or consisting of the sequence of SEQ ID NO: 54 and an antisense strand comprising or consisting of the sequence of SEQ ID NO: 178, or (xvii) a sense strand comprising or consisting of the sequence of SEQ ID NO: 86 and an antisense strand comprising or consisting of the sequence of SEQ ID NO: 198.

In some embodiments, the RNAi constructs of the invention comprise: (i) a sense strand comprising or consisting of the sequence of modified nucleotides according to SEQ ID NO: 253 and an antisense strand comprising or consisting of the sequence of modified nucleotides according to SEQ ID NO: 448; (ii) a sense strand comprising or consisting of the sequence of modified nucleotides according to SEQ ID NO: 282 and an antisense strand comprising or consisting of the sequence of modified nucleotides according to SEQ ID NO: 471; (iii) a sense strand comprising or consisting of the sequence of modified nucleotides according to SEQ ID NO: 312 and an antisense strand comprising or consisting of the sequence of modified nucleotides according to SEQ ID NO: 497; (iv) a sense strand comprising or consisting of the sequence of modified nucleotides according to SEQ ID NO: 378 and an antisense strand comprising or consisting of the sequence of modified nucleotides according to SEQ ID NO: 547; (v) a sense strand comprising or consisting of the sequence of modified nucleotides according to SEQ ID NO: 304 and an antisense strand comprising or consisting of the sequence of modified nucleotides according to SEQ ID NO: 492; (vi) a sense strand comprising or consisting of the sequence of modified nucleotides according to SEQ ID NO: 341 and an antisense strand comprising or consisting of the sequence of modified nucleotides according to SEQ ID NO: 515; (vii) a sense strand comprising or consisting of the sequence of modified nucleotides according to SEQ ID NO: 377 and an antisense strand comprising or consisting of the sequence of modified nucleotides according to SEQ ID NO: 550; (viii) a sense strand comprising or consisting of the sequence of modified nucleotides according to SEQ ID NO: 307 and an antisense strand comprising or consisting of the sequence of modified nucleotides according to SEQ ID NO: 492; (ix) a sense strand comprising or consisting of the sequence of modified nucleotides according to SEQ ID NO: 350 and an antisense strand comprising or consisting of the sequence of modified nucleotides according to SEQ ID NO: 525; (x) a sense strand comprising or consisting of the sequence of modified nucleotides according to SEQ ID NO: 362 and an antisense strand comprising or consisting of the sequence of modified nucleotides according to SEQ ID NO: 536; (xi) a sense strand comprising or consisting of the sequence of modified nucleotides according to SEQ ID NO: 404 and an antisense strand comprising or consisting of the sequence of modified nucleotides according to SEQ ID NO: 568; (xii) a sense strand comprising or consisting of the sequence of modified nucleotides according to SEQ ID NO: 370 and an antisense strand comprising or consisting of the sequence of modified nucleotides according to SEQ ID NO: 540; (xiii) a sense strand comprising or consisting of the sequence of modified nucleotides according to SEQ ID NO: 357 and an antisense strand comprising or consisting of the sequence of modified nucleotides according to SEQ ID NO: 530; (xiv) a sense strand comprising or consisting of the sequence of modified nucleotides according to SEQ ID NO: 245 and an antisense strand comprising or consisting of the sequence of modified nucleotides according to SEQ ID NO: 440; (xv) a sense strand comprising or consisting of the sequence of modified nucleotides according to SEQ ID NO: 415 and an antisense strand comprising or consisting of the sequence of modified nucleotides according to SEQ ID NO: 577; (xvi) a sense strand comprising or consisting of the sequence of modified nucleotides according to SEQ ID NO: 413 and an antisense strand comprising or consisting of the sequence of modified nucleotides according to SEQ ID NO: 576; (xvii) a sense strand comprising or consisting of the sequence of modified nucleotides according to SEQ ID NO: 314 and an antisense strand comprising or consisting of the sequence of modified nucleotides according to SEQ ID NO: 499; (xviii) a sense strand comprising or consisting of the sequence of modified nucleotides according to SEQ ID NO: 377 and an antisense strand comprising or consisting of the sequence of modified nucleotides according to SEQ ID NO: 546; (xix) a sense strand comprising or consisting of the sequence of modified nucleotides according to SEQ ID NO: 364 and an antisense strand comprising or consisting of the sequence of modified nucleotides according to SEQ ID NO: 536; or (xx) a sense strand comprising or consisting of the sequence of modified nucleotides according to SEQ ID NO: 372 and an antisense strand comprising or consisting of the sequence of modified nucleotides according to SEQ ID NO: 540.

The RNAi construct of the invention can be any one of the duplex compounds listed in Tables 1 to 15 (including the unmodified nucleotide sequences and/or modified nucleotide sequences of the compounds). In some embodiments, the RNAi construct is any of the duplex compounds listed in Table 1. In other embodiments, the RNAi construct is any of the duplex compounds listed in Table 2 (including the unmodified nucleotide sequences and/or modified nucleotide sequences of the compounds). In certain embodiments, the RNAi construct is 4601, 4613, 4930, 4970, 6150, 6182, 6247, 8395, 8401, 10927, 11318, 11344, 11351, 11374, 11580, 17188, 17205, 18436, 18444 or 18446. In one particular embodiment, the RNAi construct is 4601. In another particular embodiment, the RNAi construct is 4613. In another embodiment, the RNAi construct is 10927. In another embodiment, the RNAi construct is 11351. In another embodiment, the RNAi construct is 11374. In still another embodiment, the RNAi construct is 11580. In yet another embodiment, the RNAi construct is 18436. In another embodiment, the RNAi construct is 18444.

The RNAi constructs of the invention may comprise one or more modified nucleotides. A "modified nucleotide" refers to a nucleotide that has one or more chemical modifications to the nucleoside, nucleobase, pentose ring, or phosphate group. As used herein, modified nucleotides do not encompass ribonucleotides containing adenosine monophosphate, guanosine monophosphate, uridine monophosphate, and cytidine monophosphate. However, the RNAi constructs may comprise combinations of modified nucleotides and ribonucleotides. Incorporation of modified nucleotides into one or both strands of double-stranded RNA molecules can improve the in vivo stability of the RNA molecules, e.g., by reducing the molecules' susceptibility to nucleases and other degradation processes. The potency of RNAi constructs for reducing expression of the target gene can also be enhanced by incorporation of modified nucleotides.

In certain embodiments, the modified nucleotides have a modification of the ribose sugar. These sugar modifications can include modifications at the 2' and/or 5' position of the pentose ring as well as bicyclic sugar modifications. A 2'-modified nucleotide refers to a nucleotide having a pentose ring with a substituent at the 2' position other than OH. Such 2'-modifications include, but are not limited to, 2'-H (e.g. deoxyribonucleotides), 2'-O-alkyl (e.g. O—$C_1$-$C_{10}$ or O—$C_1$-$C_{10}$ substituted alkyl), 2'-O-allyl (O—$CH_2CH$═$CH_2$), 2'-C-allyl, 2'-deoxy-2'-fluoro (also referred to as 2'-F or 2'-fluoro), 2'-O-methyl ($OCH_3$), 2'-O-methoxyethyl (O—$(CH_2)_2OCH_3$), 2'-$OCF_3$, 2'-O$(CH_2)_2SCH_3$, 2'-O-aminoalkyl, 2'-amino (e.g. $NH_2$), 2'-O-ethylamine, and 2'-azido. Modifications at the 5' position of the pentose ring include, but are not limited to, 5'-methyl (R or S); 5'-vinyl, and 5'-methoxy.

A "bicyclic sugar modification" refers to a modification of the pentose ring where a bridge connects two atoms of the ring to form a second ring resulting in a bicyclic sugar structure. In some embodiments the bicyclic sugar modification comprises a bridge between the 4' and 2' carbons of the pentose ring. Nucleotides comprising a sugar moiety with a bicyclic sugar modification are referred to herein as bicyclic nucleic acids or BNAs. Exemplary bicyclic sugar modifications include, but are not limited to, α-L-Methyleneoxy (4'-$CH_2$—O-2') bicyclic nucleic acid (BNA); β-D-Methyleneoxy (4'-$CH_2$—O-2') BNA (also referred to as a locked nucleic acid or LNA); Ethyleneoxy (4'-$(CH_2)_2$—O-2') BNA; Aminooxy (4'-$CH_2$—O—N(R)-2') BNA; Oxyamino (4'-$CH_2$—N(R)—O-2') BNA; Methyl(methyleneoxy) (4'-CH$(CH_3)$—O-2') BNA (also referred to as constrained ethyl or cEt); methylene-thio (4'-$CH_2$—S-2') BNA; methylene-amino (4'-$CH_2$—N(R)-2') BNA; methyl carbocyclic (4'-$CH_2$—CH$(CH_3)$-2') BNA; propylene carbocyclic (4'-$(CH_2)_3$-2') BNA; and Methoxy(ethyleneoxy) (4'-CH($CH_2$OMe)—O-2') BNA (also referred to as constrained MOE or cMOE). These and other sugar-modified nucleotides that can be incorporated into the RNAi constructs of the invention are described in U.S. Pat. No. 9,181,551, U.S. Patent Publication No. 2016/0122761, and Deleavey and Damha, Chemistry and Biology, Vol. 19: 937-954, 2012, all of which are hereby incorporated by reference in their entireties.

In some embodiments, the RNAi constructs comprise one or more 2'-fluoro modified nucleotides, 2'-O-methyl modified nucleotides, 2'-O-methoxyethyl modified nucleotides, 2' alkyl modified nucleotides, 2'-O-allyl modified nucleotides, bicyclic nucleic acids (BNAs), deoxyribonucleotides, or combinations thereof. In certain embodiments, the RNAi constructs comprise one or more 2'-fluoro modified nucleotides, 2'-O-methyl modified nucleotides, 2'-O-methoxyethyl modified nucleotides, or combinations thereof. In one particular embodiment, the RNAi constructs comprise one or more 2'-fluoro modified nucleotides, 2'-O-methyl modified nucleotides or combinations thereof.

Both the sense and antisense strands of the RNAi constructs can comprise one or multiple modified nucleotides. For instance, in some embodiments, the sense strand comprises 1, 2, 3, 4, 5, 6, 7, 8, 9, 10 or more modified nucleotides. In certain embodiments, all nucleotides in the sense strand are modified nucleotides. In some embodiments, the antisense strand comprises 1, 2, 3, 4, 5, 6, 7, 8, 9, 10 or more modified nucleotides. In other embodiments, all nucleotides in the antisense strand are modified nucleotides. In certain other embodiments, all nucleotides in the sense strand and all nucleotides in the antisense strand are modified nucleotides. In these and other embodiments, the modified nucleotides can be 2'-fluoro modified nucleotides, 2'-O-methyl modified nucleotides, or combinations thereof.

In certain embodiments, the modified nucleotides incorporated into one or both of the strands of the RNAi constructs of the invention have a modification of the nucleobase (also referred to herein as "base"). A "modified nucleobase" or "modified base" refers to a base other than the naturally occurring purine bases adenine (A) and guanine (G) and pyrimidine bases thymine (T), cytosine (C), and uracil (U). Modified nucleobases can be synthetic or naturally occurring modifications and include, but are not limited to, universal bases, 5-methylcytosine (5-me-C), 5-hydroxymethyl cytosine, xanthine (X), hypoxanthine (I), 2-aminoadenine, 6-methyladenine, 6-methylguanine, and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

In some embodiments, the modified base is a universal base. A "universal base" refers to a base analog that indiscriminately forms base pairs with all of the natural bases in RNA and DNA without altering the double helical structure of the resulting duplex region. Universal bases are known to those of skill in the art and include, but are not limited to, inosine, C-phenyl, C-naphthyl and other aromatic derivatives, azole carboxamides, and nitroazole derivatives, such as 3-nitropyrrole, 4-nitroindole, 5-nitroindole, and 6-nitroindole.

Other suitable modified bases that can be incorporated into the RNAi constructs of the invention include those described in Herdewijn, Antisense Nucleic Acid Drug Dev., Vol. 10: 297-310, 2000 and Peacock et al., J. Org. Chem., Vol. 76: 7295-7300, 2011, both of which are hereby incorporated by reference in their entireties. The skilled person is well aware that guanine, cytosine, adenine, thymine, and uracil may be replaced by other nucleobases, such as the modified nucleobases described above, without substantially altering the base pairing properties of a polynucleotide comprising a nucleotide bearing such replacement nucleobase.

In some embodiments, the sense and antisense strands of the RNAi constructs may comprise one or more abasic nucleotides. An "abasic nucleotide" or "abasic nucleoside" is a nucleotide or nucleoside that lacks a nucleobase at the 1' position of the ribose sugar. In certain embodiments, the abasic nucleotides are incorporated into the terminal ends of the sense and/or antisense strands of the RNAi constructs. In one embodiment, the sense strand comprises an abasic nucleotide as the terminal nucleotide at its 3' end, its 5' end, or both its 3' and 5' ends. In another embodiment, the antisense strand comprises an abasic nucleotide as the terminal nucleotide at its 3' end, its 5' end, or both its 3' and 5' ends. In such embodiments in which the abasic nucleotide is a terminal nucleotide, it may be an inverted nucleotide—that is, linked to the adjacent nucleotide through a 3'-3' internucleotide linkage (when on the 3' end of a strand) or through a 5'-5' internucleotide linkage (when on the 5' end of a strand) rather than the natural 3'-5' internucleotide linkage. Abasic nucleotides may also comprise a sugar modification, such as any of the sugar modifications described above. In certain embodiments, abasic nucleotides comprise a 2'-modification, such as a 2'-fluoro modification, 2'-O-methyl modification, or a 2'-H (deoxy) modification. In one embodiment, the abasic nucleotide comprises a 2'-O-methyl modification. In another embodiment, the abasic nucleotide comprises a 2'-H modification (i.e. a deoxy abasic nucleotide).

The RNAi constructs of the invention may also comprise one or more modified internucleotide linkages. As used herein, the term "modified internucleotide linkage" refers to an internucleotide linkage other than the natural 3' to 5' phosphodiester linkage. In some embodiments, the modified internucleotide linkage is a phosphorous-containing internucleotide linkage, such as a phosphotriester, aminoalkylphosphotriester, an alkylphosphonate (e.g. methylphosphonate, 3'-alkylene phosphonate), a phosphinate, a phosphoramidate (e.g. 3'-amino phosphoramidate and aminoalkylphosphoramidate), a phosphorothioate (P═S), a chiral phosphorothioate, a phosphorodithioate, a thionophosphoramidate, a thionoalkylphosphonate, a thionoalkylphosphotriester, and a boranophosphate. In one embodiment, a modified internucleotide linkage is a 2' to 5' phosphodiester linkage. In other embodiments, the modified internucleotide linkage is a non-phosphorous-containing internucleotide linkage and thus can be referred to as a modified internucleoside linkage. Such non-phosphorous-containing linkages include, but are not limited to, morpholino linkages (formed in part from the sugar portion of a nucleoside); siloxane linkages (—O—$Si(H)_2$—O—); sulfide, sulfoxide and sulfone linkages; formacetyl and thioformacetyl linkages; alkene containing backbones; sulfamate backbones; methylenemethylimino (—$CH_2$—N($CH_3$)—O—$CH_2$—) and methylenehydrazino linkages; sulfonate and sulfonamide linkages; amide linkages; and others having mixed N, O, S and $CH_2$ component parts. In one embodiment, the modified internucleoside linkage is a peptide-based linkage (e.g. aminoethylglycine) to create a peptide nucleic acid or PNA, such as those described in U.S. Pat. Nos. 5,539,082; 5,714,331; and 5,719,262. Other suitable modified internucleotide and internucleoside linkages that may be employed in the RNAi constructs of the invention are described in U.S. Pat. Nos. 6,693,187, 9,181,551, U.S. Patent Publication No. 2016/0122761, and Deleavey and Damha, Chemistry and Biology, Vol. 19: 937-954, 2012, all of which are hereby incorporated by reference in their entireties.

In certain embodiments, the RNAi constructs of the invention comprise one or more phosphorothioate internucleotide linkages. The phosphorothioate internucleotide linkages may be present in the sense strand, antisense strand, or both strands of the RNAi constructs. For instance, in some embodiments, the sense strand comprises 1, 2, 3, 4, 5, 6, 7, 8, or more phosphorothioate internucleotide linkages. In other embodiments, the antisense strand comprises 1, 2, 3, 4, 5, 6, 7, 8, or more phosphorothioate internucleotide linkages. In still other embodiments, both strands comprise 1, 2, 3, 4, 5, 6, 7, 8, or more phosphorothioate internucleotide linkages. The RNAi constructs can comprise one or more phosphorothioate internucleotide linkages at the 3'-end, the 5'-end, or both the 3'- and 5'-ends of the sense strand, the antisense strand, or both strands. For instance, in certain embodiments, the RNAi construct comprises about 1 to about 6 or more (e.g., about 1, 2, 3, 4, 5, 6 or more) consecutive phosphorothioate internucleotide linkages at the 3'-end of the sense strand, the antisense strand, or both strands. In other embodiments, the RNAi construct comprises about 1 to about 6 or more (e.g., about 1, 2, 3, 4, 5, 6 or more) consecutive phosphorothioate internucleotide linkages at the 5'-end of the sense strand, the antisense strand, or both strands.

In some embodiments, the RNAi construct comprises a single phosphorothioate internucleotide linkage between the terminal nucleotides at the 3' end of the sense strand. In other embodiments, the RNAi construct comprises two consecutive phosphorothioate internucleotide linkages between the terminal nucleotides at the 3' end of the sense strand. In one embodiment, the RNAi construct comprises a single phosphorothioate internucleotide linkage between the terminal nucleotides at the 3' end of the sense strand and a single phosphorothioate internucleotide linkage between the terminal nucleotides at the 3' end of the antisense strand. In another embodiment, the RNAi construct comprises two consecutive phosphorothioate internucleotide linkages between the terminal nucleotides at the 3' end of the antisense strand (i.e. a phosphorothioate internucleotide linkage at the first and second internucleotide linkages at the 3' end of the antisense strand). In another embodiment, the RNAi construct comprises two consecutive phosphorothioate internucleotide linkages between the terminal nucleotides at both the 3' and 5' ends of the antisense strand. In yet another embodiment, the RNAi construct comprises two consecutive phosphorothioate internucleotide linkages between the terminal nucleotides at both the 3' and 5' ends of the antisense strand and two consecutive phosphorothioate internucleotide linkages at the 5' end of the sense strand. In still another embodiment, the RNAi construct comprises two consecutive phosphorothioate internucleotide linkages between the terminal nucleotides at both the 3' and 5' ends of the antisense strand and two consecutive phosphorothioate internucleotide linkages between the terminal nucleotides at the 3' end of the sense strand. In another embodiment, the RNAi construct comprises two consecutive phosphorothioate internucleotide linkages between the terminal nucleotides at both the 3' and 5' ends of the antisense strand and two consecutive phosphorothioate internucleotide linkages between the terminal nucleotides at both the 3' and 5' ends of the sense strand (i.e. a phosphorothioate internucleotide linkage at the first and second internucleotide linkages at both the 5' and 3' ends of the antisense strand and a phosphorothioate internucleotide linkage at the first and second internucleotide linkages at both the 5' and 3' ends of the sense strand). In yet another embodiment, the RNAi construct comprises two consecutive phosphorothioate internucleotide linkages between the terminal nucleotides at both the 3' and 5' ends of the antisense strand and a single phosphorothioate internucleotide linkage between the terminal nucleotides at the 3' end of the sense strand. In any of the embodiments in which one or both strands comprise one or more phosphorothioate internucleotide linkages, the remaining internucleotide linkages within the strands can be the natural 3' to 5' phosphodiester linkages. For instance, in some embodiments, each internucleotide linkage of the sense and antisense strands is selected from phosphodiester and phosphorothioate, wherein at least one internucleotide linkage is a phosphorothioate.

In embodiments in which the RNAi construct comprises a nucleotide overhang, two or more of the unpaired nucleotides in the overhang can be connected by a phosphorothioate internucleotide linkage. In certain embodiments, all the unpaired nucleotides in a nucleotide overhang at the 3' end of the anti sense strand and/or the sense strand are connected by phosphorothioate internucleotide linkages. In other embodiments, all the unpaired nucleotides in a nucleotide overhang at the 5' end of the antisense strand and/or the sense strand are connected by phosphorothioate internucleotide linkages. In still other embodiments, all the unpaired nucleotides in any nucleotide overhang are connected by phosphorothioate internucleotide linkages.

In some embodiments of the RNAi constructs of the invention, the 5' end of the sense strand, antisense strand, or both the antisense and sense strands comprises a phosphate moiety. As used herein, the term "phosphate moiety" refers to a terminal phosphate group that includes unmodified phosphates (—O—P═O)(OH)OH) as well as modified phosphates. Modified phosphates include phosphates in which one or more of the O and OH groups is replaced with H, O, S, N(R) or alkyl where R is H, an amino protecting group or unsubstituted or substituted alkyl. Exemplary phosphate moieties include, but are not limited to, 5'-monophosphate; 5'-diphosphate; 5'-triphosphate; 5'-guanosine cap (7-methylated or non-methylated); 5'-adenosine cap or any other modified or unmodified nucleotide cap structure; 5'-monothiophosphate (phosphorothioate); 5'-monodithiophosphate (phosphorodithioate); 5'-alpha-thiotriphosphate; 5' -gamma-thiotriphosphate, 5'-phosphoramidates; 5'-vinylphosphates; 5'-alkylphosphonates (e.g., alkyl=methyl, ethyl, isopropyl, propyl, etc.); and 5'-alkyletherphosphonates (e.g., alkylether=methoxymethyl, ethoxymethyl, etc.).

The modified nucleotides that can be incorporated into the RNAi constructs of the invention may have more than one chemical modification described herein. For instance, the modified nucleotide may have a modification to the ribose sugar as well as a modification to the nucleobase. By way of example, a modified nucleotide may comprise a 2' sugar modification (e.g. 2'-fluoro or 2'-O-methyl) and comprise a modified base (e.g. 5-methyl cytosine or pseudouracil). In other embodiments, the modified nucleotide may comprise a sugar modification in combination with a modification to the 5' phosphate that would create a modified internucleotide or internucleoside linkage when the modified nucleotide was incorporated into a polynucleotide. For instance, in some embodiments, the modified nucleotide may comprise a sugar modification, such as a 2'-fluoro modification, a 2'-O-methyl modification, or a bicyclic sugar modification, as well as a 5' phosphorothioate group. Accordingly, in some embodiments, one or both strands of the RNAi constructs of the invention comprise a combination of 2' modified nucleotides or BNAs and phosphorothioate internucleotide linkages. In certain embodiments, both the sense and antisense strands of the RNAi constructs of the invention comprise a combination of 2'-fluoro modified nucleotides, 2'-O-methyl modified nucleotides, and phosphorothioate internucleotide linkages. Exemplary RNAi constructs comprising modified nucleotides and internucleotide linkages are shown in Table 2.

The RNAi constructs of the invention can readily be made using techniques known in the art, for example, using conventional nucleic acid solid phase synthesis. The polynucleotides of the RNAi constructs can be assembled on a suitable nucleic acid synthesizer utilizing standard nucleotide or nucleoside precursors (e.g. phosphoramidites). Automated nucleic acid synthesizers are sold commercially by several vendors, including DNA/RNA synthesizers from Applied Biosystems (Foster City, CA), MerMade synthesizers from BioAutomation (Irving, TX), and OligoPilot synthesizers from GE Healthcare Life Sciences (Pittsburgh, PA). An exemplary method for synthesizing the RNAi constructs of the invention is described in Example 1.

A 2' silyl protecting group can be used in conjunction with acid labile dimethoxytrityl (DMT) at the 5' position of ribonucleosides to synthesize oligonucleotides via phosphoramidite chemistry. Final deprotection conditions are known not to significantly degrade RNA products. All syntheses can be conducted in any automated or manual synthesizer on large, medium, or small scale. The syntheses may also be carried out in multiple well plates, columns, or glass slides.

The 2'-O-silyl group can be removed via exposure to fluoride ions, which can include any source of fluoride ion, e.g., those salts containing fluoride ion paired with inorganic counterions e.g., cesium fluoride and potassium fluoride or those salts containing fluoride ion paired with an organic counterion, e.g., a tetraalkylammonium fluoride. A crown ether catalyst can be utilized in combination with the inorganic fluoride in the deprotection reaction. Preferred fluoride ion sources are tetrabutylammonium fluoride or aminohydrofluorides (e.g., combining aqueous HF with triethylamine in a dipolar aprotic solvent, e.g., dimethylformamide).

The choice of protecting groups for use on the phosphite triesters and phosphotriesters can alter the stability of the triesters towards fluoride. Methyl protection of the phosphotriester or phosphitetriester can stabilize the linkage against fluoride ions and improve process yields.

Since ribonucleosides have a reactive 2' hydroxyl substituent, it can be desirable to protect the reactive 2' position in RNA with a protecting group that is orthogonal to a 5'-O-dimethoxytrityl protecting group, e.g., one stable to treatment with acid. Silyl protecting groups meet this criterion and can be readily removed in a final fluoride deprotection step that can result in minimal RNA degradation.

Tetrazole catalysts can be used in the standard phosphoramidite coupling reaction. Preferred catalysts include, e.g., tetrazole, S-ethyl-tetrazole, benzylthiotetrazole, p-nitrophenyltetrazole.

As can be appreciated by the skilled artisan, further methods of synthesizing the RNAi constructs described herein will be evident to those of ordinary skill in the art. Additionally, the various synthetic steps may be performed in an alternate sequence or order to give the desired compounds. Other synthetic chemistry transformations, protecting groups (e.g., for hydroxyl, amino, etc. present on the bases) and protecting group methodologies (protection and deprotection) useful in synthesizing the RNAi constructs described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. Custom synthesis of RNAi agents is also available from several commercial vendors, including Dharmacon, Inc. (Lafayette, CO), AxoLabs GmbH (Kulmbach, Germany), and Ambion, Inc. (Foster City, CA).

The RNAi constructs of the invention may comprise a ligand. As used herein, a "ligand" refers to any compound or molecule that is capable of interacting with another compound or molecule, directly or indirectly. The interaction of a ligand with another compound or molecule may elicit a biological response (e.g. initiate a signal transduction cascade, induce receptor-mediated endocytosis) or may just be a physical association. The ligand can modify one or more properties of the double-stranded RNA molecule to which is attached, such as the pharmacodynamic, pharmacokinetic, binding, absorption, cellular distribution, cellular uptake, charge and/or clearance properties of the RNA molecule.

The ligand may comprise a serum protein (e.g., human serum albumin, low-density lipoprotein, globulin), a cholesterol moiety, a vitamin (biotin, vitamin E, vitamin B12), a folate moiety, a steroid, a bile acid (e.g. cholic acid), a fatty acid (e.g., palmitic acid, myristic acid), a carbohydrate (e.g., a dextran, pullulan, chitin, chitosan, inulin, cyclodextrin or hyaluronic acid), a glycoside, a phospholipid, or antibody or binding fragment thereof (e.g. antibody or binding fragment that targets the RNAi construct to a specific cell type, such as liver). Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, O3-(oleoyl)lithocholic acid, O3-(oleoyl)cholenic acid, dimethoxytrityl, or phenoxazine), peptides (e.g., antennapedia peptide, Tat peptide, RGD peptides), alkylating agents, polymers, such as polyethylene glycol (PEG)(e.g., PEG-40K), polyamino acids, and polyamines (e.g. spermine, spermidine).

In certain embodiments, the ligands have endosomolytic properties. The endosomolytic ligands promote the lysis of the endosome and/or transport of the RNAi construct of the invention, or its components, from the endosome to the cytoplasm of the cell. The endosomolytic ligand may be a polycationic peptide or peptidomimetic, which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the RNAi construct of the invention, or its components, from the endosome to the cytoplasm of the cell. Exemplary endosomolytic ligands include the GALA peptide (Subbarao et al., Biochemistry, Vol. 26: 2964-2972, 1987), the EALA peptide (Vogel et al., J. Am. Chem. Soc., Vol. 118: 1581-1586, 1996), and their derivatives (Turk et al., Biochem. Biophys. Acta, Vol. 1559: 56-68, 2002). In one embodiment, the endosomolytic component may contain a chemical group (e.g., an amino acid) which will undergo a change in charge or protonation in response to a change in pH. The endosomolytic component may be linear or branched.

In some embodiments, the ligand comprises a lipid or other hydrophobic molecule. In one embodiment, the ligand comprises a cholesterol moiety or other steroid. Cholesterol-conjugated oligonucleotides have been reported to be more active than their unconjugated counterparts (Manoharan, Antisense Nucleic Acid Drug Development, Vol. 12: 103-228, 2002). Ligands comprising cholesterol moieties and other lipids for conjugation to nucleic acid molecules have also been described in U.S. Pat. Nos. 7,851,615; 7,745,608; and 7,833,992, all of which are hereby incorporated by reference in their entireties. In another embodiment, the ligand comprises a folate moiety. Polynucleotides conjugated to folate moieties can be taken up by cells via a receptor-mediated endocytosis pathway. Such folate-polynucleotide conjugates are described in U.S. Pat. No. 8,188,247, which is hereby incorporated by reference in its entirety.

The LPA gene is expressed predominantly in the liver. Thus, in certain embodiments, it is desirable to specifically deliver the RNAi constructs of the invention to liver cells. Accordingly, in certain embodiments, the ligand targets delivery of the RNAi construct specifically to liver cells (e.g. hepatocytes) using various approaches as described in more detail below. In certain embodiments, the RNAi constructs are targeted to liver cells with a ligand that binds to the surface-expressed asialoglycoprotein receptor (ASGR) or component thereof (e.g. ASGR1, ASGR2).

In some embodiments, RNAi constructs can be specifically targeted to the liver by employing ligands that bind to or interact with proteins expressed on the surface of liver cells. For example, in certain embodiments, the ligands may comprise antigen binding proteins (e.g. antibodies or binding fragments thereof (e.g. Fab, scFv)) that specifically bind to a receptor expressed on hepatocytes, such as the asialoglycoprotein receptor and the LDL receptor. In one particular embodiment, the ligand comprises an antibody or binding fragment thereof that specifically binds to ASGR1 and/or ASGR2. In another embodiment, the ligand comprises a Fab fragment of an antibody that specifically binds to ASGR1 and/or ASGR2. A "Fab fragment" is comprised of one immunoglobulin light chain (i.e. light chain variable region (VL) and constant region (CL)) and the $CH_1$ region and variable region (VH) of one immunoglobulin heavy chain. In another embodiment, the ligand comprises a single-chain variable antibody fragment (scFv fragment) of an antibody that specifically binds to ASGR1 and/or ASGR2. An "scFv fragment" comprises the VH and VL regions of an antibody, wherein these regions are present in a single polypeptide chain, and optionally comprising a peptide linker between the VH and VL regions that enables the Fv to form the desired structure for antigen binding. Exemplary antibodies and binding fragments thereof that specifically bind to ASGR1 that can be used as ligands for targeting the RNAi constructs of the invention to the liver are described in WIPO Publication No. WO 2017/058944, which is hereby incorporated by reference in its entirety. Other antibodies or binding fragments thereof that specifically bind to ASGR1, LDL receptor, or other liver surface-expressed proteins suitable for use as ligands in the RNAi constructs of the invention are commercially available.

In certain embodiments, the ligand comprises a carbohydrate. A "carbohydrate" refers to a compound made up of one or more monosaccharide units having at least 6 carbon atoms (which can be linear, branched or cyclic) with an oxygen, nitrogen or sulfur atom bonded to each carbon atom. Carbohydrates include, but are not limited to, the sugars (e.g., monosaccharides, disaccharides, trisaccharides, tetrasaccharides, and oligosaccharides containing from about 4, 5, 6, 7, 8, or 9 monosaccharide units), and polysaccharides, such as starches, glycogen, cellulose and polysaccharide gums. In some embodiments, the carbohydrate incorporated into the ligand is a monosaccharide selected from a pentose, hexose, or heptose and di- and tri-saccharides including such monosaccharide units. In other embodiments, the carbohydrate incorporated into the ligand is an amino sugar, such as galactosamine, glucosamine, N-acetylgalactosamine, and N-acetylglucosamine.

In some embodiments, the ligand comprises a hexose or hexosamine. The hexose may be selected from glucose, galactose, mannose, fucose, or fructose. The hexosamine may be selected from fructosamine, galactosamine, glucosamine, or mannosamine. In certain embodiments, the ligand comprises glucose, galactose, galactosamine, or glucosamine. In one embodiment, the ligand comprises glucose, glucosamine, or N-acetylglucosamine. In another embodiment, the ligand comprises galactose, galactosamine, or N-acetyl-galactosamine. In particular embodiments, the ligand comprises N-acetyl-galactosamine. Ligands comprising glucose, galactose, and N-acetyl-galactosamine (GalNAc) are particularly effective in targeting compounds to liver cells because such ligands bind to the ASGR expressed on the surface of hepatocytes. See, e.g., D'Souza and Devarajan, J. Control Release, Vol. 203: 126-139, 2015. Examples of GalNAc- or galactose-containing ligands that can be incorporated into the RNAi constructs of the invention are described in U.S. Pat. Nos. 7,491,805; 8,106,022; and 8,877,917; U.S. Patent Publication No. 20030130186; and WIPO Publication No. WO 2013166155, all of which are hereby incorporated by reference in their entireties.

In certain embodiments, the ligand comprises a multivalent carbohydrate moiety. As used herein, a "multivalent carbohydrate moiety" refers to a moiety comprising two or more carbohydrate units capable of independently binding or interacting with other molecules. For example, a multivalent carbohydrate moiety comprises two or more binding domains comprised of carbohydrates that can bind to two or more different molecules or two or more different sites on the same molecule. The valency of the carbohydrate moiety denotes the number of individual binding domains within the carbohydrate moiety. For instance, the terms "monovalent," "bivalent," "trivalent," and "tetravalent" with reference to the carbohydrate moiety refer to carbohydrate moieties with one, two, three, and four binding domains, respectively. The multivalent carbohydrate moiety may comprise a multivalent lactose moiety, a multivalent galactose moiety, a multivalent glucose moiety, a multivalent N-acetyl-galactosamine moiety, a multivalent N-acetyl-glucosamine moiety, a multivalent mannose moiety, or a multivalent fucose moiety. In some embodiments, the ligand comprises a multivalent galactose moiety. In other embodiments, the ligand comprises a multivalent N-acetyl-galactosamine moiety. In these and other embodiments, the multivalent carbohydrate moiety can be bivalent, trivalent, or tetravalent. In such embodiments, the multivalent carbohydrate moiety can be bi-antennary or tri-antennary. In one particular embodiment, the multivalent N-acetyl-galactosamine moiety is trivalent or tetravalent. In another particular embodiment, the multivalent galactose moiety is trivalent or tetravalent. Exemplary trivalent and tetravalent GalNAc-containing ligands for incorporation into the RNAi constructs of the invention are described in detail below.

The ligand can be attached or conjugated to the RNA molecule of the RNAi construct directly or indirectly. For instance, in some embodiments, the ligand is covalently attached directly to the sense or antisense strand of the RNAi construct. In other embodiments, the ligand is covalently attached via a linker to the sense or antisense strand of the RNAi construct. The ligand can be attached to nucleobases, sugar moieties, or internucleotide linkages of polynucleotides (e.g. sense strand or antisense strand) of the RNAi constructs of the invention. Conjugation or attachment to purine nucleobases or derivatives thereof can occur at any position including, endocyclic and exocyclic atoms. In certain embodiments, the 2-, 6-, 7-, or 8-positions of a purine nucleobase are attached to a ligand. Conjugation or attachment to pyrimidine nucleobases or derivatives thereof can also occur at any position. In some embodiments, the 2-, 5-, and 6-positions of a pyrimidine nucleobase can be attached to a ligand. Conjugation or attachment to sugar moieties of nucleotides can occur at any carbon atom. Exemplary carbon atoms of a sugar moiety that can be attached to a ligand include the 2', 3', and 5' carbon atoms. The 1' position can also be attached to a ligand, such as in an abasic nucleotide. Internucleotide linkages can also support ligand attachments. For phosphorus-containing linkages (e.g., phosphodiester, phosphorothioate, phosphorodithiotate, phosphoroamidate, and the like), the ligand can be attached directly to the phosphorus atom or to an O, N, or S atom bound to the phosphorus atom. For amine- or amide-containing internucleoside linkages (e.g., PNA), the ligand can be attached to the nitrogen atom of the amine or amide or to an adjacent carbon atom.

In some embodiments, the ligand may be attached to the 3' or 5' end of either the sense or antisense strand. In certain embodiments, the ligand is covalently attached to the 5' end of the sense strand. In such embodiments, the ligand is attached to the 5'-terminal nucleotide of the sense strand. In these and other embodiments, the ligand is attached at the 5'-position of the 5'-terminal nucleotide of the sense strand. In embodiments in which an inverted abasic nucleotide is the 5'-terminal nucleotide of the sense strand and linked to the adjacent nucleotide via a 5'-5' internucleotide linkage, the ligand can be attached at the 3'-position of the inverted abasic nucleotide. In other embodiments, the ligand is covalently attached to the 3' end of the sense strand. For example, in some embodiments, the ligand is attached to the 3'-terminal nucleotide of the sense strand. In certain such embodiments, the ligand is attached at the 3'-position of the 3'-terminal nucleotide of the sense strand. In embodiments in which an inverted abasic nucleotide is the 3'-terminal nucleotide of the sense strand and linked to the adjacent nucleotide via a 3'-3' internucleotide linkage, the ligand can be attached at the 5'-position of the inverted abasic nucleotide. In alternative embodiments, the ligand is attached near the 3' end of the sense strand, but before one or more terminal nucleotides (i.e. before 1, 2, 3, or 4 terminal nucleotides). In some embodiments, the ligand is attached at the 2'-position of the sugar of the 3'-terminal nucleotide of the sense strand. In other embodiments, the ligand is attached at the 2'-position of the sugar of the 5'-terminal nucleotide of the sense strand.

In certain embodiments, the ligand is attached to the sense or antisense strand via a linker. A "linker" is an atom or group of atoms that covalently joins a ligand to a polynucleotide component of the RNAi construct. The linker may be from about 1 to about 30 atoms in length, from about 2 to about 28 atoms in length, from about 3 to about 26 atoms in length, from about 4 to about 24 atoms in length, from about 6 to about 20 atoms in length, from about 7 to about 20 atoms in length, from about 8 to about 20 atoms in length, from about 8 to about 18 atoms in length, from about 10 to about 18 atoms in length, and from about 12 to about 18 atoms in length. In some embodiments, the linker may comprise a bifunctional linking moiety, which generally comprises an alkyl moiety with two functional groups. One of the functional groups is selected to bind to the compound of interest (e.g. sense or antisense strand of the RNAi construct) and the other is selected to bind essentially any selected group, such as a ligand as described herein. In certain embodiments, the linker comprises a chain structure or an oligomer of repeating units, such as ethylene glycol or amino acid units. Examples of functional groups that are typically employed in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Linkers that may be used to attach a ligand to the sense or antisense strand in the RNAi constructs of the invention include, but are not limited to, pyrrolidine, 8-amino-3,6-dioxaoctanoic acid, succinimidyl 4-(N-maleimidomethyl) cyclohexane-1-carboxylate, 6-aminohexanoic acid, substituted $C_1$-$C_{10}$ alkyl, substituted or unsubstituted $C_2$-$C_{10}$ alkenyl or substituted or unsubstituted $C_2$-$C_{10}$ alkynyl. Preferred substituent groups for such linkers include, but are not limited to, hydroxyl, amino, alkoxy, carboxy, benzyl, phenyl, nitro, thiol, thioalkoxy, halogen, alkyl, aryl, alkenyl and alkynyl.

In certain embodiments, the linkers are cleavable. A cleavable linker is one which is sufficiently stable outside the cell, but which upon entry into a target cell is cleaved to release the two parts the linker is holding together. In some embodiments, the cleavable linker is cleaved at least 10 times, 20 times, 30 times, 40 times, 50 times, 60 times, 70 times, 80 times, 90 times, or more, or at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linkers are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linker by reduction; esterases; endosomes or agents that can create an acidic environment, e.g., those that result in a pH of five or lower; enzymes that can hydrolyze or degrade an acid cleavable linker by acting as a general acid, peptidases (which can be substrate specific), and phosphatases.

A cleavable linker may comprise a moiety that is susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable group that is cleaved at a preferred pH, thereby releasing the RNA molecule from the ligand inside the cell, or into the desired compartment of the cell.

A linker can include a cleavable group that is cleavable by a particular enzyme. The type of cleavable group incorporated into a linker can depend on the cell to be targeted. For example, liver-targeting ligands can be linked to RNA molecules through a linker that includes an ester group. Liver cells are rich in esterases, and therefore the linker will be cleaved more efficiently in liver cells than in cell types that are not esterase-rich. Other types of cells rich in esterases include cells of the lung, renal cortex, and testis. Linkers that contain peptide bonds can be used when targeting cells rich in peptidases, such as liver cells and synoviocytes.

In general, the suitability of a candidate cleavable linker can be evaluated by testing the ability of a degradative agent (or condition) to cleave the candidate linker. It will also be desirable to also test the candidate cleavable linker for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In some embodiments, useful candidate linkers are cleaved at least 2, 4, 10, 20, 50, 70, or 100 times faster in the cell (or under in vitro conditions selected to mimic intracellular conditions) as compared to blood or serum (or under in vitro conditions selected to mimic extracellular conditions).

In other embodiments, redox cleavable linkers are utilized. Redox cleavable linkers are cleaved upon reduction or oxidation. An example of a reductively cleavable group is a disulfide linking group (—S—S—). To determine if a candidate cleavable linker is a suitable "reductively cleavable linker," or for example is suitable for use with a particular RNAi construct and particular ligand, one can use one or more methods described herein. For example, a candidate linker can be evaluated by incubation with dithiothreitol (DTT), or other reducing agent known in the art, which mimics the rate of cleavage that would be observed in a cell, e.g., a target cell. The candidate linkers can also be evaluated under conditions which are selected to mimic blood or serum conditions. In a specific embodiment, candidate linkers are cleaved by at most 10% in the blood. In other embodiments, useful candidate linkers are degraded at least 2, 4, 10, 20, 50, 70, or 100 times faster in the cell (or under in vitro conditions selected to mimic intracellular conditions) as compared to blood (or under in vitro conditions selected to mimic extracellular conditions).

In yet other embodiments, phosphate-based cleavable linkers, which are cleaved by agents that degrade or hydrolyze the phosphate group, are employed to covalently attach a ligand to the sense or antisense strand of the RNAi construct. An example of an agent that hydrolyzes phosphate groups in cells are enzymes, such as phosphatases in cells. Examples of phosphate-based cleavable groups are —O—P(O)(ORk)-O—, —O—P(S)(ORk)-O—, —O—P(S)(SRk)-O—, —S—P(O) (ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, and —O—P(S)(Rk)-S—, where Rk can be hydrogen or alkyl. Specific embodiments include —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—. Another specific embodiment is —O—P(O)(OH)—O—. These candidate linkers can be evaluated using methods analogous to those described above.

In other embodiments, the linkers may comprise acid cleavable groups, which are groups that are cleaved under acidic conditions. In some embodiments, acid cleavable groups are cleaved in an acidic environment with a pH of about 6.5 or lower (e.g., about 6.0, 5.5, 5.0, or lower), or by agents, such as enzymes that can act as a general acid. In a cell, specific low pH organelles, such as endosomes and lysosomes, can provide a cleaving environment for acid cleavable groups. Examples of acid cleavable linking groups include, but are not limited to, hydrazones, esters, and esters of amino acids. Acid cleavable groups can have the general formula —C═NN—, C(O)O, or —OC(O). A specific embodiment is when the carbon attached to the oxygen of the ester (the alkoxy group) is an aryl group, substituted alkyl group, or tertiary alkyl group such as dimethyl, pentyl or t-butyl. These candidates can be evaluated using methods analogous to those described above.

In other embodiments, the linkers may comprise ester-based cleavable groups, which are cleaved by enzymes, such as esterases and amidases in cells. Examples of ester-based cleavable groups include, but are not limited to, esters of alkylene, alkenylene and alkynylene groups. Ester cleavable groups have the general formula —C(O)O—, or —OC(O)—. These candidate linkers can be evaluated using methods analogous to those described above.

In further embodiments, the linkers may comprise peptide-based cleavable groups, which are cleaved by enzymes, such as peptidases and proteases in cells. Peptide-based cleavable groups are peptide bonds formed between amino acids to yield oligopeptides (e.g., dipeptides, tripeptides etc.) and polypeptides. Peptide-based cleavable groups include the amide group (—C(O)NH—). The amide group can be formed between any alkylene, alkenylene or alkynylene. A peptide bond is a special type of amide bond formed between amino acids to yield peptides and proteins. The peptide-based cleavage group is generally limited to the peptide bond (i.e., the amide bond) formed between amino acids yielding peptides and proteins. Peptide-based cleavable linking groups have the general formula —NHCHR$^A$C(O)NHCHR$^B$(O)—, where R$^A$ and R$^B$ are the side chains of the two adjacent amino acids. These candidates can be evaluated using methods analogous to those described above.

Other types of linkers suitable for attaching ligands to the sense or antisense strands in the RNAi constructs of the invention are known in the art and can include the linkers described in U.S. Pat. Nos. 7,723,509; 8,017,762; 8,828,956; 8,877,917; and 9,181,551, all of which are hereby incorporated by reference in their entireties.

In certain embodiments, the ligand covalently attached to the sense or antisense strand of the RNAi constructs of the invention comprises a GalNAc moiety, e.g, a multivalent GalNAc moiety. In some embodiments, the multivalent GalNAc moiety is a trivalent GalNAc moiety and is attached to the 3' end of the sense strand. In other embodiments, the multivalent GalNAc moiety is a trivalent GalNAc moiety and is attached to the 5' end of the sense strand. In yet other embodiments, the multivalent GalNAc moiety is a tetravalent GalNAc moiety and is attached to the 3' end of the sense strand. In still other embodiments, the multivalent GalNAc moiety is a tetravalent GalNAc moiety and is attached to the 5' end of the sense strand.

In certain embodiments, the RNAi constructs of the invention comprise a ligand having the structure of Structure 1:

[Structure 1]

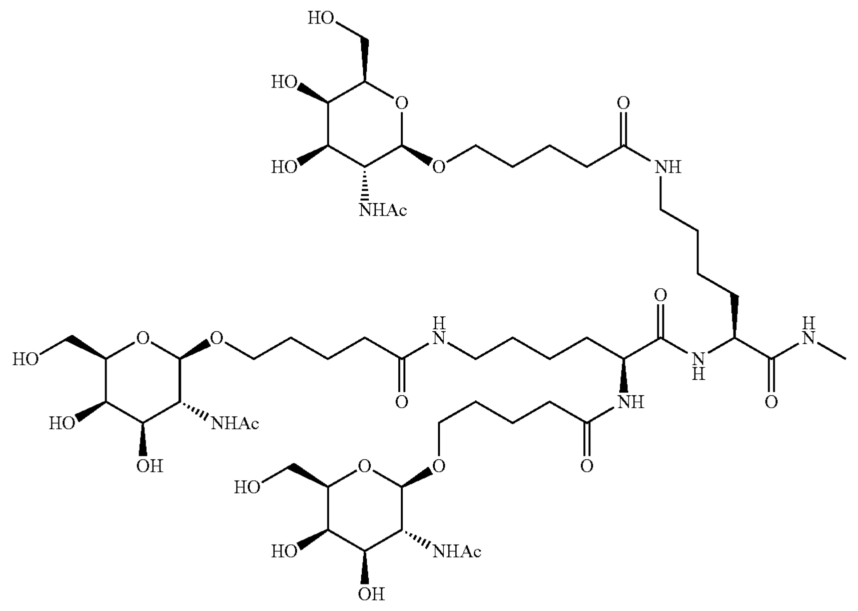

In preferred embodiments, the ligand having this structure is covalently attached to the 5' end of the sense strand via a linker, such as the linkers described herein. In one embodiment, the linker is an aminohexyl linker.

Exemplary trivalent and tetravalent GalNAc moieties and linkers that can be attached to the double-stranded RNA molecules in the RNAi constructs of the invention are provided in the structural formulas I-IX below. "Ac" in the formulas listed herein represents an acetyl group.

In one embodiment, the RNAi construct comprises a ligand and linker having the following structure of Formula I, wherein each n is independently 1 to 3, k is 1 to 3, m is 1 or 2, j is 1 or 2, and the ligand is attached to the 3' end of the sense strand of the double-stranded RNA molecule (represented by the solid wavy line):

FORMULA I

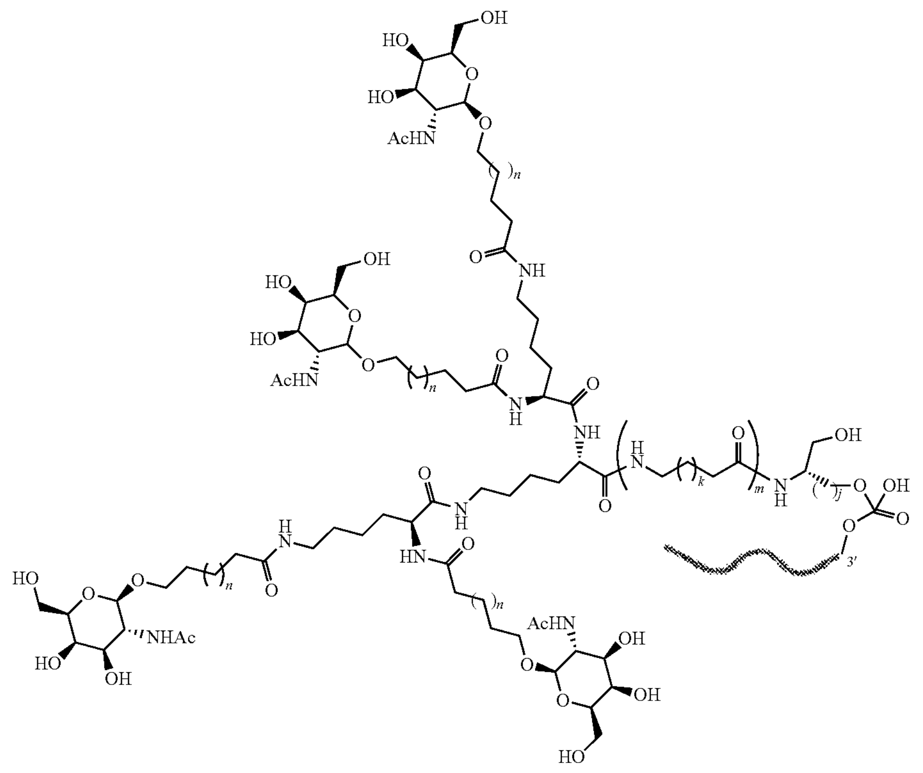

In another embodiment, the RNAi construct comprises a ligand and linker having the following structure of Formula II, wherein each n is independently 1 to 3, k is 1 to 3, m is 1 or 2, j is 1 or 2, and the ligand is attached to the 3' end of the sense strand of the double-stranded RNA molecule (represented by the solid wavy line):

In yet another embodiment, the RNAi construct comprises a ligand and linker having the following structure of Formula III, wherein the ligand is attached to the 3' end of the sense strand of the double-stranded RNA molecule (represented by the solid wavy line):

FORMULA II

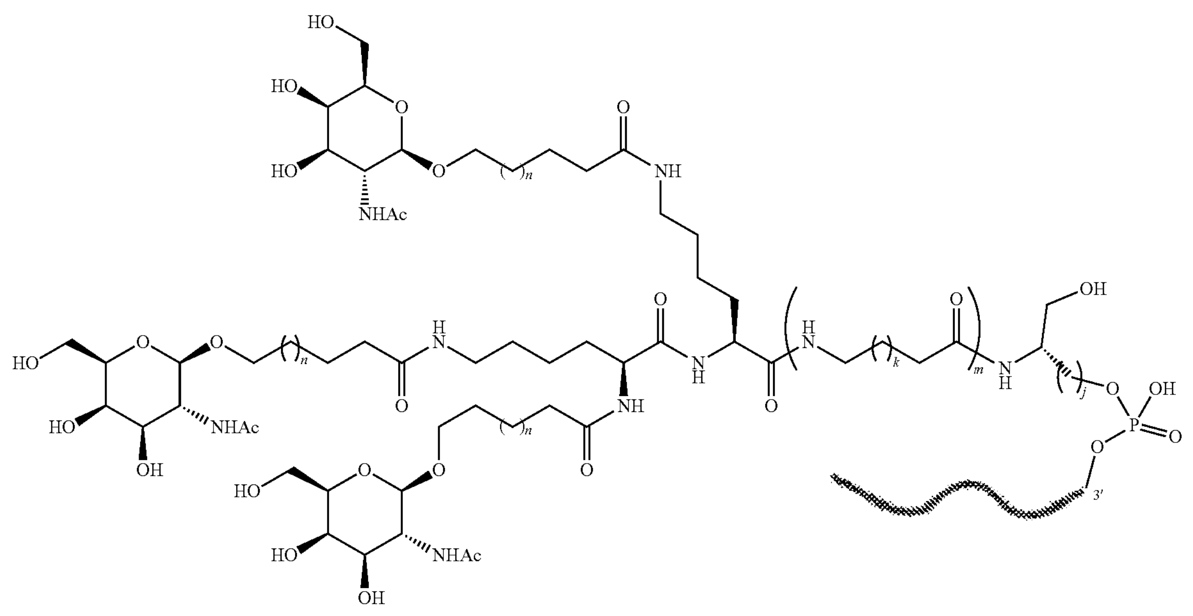

FORMULA III

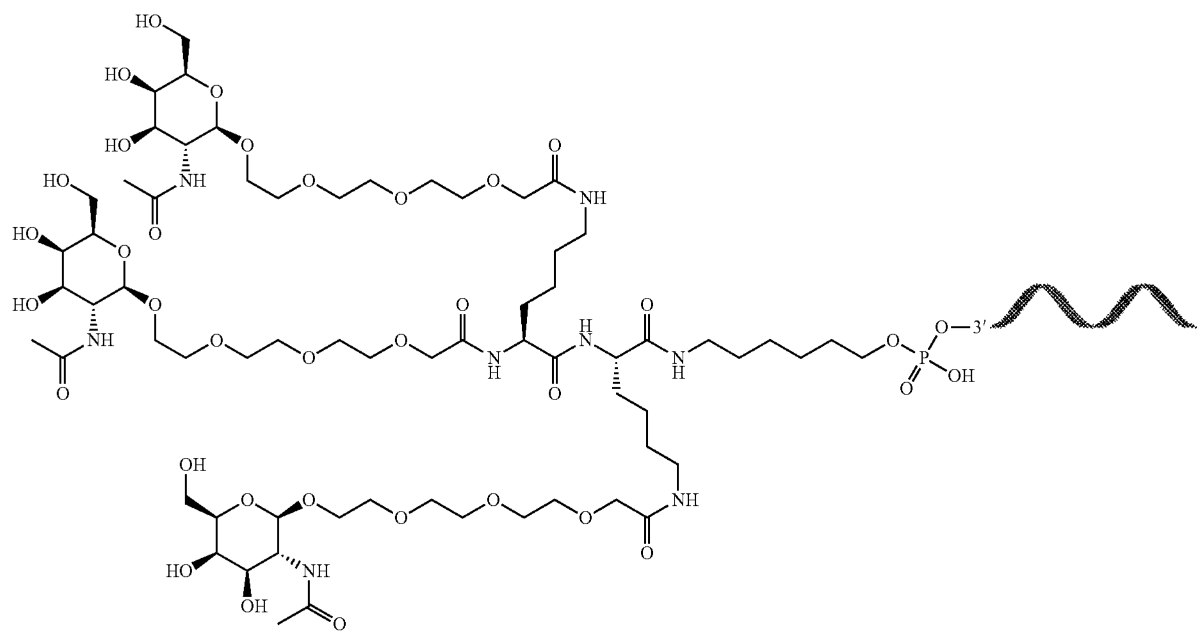

In still another embodiment, the RNAi construct comprises a ligand and linker having the following structure of Formula IV, wherein the ligand is attached to the 3' end of the sense strand of the double-stranded RNA molecule (represented by the solid wavy line):

FORMULA IV

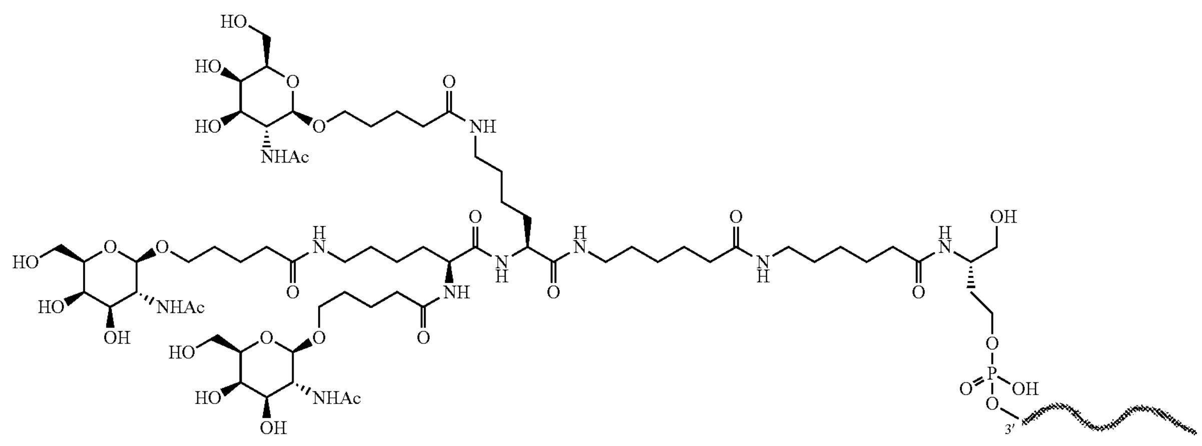

In certain embodiments, the RNAi construct comprises a ligand and linker having the following structure of Formula V, wherein each n is independently 1 to 3, k is 1 to 3, and the ligand is attached to the 5' end of the sense strand of the double-stranded RNA molecule (represented by the solid wavy line):

FORMULA V

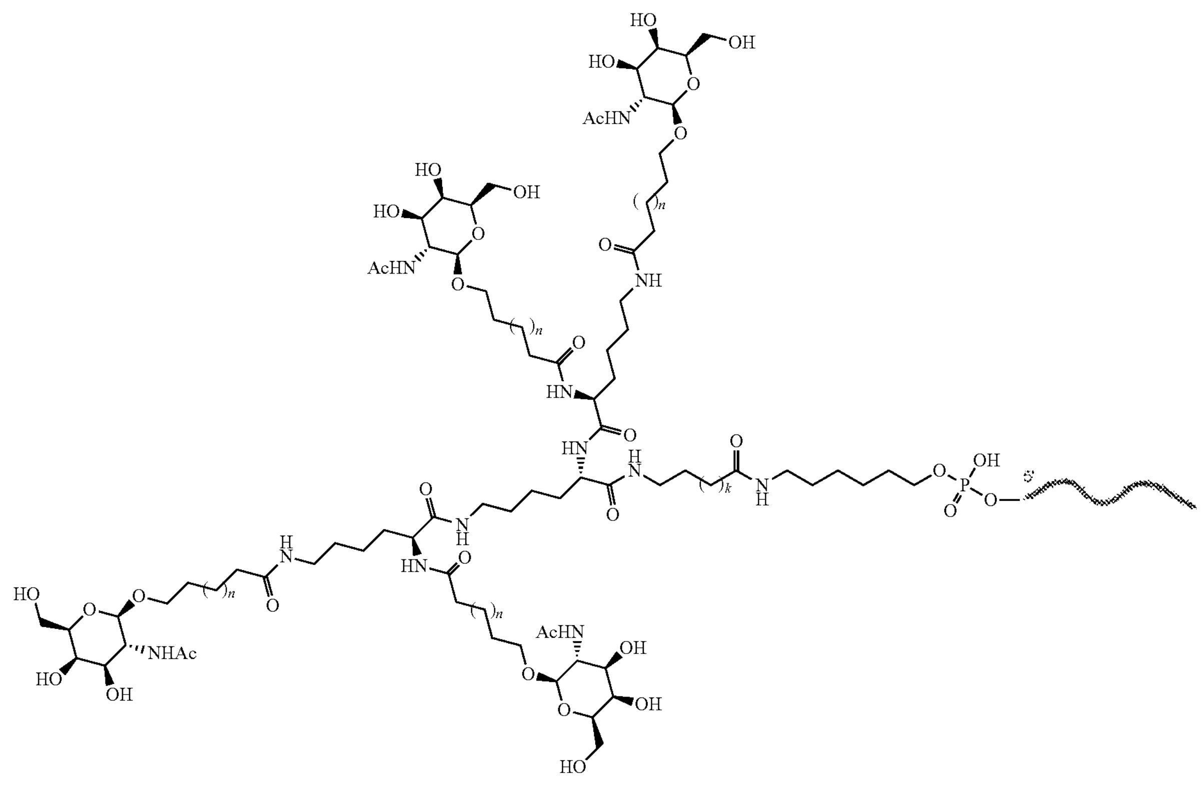

In other embodiments, the RNAi construct comprises a ligand and linker having the following structure of Formula VI, wherein each n is independently 1 to 3, k is 1 to 3, and the ligand is attached to the 5' end of the sense strand of the double-stranded RNA molecule (represented by the solid wavy line):

FORMULA VI

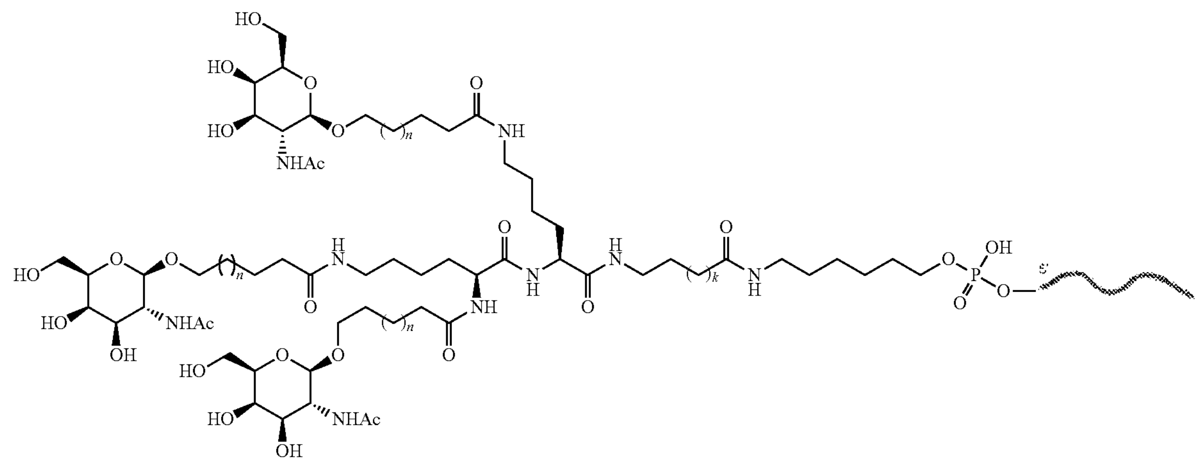

In one particular embodiment, the RNAi construct comprises a ligand and linker having the following structure of Formula VII, wherein X=O or S and wherein the ligand is attached to the 5' end of the sense strand of the double-stranded RNA molecule (represented by the squiggly line):

FORMULA VII

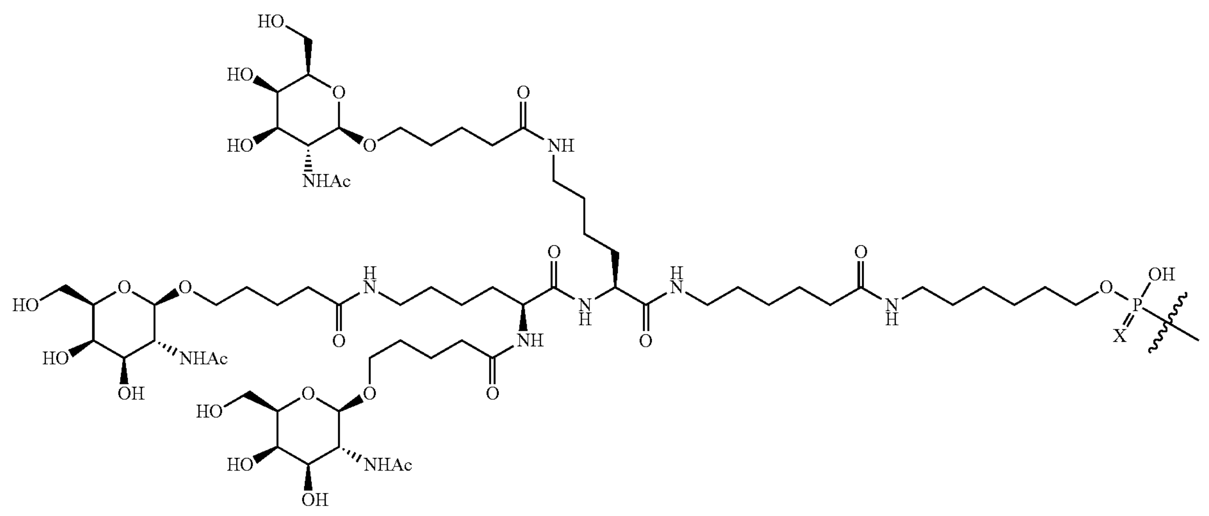

In some embodiments, the RNAi construct comprises a ligand and linker having the following structure of Formula VIII, wherein each n is independently 1 to 3 and the ligand is attached to the 5' end of the sense strand of the double-stranded RNA molecule (represented by the solid wavy line):

FORMULA VIII

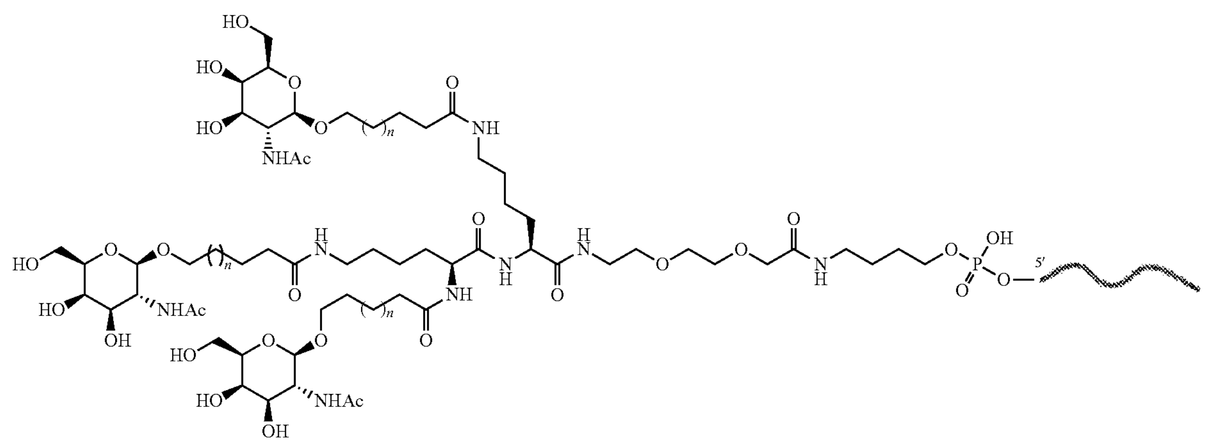

In certain embodiments, the RNAi construct comprises a ligand and linker having the following structure of Formula IX, wherein the ligand is attached to the 5' end of the sense strand of the double-stranded RNA molecule (represented by the solid wavy line):

FORMULA IX

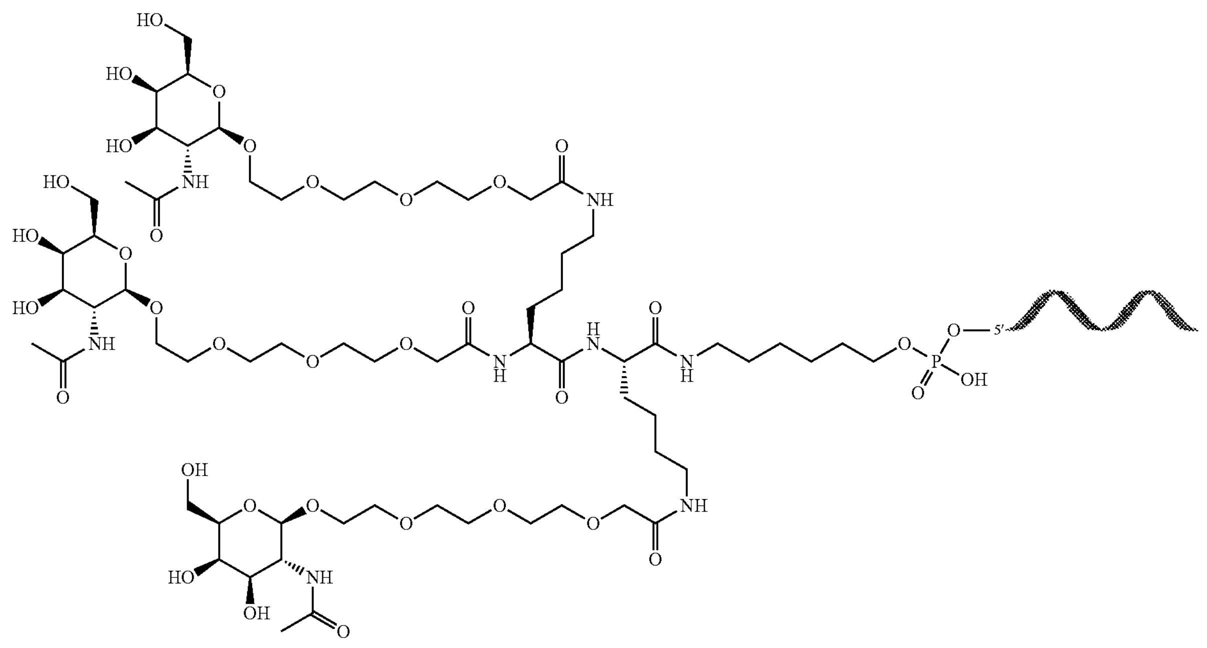

A phosphorothioate bond can be substituted for the phosphodiester bond shown in any one of Formulas I-IX to covalently attach the ligand and linker to the nucleic acid strand.

The present invention also includes pharmaceutical compositions and formulations comprising the RNAi constructs described herein and pharmaceutically acceptable carriers, excipients, or diluents. Such compositions and formulations are useful for reducing expression of the LPA gene in a patient in need thereof. Where clinical applications are contemplated, pharmaceutical compositions and formulations will be prepared in a form appropriate for the intended application. Generally, this will entail preparing compositions that are essentially free of pyrogens, as well as other impurities that could be harmful to humans or animals.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier, excipient, or diluent" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the RNAi constructs of the present invention, its use in therapeutic compositions is contemplated. Supplementary active ingredients also can be incorporated into the compositions, provided they do not inactivate the RNAi constructs of the compositions.

Compositions and methods for the formulation of pharmaceutical compositions depend on a number of criteria, including, but not limited to, route of administration, type and extent of disease or disorder to be treated, or dose to be administered. In some embodiments, the pharmaceutical compositions are formulated based on the intended route of delivery. For instance, in certain embodiments, the pharmaceutical compositions are formulated for parenteral delivery. Parenteral forms of delivery include intravenous, intraarterial, subcutaneous, intrathecal, intraperitoneal or intramuscular injection or infusion. In one embodiment, the pharmaceutical composition is formulated for intravenous delivery. In such an embodiment, the pharmaceutical composition may include a lipid-based delivery vehicle. In another embodiment, the pharmaceutical composition is formulated for subcutaneous delivery. In such an embodiment, the pharmaceutical composition may include a targeting ligand (e.g. GalNAc-containing or antibody-containing ligands described herein).

In some embodiments, the pharmaceutical compositions comprise an effective amount of an RNAi construct described herein. An "effective amount" is an amount sufficient to produce a beneficial or desired clinical result. In some embodiments, an effective amount is an amount sufficient to reduce LPA gene expression in a particular tissue or cell-type (e.g. liver or hepatocytes) of a patient. An effective amount of an RNAi construct of the invention may be from about 0.01 mg/kg body weight to about 100 mg/kg body weight, and may be administered daily, weekly, monthly, or at longer intervals. The precise determination of what would be considered an effective amount and frequency of administration may be based on several factors, including a patient's size, age, and general condition, type of disorder to be treated (e.g. myocardial infarction, coronary artery disease, peripheral artery disease, stroke), particular RNAi construct employed, and route of administration.

Administration of the pharmaceutical compositions of the present invention may be via any common route so long as the target tissue is available via that route. Such routes include, but are not limited to, parenteral (e.g., subcutaneous, intramuscular, intraperitoneal or intravenous), oral, nasal, buccal, intradermal, transdermal, and sublingual routes, or by direct injection into liver tissue or delivery through the hepatic portal vein. In some embodiments, the pharmaceutical composition is administered parenterally. For instance, in certain embodiments, the pharmaceutical composition is administered intravenously. In other embodiments, the pharmaceutical composition is administered subcutaneously.

Colloidal dispersion systems, such as macromolecule complexes, nanocapsules, microspheres, beads, and lipid-based systems, including oil-in-water emulsions, micelles, mixed micelles, and liposomes, may be used as delivery vehicles for the RNAi constructs of the invention. Commercially available fat emulsions that are suitable for delivering the nucleic acids of the invention include Intralipid® (Baxter International Inc.), Liposyn® (Abbott Pharmaceuticals), Liposyn®II (Hospira), Liposyn®III (Hospira), Nutrilipid (B. Braun Medical Inc.), and other similar lipid emulsions. A preferred colloidal system for use as a delivery vehicle in vivo is a liposome (i.e., an artificial membrane vesicle). The RNAi constructs of the invention may be encapsulated within liposomes or may form complexes thereto, in particular to cationic liposomes. Alternatively, RNAi constructs of the invention may be complexed to lipids, in particular to cationic lipids. Suitable lipids and liposomes include neutral (e.g., dioleoylphosphatidyl ethanolamine (DOPE), dimyristoylphosphatidyl choline (DMPC), and dipalmitoyl phosphatidylcholine (DPPC)), distearolyphosphatidyl choline), negative (e.g., dimyristoylphosphatidyl glycerol (DMPG)), and cationic (e.g., dioleoyltetramethylaminopropyl (DOTAP) and dioleoylphosphatidyl ethanolamine (DOTMA)). The preparation and use of such colloidal dispersion systems are well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449.

In some embodiments, the RNAi constructs of the invention are fully encapsulated in a lipid formulation, e.g., to form a SNALP or other nucleic acid-lipid particle. As used herein, the term "SNALP" refers to a stable nucleic acid-lipid particle. SNALPs typically contain a cationic lipid, a non-cationic lipid, and a lipid that prevents aggregation of the particle (e.g., a PEG-lipid conjugate). SNALPs are exceptionally useful for systemic applications, as they exhibit extended circulation lifetimes following intravenous injection and accumulate at distal sites (e.g., sites physically separated from the administration site). The nucleic acid-lipid particles typically have a mean diameter of about 50 nm to about 150 nm, about 60 nm to about 130 nm, about 70 nm to about 110 nm, or about 70 nm to about 90 nm, and are substantially nontoxic. In addition, the nucleic acids when present in the nucleic acid-lipid particles are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

The pharmaceutical compositions suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with free amino groups) derived from inorganic acids (e.g., hydrochloric or phosphoric acids), or from organic acids (e.g., acetic, oxalic, tartaric, mandelic, and the like). Salts formed with the free carboxyl groups can also be derived from inorganic bases (e.g., sodium, potassium, ammonium, calcium, or ferric hydroxides) or from organic bases (e.g., isopropylamine, trimethylamine, histidine, procaine and the like). In some embodiments, the RNAi constructs of the invention are formulated as a sodium salt.

For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). For human administration, preparations should meet sterility, pyrogenicity, general safety and purity standards as required by FDA standards. In certain embodiments, a pharmaceutical composition of the invention comprises or consists of a sterile saline solution and an RNAi construct described herein. In other embodiments, a pharmaceutical composition of the invention comprises or consists of an RNAi construct described herein and sterile water (e.g. water for injection, WFI). In still other embodiments, a pharmaceutical composition of the invention comprises or consists of an RNAi construct described herein and phosphate-buffered saline (PBS).

In some embodiments, the pharmaceutical compositions of the invention are packaged with or stored within a device for administration. Devices for injectable formulations include, but are not limited to, injection ports, pre-filled syringes, autoinjectors, injection pumps, on-body injectors, and injection pens. Devices for aerosolized or powder formulations include, but are not limited to, inhalers, insufflators, aspirators, and the like. Thus, the present invention includes administration devices comprising a pharmaceutical composition of the invention for treating or preventing one or more of the diseases or disorders described herein.

The present invention provides a method for reducing or inhibiting expression of the LPA gene, and thus the production of apo(a) protein, in a cell (e.g. liver cell) by contacting the cell with any one of the RNAi constructs described herein. The cell may be in vitro or in vivo. LPA gene expression can be assessed by measuring the amount or level of LPA mRNA, apo(a) protein, or another biomarker linked to LPA expression, such as serum levels of Lp(a). The reduction of LPA expression in cells or animals treated with an RNAi construct of the invention can be determined relative to the LPA expression in cells or animals not treated with the RNAi construct or treated with a control RNAi construct. For instance, in some embodiments, reduction of LPA expression is assessed by (a) measuring the amount or level of LPA mRNA in liver cells treated with a RNAi construct of the invention, (b) measuring the amount or level of LPA mRNA in liver cells treated with a control RNAi construct (e.g. RNAi construct directed to an RNA molecule not expressed in liver cells or a RNAi construct having a nonsense or scrambled sequence) or no construct, and (c) comparing the measured LPA mRNA levels from treated cells in (a) to the measured LPA mRNA levels from control cells in (b). The LPA mRNA levels in the treated cells and controls cells can be normalized to RNA levels for a control gene (e.g. 18S ribosomal RNA or housekeeping gene) prior to comparison. LPA mRNA levels can be measured by a variety of methods, including Northern blot analysis, nuclease protection assays, fluorescence in situ hybridization (FISH), reverse-transcriptase (RT)-PCR, real-time RT-PCR, quantitative PCR, droplet digital PCR, and the like.

In other embodiments, reduction of LPA expression is assessed by (a) measuring the amount or level of apo(a) protein in liver cells treated with a RNAi construct of the invention, (b) measuring the amount or level of apo(a) protein in liver cells treated with a control RNAi construct (e.g. RNAi construct directed to a RNA molecule not expressed in liver cells or a RNAi construct having a nonsense or scrambled sequence) or no construct, and (c) comparing the measured apo(a) protein levels from treated cells in (a) to the measured apo(a) protein levels from control cells in (b). Methods of measuring apo(a) protein levels are known to those of skill in the art, and include Western Blots, immunoassays (e.g. ELISA), and flow cytometry. Any method capable of measuring LPA mRNA or apo(a) protein can be used to assess the efficacy of the RNAi constructs of the invention.

In some embodiments, the methods to assess LPA expression levels are performed in vitro in cells that natively express the LPA gene (e.g. liver cells) or cells that have been engineered to express the LPA gene. In certain embodiments, the methods are performed in vitro in liver cells. Suitable liver cells include, but are not limited to, primary hepatocytes (e.g. human or non-human primate hepatocytes), HepAD38 cells, HuH-6 cells, HuH-7 cells, HuH-5-2 cells, BNLCL2 cells, Hep3B cells, or HepG2 cells. In one embodiment, the liver cells are HuH-7 cells. In another embodiment, the liver cells are human primary hepatocytes.

In other embodiments, the methods to assess LPA expression levels are performed in vivo. The RNAi constructs and any control RNAi constructs can be administered to an animal (e.g. transgenic animal expressing an LPA gene or non-human primate) and LPA mRNA or apo(a) protein levels assessed in liver tissue harvested from the animal following treatment. Alternatively or additionally, a biomarker or functional phenotype associated with LPA expression can be assessed in the treated animals. For instance, apo(a) protein is a primary component of Lp(a) present in the serum or plasma. Thus, serum or plasma levels of Lp(a) can be measured in animals treated with RNAi constructs of the invention to assess the functional efficacy of reducing LPA expression. Exemplary methods for measuring serum or plasma Lp(a) levels are described in Examples 3 and 4.

In certain embodiments, expression of LPA is reduced in liver cells by at least 40%, at least 45%, or at least 50% by an RNAi construct of the invention. In some embodiments, expression of LPA is reduced in liver cells by at least 60%, at least 65%, at least 70%, at least 75%, at least 80%, or at least 85% by an RNAi construct of the invention. In other embodiments, the expression of LPA is reduced in liver cells by about 90% or more, e.g., 91%, 92%, 93%, 94%, 95%, 96%, 97%, 98%, 99%, or more by an RNAi construct of the invention. The percent reduction of LPA expression can be measured by any of the methods described herein as well as others known in the art.

The present invention provides methods for reducing or inhibiting expression of the LPA gene, and thus the production of apo(a) protein, in a patient in need thereof as well as methods of treating or preventing conditions, diseases, or disorders associated with LPA expression or apo(a) activity. A "condition, disease, or disorder associated with LPA expression" refers to conditions, diseases, or disorders in which LPA expression levels are altered or where elevated expression levels of LPA are associated with an increased risk of developing the condition, disease or disorder. A condition, disease, or disorder associated with LPA expression can also include conditions, diseases, or disorders resulting from aberrant changes in lipoprotein metabolism, such as changes resulting in abnormal or elevated levels of Lp(a), cholesterol, lipids, triglycerides, etc. or impaired clearance of these molecules. Apo(a) protein is a primary component of Lp(a) and elevated levels of Lp(a) have been associated with increased risk of cardiovascular disease (see, e.g., Nordestgaard et al., Eur. Heart J., Vol. 31: 2844-2853, 2010; Kronenberg and Utermann, J. Intern. Med., Vol. 273:6-30, 2013; Nordestgaard et al., J. Lipid Res., Vol. 57:1953-1975, 2016; and Tsimikas, J. Am. Coll. Cardiol., Vol. 69:692-711, 2017). Thus, in certain embodiments, the RNAi constructs of the invention are particularly useful for treating or preventing cardiovascular disease (e.g. coronary artery disease and myocardial infarction) and reducing circulating levels of Lp(a).

Conditions, diseases, and disorders associated with LPA expression that can be treated or prevented according to the methods of the invention include, but are not limited to, cardiovascular disease, such as myocardial infarction, heart failure, stroke (ischemic and hemorrhagic), atherosclerosis, coronary artery disease, peripheral vascular disease (e.g. peripheral artery disease), cerebrovascular disease, vulnerable plaque, and aortic valve stenosis; familial hypercholesterolemia; venous thrombosis; hypercholesterolemia; hyperlipidemia; and dyslipidemia.

In certain embodiments, the present invention provides a method for reducing the expression of LPA in a patient in need thereof comprising administering to the patient any of the RNAi constructs described herein. The term "patient," as used herein, refers to a mammal, including humans, and can be used interchangeably with the term "subject." Preferably, the expression level of LPA in hepatocytes in the patient is reduced following administration of the RNAi construct as compared to the LPA expression level in a patient not receiving the RNAi construct or as compared to the LPA expression level in the patient prior to administration of the RNAi construct. In some embodiments, following administration of an RNAi construct of the invention, expression of LPA is reduced in the patient by at least 30%, at least 35%, at least 40%, at least 45%, at least 50%, at least 55%, at least 60%, at least 65%, at least 70%, at least 75%, at least 80%, at least 85%, or at least 90%, e.g., 91%, 92%, 93%, 94%, 95%, 96%, 97%, 98%, or 99%. The percent reduction of LPA expression can be measured by any of the methods described herein as well as others known in the art. In certain embodiments, the percent reduction of LPA expression is determined by assessing Lp(a) levels in the serum or plasma of the patient according to methods described herein.

In some embodiments, a patient in need of reduction of LPA expression is a patient who is at risk of having a myocardial infarction. A patient who is at risk of having a myocardial infarction may be a patient who has a history of myocardial infarction (e.g. has had a previous myocardial infarction). A patient at risk of having a myocardial infarction may also be a patient who has a familial history of myocardial infarction or who has one or more risk factors of myocardial infarction. Such risk factors include, but are not limited to, hypertension, elevated levels of non-HDL cholesterol, elevated levels of triglycerides, diabetes, obesity, or history of autoimmune diseases (e.g. rheumatoid arthritis, lupus). In one embodiment, a patient who is at risk of having a myocardial infarction is a patient who has or is diagnosed with coronary artery disease. The risk of myocardial infarction in these and other patients can be reduced by administering to the patients any of the RNAi constructs described herein. Accordingly, the present invention provides a method for reducing the risk of myocardial infarction in a patient in need thereof comprising administering to the patient an RNAi construct described herein. In some embodiments, the present invention includes use of any of the RNAi constructs described herein in the preparation of a medicament for reducing the risk of myocardial infarction in a patient in need thereof. In other embodiments, the present invention provides an LPA-targeting RNAi construct for use in a method for reducing the risk of myocardial infarction in a patient in need thereof.

In certain embodiments, a patient in need of reduction of LPA expression is a patient who is diagnosed with or at risk of cardiovascular disease. Thus, the present invention includes a method for treating or preventing cardiovascular disease in a patient in need thereof by administering any of the RNAi constructs of the invention. In some embodiments, the present invention includes use of any of the RNAi constructs described herein in the preparation of a medicament for treating or preventing cardiovascular disease in a patient in need thereof. In other embodiments, the present invention provides an LPA-targeting RNAi construct for use in a method for treating or preventing cardiovascular disease in a patient in need thereof. Cardiovascular disease includes, but is not limited to, myocardial infarction, heart failure, stroke (ischemic and hemorrhagic), atherosclerosis, coronary artery disease, peripheral vascular disease (e.g. peripheral artery disease), cerebrovascular disease, vulnerable plaque, and aortic valve stenosis. In some embodiments, the cardiovascular disease to be treated or prevented according to the methods of the invention is coronary artery disease. In other embodiments, the cardiovascular disease to be treated or prevented according to the methods of the invention is myocardial infarction. In yet other embodiments, the cardiovascular disease to be treated or prevented according to the methods of the invention is stroke. In still other embodiments, the cardiovascular disease to be treated or prevented according to the methods of the invention is peripheral artery disease. In certain embodiments, administration of the RNAi constructs described herein reduces the risk of non-fatal myocardial infarctions, fatal and non-fatal strokes, certain types of heart surgery (e.g. angioplasty, bypass), hospitalization for heart failure, chest pain in patients with heart disease, and/or cardiovascular events in patients with established heart disease (e.g. prior myocardial infarction, prior heart surgery, and/or chest pain with evidence of blocked arteries). In some embodiments, administration of the RNAi constructs described herein according to the methods of the invention can be used to reduce the risk of recurrent cardiovascular events.

In certain other embodiments, a patient in need of reduction of LPA expression is a patient who has elevated levels of circulating Lp(a). Accordingly, in some embodiments, the present invention provides a method for reducing Lp(a) serum or plasma levels in a patient in need thereof by administering to the patient any of the RNAi constructs described herein. In some embodiments, the present invention includes use of any of the RNAi constructs described herein in the preparation of a medicament for reducing Lp(a) serum or plasma levels in a patient in need thereof. In other embodiments, the present invention provides an LPA-targeting RNAi construct for use in a method for reducing Lp(a) serum or plasma levels in a patient in need thereof. As described above, elevated levels of circulating Lp(a) are associated with an increased risk of cardiovascular disease. In some embodiments, Lp(a) levels in serum or plasma are reduced in the patient following administration of the RNAi construct as compared to the Lp(a) levels in serum or plasma in the patient prior to administration of the RNAi construct or as compared to the Lp(a) levels in serum or plasma in a patient not receiving the RNAi construct. In certain embodiments, following administration of an RNAi construct of the invention, Lp(a) levels in serum or plasma are reduced in the patient to about 150 nmol/L or less, about 125 nmol/L or less, about 100 nmol/L or less, about 75 nmol/L or less, about 70 nmol/L or less, about 65 nmol/L or less, about 60 nmol/L or less, about 55 nmol/L or less, about 50 nmol/L, about 45 nmol/L or less, about 40 nmol/L or less, about 35 nmol/L or less, or about 30 nmol/L or less. Although there is a preference to measure Lp(a) levels in units of particle concentration (e.g. nmol/L)(see, e.g., Wilson et al., Journal of Clinical Lipidology, Vol. 13: 374-392, 2019), Lp(a) levels may be measured in units of mass concentration (e.g. mg/dL). In such embodiments, an RNAi construct of the invention may reduce Lp(a) levels in serum or plasma in the patient to about 100 mg/dL or less, about 90 mg/dL or less, about 80 mg/dL or less, about 70 mg/dL or less, about 60 mg/dL or less, about 50 mg/dL or less, about 45 mg/dL or less, about 40 mg/dL or less, about 35 mg/dL or less, about 30 mg/dL or less, about 25 mg/dL or less, about 20 mg/dL or less, or about 15 mg/dL or less following administration. Lp(a) levels can be measured in plasma or serum samples using commercially available kits, such as the Lp(a) ELISA assay kit from Mercodia AB (Uppsala, Sweden), the Lp(a) immunoturbidimetric assay from Randox Laboratories Ltd. (Crumlin, United Kingdom), or the Tina-quant® Lp(a) assay from F. Hoffmann-La Roche Ltd. (Basel, Switzerland), or using other methods known in the art, such as those described Marcovina and Albers, J. Lipid Res., Vol. 57:526-537, 2016.

In some embodiments, a patient to be treated according to the methods of the invention is a patient who has elevated circulating levels of Lp(a) (e.g. elevated serum or plasma levels of Lp(a)). A patient to be treated according to the methods of the invention may have circulating Lp(a) levels of about 50 nmol/L or greater, about 55 nmol/L or greater, about 60 nmol/L or greater, about 65 nmol/L or greater, about 70 nmol/L or greater, about 75 nmol/L or greater, about 100 nmol/L or greater, about 125 nmol/L or greater, about 150 nmol/L or greater, about 175 nmol/L or greater, or about 200 nmol/L or greater. In certain embodiments, a patient is administered an RNAi construct of the invention if the patient has a serum or plasma Lp(a) level of about 100 nmol/L or greater. In one embodiment, a patient is administered an RNAi construct of the invention if the patient has a serum or plasma Lp(a) level of about 125 nmol/L or greater. In another embodiment, a patient is administered an RNAi construct of the invention if the patient has a serum or plasma Lp(a) level of about 150 nmol/L or greater. In embodiments in which circulating Lp(a) levels are measured in mass concentration units, a patient to be treated according to the methods of the invention may have circulating Lp(a) levels of about 30 mg/dL or greater, about 35 mg/dL or greater, about 40 mg/dL or greater, about 45 mg/dL or greater, about 50 mg/dL or greater, about 55 mg/dL or greater, about 60 mg/dL or greater, about 65 mg/dL or greater, about 70 mg/dL or greater, about 75 mg/dL or greater, or about 100 mg/dL or greater. In one embodiment, a patient is administered an RNAi construct of the invention if the patient has a serum or plasma Lp(a) level of about 50 mg/dL or greater. In another embodiment, a patient is administered an RNAi construct of the invention if the patient has a serum or plasma Lp(a) level of about 70 mg/dL or greater.

In certain embodiments, a patient to be treated according to the methods of the invention is a patient who has a vulnerable plaque (also referred to as unstable plaque). Vulnerable plaques are a build-up of macrophages and lipids containing predominantly cholesterol that lie underneath the endothelial lining of the arterial wall. These vulnerable plaques can rupture resulting in the formation of a blood clot, which can potentially block blood flow through the artery and cause a myocardial infarction or stroke. Vulnerable plaques can be identified by methods known in the art, including, but not limited to, intravascular ultrasound and computed tomography (Sahara et al., European Heart Journal, Vol. 25: 2026-2033, 2004; Budhoff, J. Am. Coll. Cardiol., Vol. 48: 319-321, 2006; Hausleiter et al., J. Am. Coll. Cardiol., Vol. 48: 312-318, 2006).

The following examples, including the experiments conducted and the results achieved, are provided for illustrative purposes only and are not to be construed as limiting the scope of the appended claims.

EXAMPLES

Example 1. Design and Synthesis of LPA RNAi Constructs

Candidate sequences for the design of therapeutic siRNA molecules targeting the human LPA gene were identified using a bioinformatics analysis of the human LPA transcript, the sequence of which is provided herein as SEQ ID NO: 1 (NCBI Reference Sequence No. NM_005577.4; see FIG. 1). The human LPA gene is highly polymorphic with alleles of the gene differing in numbers of repeats of the kringle IV-2 (KIV-2) domain among individuals. KIV-2 domain repeats can range from 2 to 43 copies among individuals. The transcript provided herein as SEQ ID NO: 1 is from an allelic variant containing 15 copies of the KIV-2 domain. Sequences were analyzed using an in-house siRNA design algorithm and selected if certain criteria were met. Sequences were also evaluated for cross-reactivity with the LPA gene from cynomolgus monkeys (NCBI Reference Sequence No. XM_015448520.1), sequence identity to other human gene sequences and seed region matches to human microRNA (miRNA) sequences to predict off-target effects, and for overlap with known single nucleotide polymorphisms. Based on the results of the bioinformatics analysis, 465 sequences were selected, of which 320 sequences were prioritized for initial synthesis and in vitro testing.

RNAi constructs were synthesized using solid phase phosphoramidite chemistry. Synthesis was performed on a MerMade12 or MerMade192X (Bioautomation) instrument. Various chemical modifications, including 2'-fluoro modified nucleotides, 2'-O-methyl modified nucleotides, abasic nucleotides, and phosphorothioate internucleotide linkages, were incorporated into the molecules. The RNAi constructs were generally formatted to be duplexes of 19-21 base pairs when annealed with either no overhangs (double bluntmer) or one or two overhangs of 2 nucleotides at the 3' end of the antisense strand and/or the sense strand. The sense strands of the RNAi constructs were conjugated to a trivalent N-acetyl-galactosamine (GalNAc) moiety as described further below.

Materials

- Acetonitrile (DNA Synthesis Grade, AXO152-2505, EMD)
- Capping Reagent A (80:10:10 (v/v/v) tetrahydrofuran/lutidine/acetic anhydride, BIO221/4000, EMD)
- Capping Reagent B (16% 1-methylimidazole/tetrahydrofuran, BIO345/4000, EMD)
- Activator Solution (0.25 M 5-(ethylthio)-1H-tetrazole (ETT) in acetonitrile, BIO0152/0960, EMD)
- Detritylation Reagent (3% dichloroacetic acid in dichloromethane, BIO830/4000, EMD)
- Oxidation Reagent (0.02 M iodine in 70:20:10 (v/v/v) tetrahydrofuran/pyridine/water, BIO420/4000, EMD)
- Diethylamine solution (20% DEA in acetonitrile, NC0017-0505, EMD)
- Thiolation Reagent (0.05 M 5-N-[(dimethylamino)methylene]amino-3H-1,2,4-dithiazole-3-thione (BIOSULII/160K) in 40:60 (v/v) pyridine/acetonitrile)
- 5'-Aminohexyl linker phosphoramidite, phosphorylating phosphoramidite, 2'-deoxythymidine phosphoramidite, and 2'-methoxy and 2'-fluoro phosphoramidites of adenosine, guanosine, cytosine, and uridine (Thermo Fisher Scientific), 0.10 M in acetonitrile over ~10 mL of molecular sieves (3 Å, J. T. Baker)
- CPG Support (Hi-Load Universal Support, 500A (BH5-3500-G1), 79.6 μmol/g, 0.126 g (10 μmol))
- Ammonium hydroxide (concentrated, J. T. Baker)

Synthesis

Reagent solutions, phosphoramidite solutions, and solvents were attached to the MerMade12 instrument. Solid support was added to each column (4 mL SPE tube with top and bottom frit), and the columns were affixed to the instrument. The columns were washed twice with acetonitrile. The phosphoramidite and reagent solution lines were purged. The synthesis was initiated using the Poseidon software. The synthesis was accomplished by repetition of the deprotection/coupling/oxidation/capping synthesis cycle. Specifically, to the solid support was added detritylation reagent to remove the 5'-dimethoxytrityl (DMT) protecting group. The solid support was washed with acetonitrile. To the support was added phosphoramidite and activator solution followed by incubation to couple the incoming nucleotide to the free 5'-hydroxyl group. The support was washed with acetonitrile. To the support was added oxidation or thiolation reagent to convert the phosphite triester to the phosphate triester or phosphorothioate. To the support was added capping reagents A and B to terminate any unreacted oligonucleotide chains. The support was washed with acetonitrile. After the final reaction cycle, the resin was washed with diethylamine solution to remove the 2-cyanoethyl protecting groups. The support was washed with acetonitrile and dried under vacuum.

GalNAc Conjugation

Sense strands for conjugation to a trivalent GalNAc moiety (structure shown in Formula VII below) were prepared with a 5'-aminohexyl linker. After automated synthesis, the column was removed from the instrument and transferred to a vacuum manifold in a hood. The 5'-monomethoxytrityl (MMT) protecting group was removed from the solid support by successive treatments with 2 mL aliquots of 1% trifluoroacetic acid (TFA) in dichloromethane (DCM) with vacuum filtration. When the orange/yellow color was no longer observable in the eluent, the resin was washed with dichloromethane. The resin was washed with 5 mL of 2% diisopropylethylamine in N,N-dimethylformamide (DMF). In a separate vial a solution of GalNAc3-Lys2-Ahx (67 mg, 40 μmol) in DMF (0.5 mL), the structure and synthesis of which is described below, was prepared with 1,1,3,3-tetramethyluronium tetrafluoroborate (TATU, 12.83 mg, 40 μmol) and diisopropylethylamine (DIEA)(13.9 μL, 80 μmol). The activated coupling solution was added to the resin, and the column was capped and incubated at room temperature overnight. The resin was washed with DMF, DCM, and dried under vacuum.

Cleavage

The synthesis columns were removed from the synthesizer or vacuum manifold. The solid support from each column was transferred to a 10 mL vial. To the solid support was added 4 mL of concentrated ammonium hydroxide. The cap was tightly affixed to the bottle, and the mixture was heated at 55° C. for 4 h. The bottle was moved to the freezer and cooled for 20 minutes before opening in the hood. The mixture was filtered through an 8 mL SPE tube to remove the solid support. The vial and solid support were rinsed with 1 mL of 50:50 ethanol/water.

Analysis and Purification

A portion of the combined filtrate was analyzed and purified by anion exchange chromatography. The pooled fractions were desalted by size exclusion chromatography and analyzed by ion pair-reversed phase high-performance liquid chromatograph-mass spectrometry (HPLC-MS). The pooled fractions were lyophilized to obtain a white amorphous powder.

Analytical Anion Exchange Chromatography (AEX):

Column: Thermo DNAPac PA200RS (4.6×50 mm, 4 μm)

Instrument: Agilent 1100 HPLC

Buffer A: 20 mM sodium phosphate, 10% acetonitrile, pH 8.5

Buffer B: 20 mM sodium phosphate, 10% acetonitrile, pH 8.5, 1 M sodium bromide

Preparative Size Exclusion Chromatography (SEC):

Column: GE Hi-Prep 26/10

Instrument: GE AKTA Pure

Buffer: 20% ethanol in water

Flow Rate: 10 mL/min

Injection volume: 15 mL using sample loading pump

Ion Pair-Reversed Phase (IP-RP) HPLC:

Column: Water Xbridge BEH OST C18, 2.5 μm, 2.1×50 mm

Instrument: Agilent 1100 HPLC

Buffer A: 15.7 mM DIEA, 50 mM hexafluoroisopropanol (HFIP) in water

Buffer B: 15.7 mM DIEA, 50 mM HFIP in 50:50 water/acetonitrile

Flow rate: 0.5 mL/min

Gradient: 10-30% B over 6 min

Annealing

A small amount of the sense strand and the antisense strand were weighed into individual vials. To the vials was added siRNA reconstitution buffer (Qiagen) or phosphate buffered saline (PBS) to an approximate concentration of 2 mM based on the dry weight. The actual sample concentration was measured on the NanoDrop One (ssDNA, extinction coefficient=33 μg/OD260). The two strands were then mixed in an equimolar ratio, and the sample was heated for 5 minutes in a 90° C. incubator and allowed to cool slowly to room temperature. The sample was analyzed by AEX. The duplex was registered and submitted for in vitro and in vivo testing as described in more detail below.

Preparation of GalNAc3-Lys2-Ahx

Formula VII

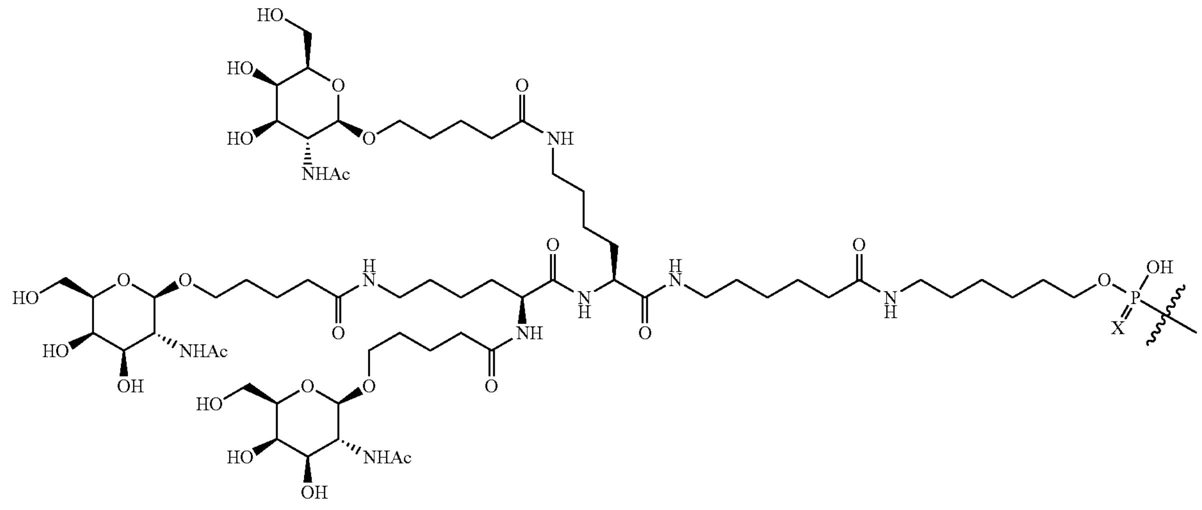

Flow rate: 1 mL/min at 40° C.

Gradient: 20-65% B in 6.2 min

Preparative Anion Exchange Chromatography (AEX):

Column: Tosoh TSK Gel SuperQ-5PW, 21×150 mm, 13 μm

Instrument: Agilent 1200 HPLC

Buffer A: 20 mM sodium phosphate, 10% acetonitrile, pH 8.5

Buffer B: 20 mM sodium phosphate, 10% acetonitrile, pH 8.5, 1 M sodium bromide

Flow rate: 8 mL/min

Injection volume: 5 mL

Gradient: 35-55% B over 20 min wherein X=O or S. The squiggly line represents the point of attachment to the 5' terminal nucleotide of the sense strand of the RNAi construct.

To a 50 mL falcon tube was added Fmoc-Ahx-OH (1.13 g, 3.19 mmol) in DCM (30 mL) followed by DIEA (2.23 mL, 12.78 mmol). The solution was added to 2-Cl Trityl chloride resin (3.03 g, 4.79 mmol) in a 50 mL centrifuge tube and loaded onto a shaker for 2 h. The solvent was drained and the resin was washed with 17:2:1 DCM/MeOH/DIEA (30 ml×2), DCM (30 mL×4) and dried. The loading was determined to be 0.76 mmol/g with UV spectrophotometric detection at 290 nm.

3 g of the loaded 2-Cl Trityl resin was suspended in 20% 4-methylpiperidine in DMF (20 mL), and after 30 min the solvent was drained. The process was repeated one more time, and the resin was washed with DMF (30 mL×3) and DCM (30 mL×3).

To a solution of Fmoc-Lys(ivDde)-OH (3.45 g, 6 mmol) in DMF (20 mL) was added TATU (1.94 g, 6 mmol) followed by DIEA (1.83 mL, 10.5 mmol). The solution was then added to the above deprotected resin, and the suspension was set on a shaker overnight. The solvent was drained and the resin was washed with DMF (30 mL×3) and DCM (30 mL×3).

The resin was treated with 20% 4-methylpiperidine in DMF (15 mL) and after 10 min the solvent was drained. The process was repeated one more time and the resin was washed with DMF (15 mL×4) and DCM (15 mL×4).

To a solution of Fmoc-Lys(Fmoc)-OH (3.54 g, 6 mmol) in DMF (20 mL) was added TATU (1.94 g, 6 mmol) followed by DIEA (1.83 mL, 10.5 mmol). The solution was then added to the above deprotected resin and the suspension was set on a shaker overnight. The solvent was drained and the resin was washed with DMF (30 mL×3) and DCM (30 mL×3).

The resin was treated with 5% hydrazine in DMF (20 mL) and after 5 min, the solvent was drained. The process was repeated four more times and the resin was washed with DMF (30 mL×4) and DCM (30 mL×4).

To a solution of 5-(((2R,3R,4R,5R,6R)-3-acetamido-4,5-diacetoxy-6-(acetoxymethyl)tetrahydro-2H-pyran-2-yl)oxy) pentanoic acid (4.47 g, 10 mmol) in DMF (40 mL) was added TATU (3.22 g, 10 mmol), and the solution was stirred for 5 min. DIEA (2.96 mL, 17 mmol) was added to the solution, and the mixture was then added to the resin above. The suspension was kept at room temperature overnight and the solvent was drained. The resin was washed with DMF (3×30 mL) and DCM (3×30 mL).

The resin was treated with 1% TFA in DCM (30 mL with 3% Triisopropylsilane) and after 5 min, the solvent was drained. The process was repeated three more times, and the combined filtrate was concentrated in vacuo. The residue was triturated with diethyl ether (50 mL) and the suspension was filtered and dried to give the crude product. The crude product was purified with reverse phase chromatography and eluted with 0-20% of MeCN in water. The fractions were combined and lyophilized to give the product as a white solid.

Based on activity in in vitro cell-based assays as described in Example 2 and in vivo transgenic mouse studies as described in Example 3, 137 sequences targeting specific regions of the human LPA transcript were selected for structure-activity relationship (SAR) studies. Table 1 below lists the unmodified sense and antisense sequences for molecules in each of the 137 sequence families. The range of nucleotides targeted by siRNA molecules in each sequence family within the human LPA transcript (SEQ ID NO: 1) is also shown in Table 1. As discussed above, the human LPA gene contains repeats of the KIV-2 domain and thus, the siRNA molecules may have more than one target site within the transcript if the target site lies within the KIV-2 domain or a conserved region among the other KIV domains. For clarity, only the first target site within the transcript is shown.

Table 2 provides the sequences of the sense and antisense strands with chemical modifications for exemplary duplexes resulting from the SAR studies. The nucleotide sequences are listed according to the following notations: a, u, g, and c=corresponding 2'-O-methyl ribonucleotide; Af, Uf, Gf, and Cf=corresponding 2'-deoxy-2'-fluoro ("2'-fluoro") ribonucleotide; Phos=terminal nucleotide has a monophosphate group at its 5' end; and invAb=inverted abasic nucleotide (i.e. abasic nucleotide linked to adjacent nucleotide via a substituent at its 3' position (a 3'-3' linkage) when on the 3' end of a strand or linked to adjacent nucleotide via a substituent at its 5' position (a 5'-5' internucleotide linkage) when on the 5' end of a strand. Insertion of an "s" in the sequence indicates that the two adjacent nucleotides are connected by a phosphorothiodiester group (e.g. a phosphorothioate internucleotide linkage). Unless indicated otherwise, all other nucleotides are connected by 3'-5' phosphodiester groups. [GalNAc3] represents the GalNAc moiety shown in Formula VII, which was covalently attached to the 5' end of the sense strand via a phosphodiester bond or a phosphorothioate bond when an "s" follows the [GalNAc3] notation.

TABLE 1

Unmodified LPA siRNA sequences

| Duplex No. | Target site within NM_005577.4 | Sense Sequence (5'-3') | SEQ ID NO: | Antisense Sequence (5'-3') | SEQ ID NO: |
|---|---|---|---|---|---|
| 6078 | 116-134 | CCUGAGCAAAGCCAUGUGAUU | 2 | UCACAUGGCUUUGCUCAGGUU | 134 |
| 5037 | 117-135 | CUGAGCAAAGCCAUGUGGUUU | 3 | ACCACAUGGCUUUGCUCAGUU | 135 |
| 5125 | 131-149 | GUGGUCCAGGAUUGCUACUUU | 4 | AGUAGCAAUCCUGGACCACUU | 136 |
| 4930 | 249-267 | CCACAGAAAACUACCCAAAUU | 5 | UUUGGGUAGUUUUCUGUGGUU | 137 |
| 5126 | 384-402 | CAGAAGGGACUGCCGUCGUUU | 6 | ACGACGGCAGUCCCUUCUGUU | 138 |
| 4932 | 385-402 | AGAAGGGACUGCCGUCGCGUU | 7 | CGCGACGGCAGUCCCUUCUUU | 139 |
| 6079 | 385-402 | AGAAGGGACUGCCGUCGCAUU | 8 | UGCGACGGCAGUCCCUUCUUU | 140 |
| 4776 | 437-455 | GCUCCUUCCGAACAAGCAUUU | 9 | AUGCUUGUUCGGAAGGAGCUU | 141 |
| 4777 | 438-456 | CUCCUUCCGAACAAGCACUUU | 10 | AGUGCUUGUUCGGAAGGAGUU | 142 |
| 4938 | 441-459 | CUUCCGAACAAGCACCGACUU | 11 | GUCGGUGCUUGUUCGGAAGUU | 143 |
| 4778 | 441-459 | CUUCCGAACAAGCACCGAUUU | 12 | AUCGGUGCUUGUUCGGAAGUU | 144 |

TABLE 1-continued

Unmodified LPA siRNA sequences

| Duplex No. | Target site within NM_005577.4 | Sense Sequence (5'-3') | SEQ ID NO: | Antisense Sequence (5'-3') | SEQ ID NO: |
|---|---|---|---|---|---|
| 4613; 6279 | 442-460 | UUCCGAACAAGCACCGACUUU | 13 | AGUCGGUGCUUGUUCGGAAUU | 145 |
| 6249; 6280; 6282 | 440-460 | CCUUCCGAACAAGCACCGACU | 14 | AGUCGGUGCUUGUUCGGAAGGUU | 146 |
| 6281 | 440-460 | CCUUCCGAACAAGCACCGAC | 15 | AGUCGGUGCUUGUUCGGAAGGUU | 146 |
| 6081 | 443-461 | UCCGAACAAGCACCGACUAUU | 16 | UAGUCGGUGCUUGUUCGGAUU | 147 |
| 4941 | 445-463 | CGAACAAGCACCGACUGAGUU | 17 | CUCAGUCGGUGCUUGUUCGUU | 148 |
| 6084 | 451-469 | AGCACCGACUGAGCAAAGAUU | 18 | UCUUUGCUCAGUCGGUGCUUU | 149 |
| 4816 | 452-470 | GCACCGACUGAGCAAAGGUUU | 19 | ACCUUUGCUCAGUCGGUGCUU | 150 |
| 4948 | 453-471 | CACCGACUGAGCAAAGGCCUU | 20 | GGCCUUUGCUCAGUCGGUGUU | 151 |
| 6086 | 466-484 | AAGGCCUGGGGUGCAGGAAUU | 21 | UUCCUGCACCCCAGGCCUUUU | 152 |
| 4956 | 471-489 | CUGGGGUGCAGGAGUGCUAUU | 22 | UAGCACUCCUGCACCCCAGUU | 153 |
| 11741 | 471-489 | CUGGGGUGCAGGAGUGCUAU | 23 | UAGCACUCCUGCACCCCAGUU | 153 |
| 4614 | 473-491 | GGGGUGCAGGAGUGCUACCUU | 24 | GGUAGCACUCCUGCACCCCUU | 154 |
| 4961 | 2689-2707 | GAAUCCAGAUCCUGUGGCAUU | 25 | UGCCACAGGAUCUGGAUUCUU | 155 |
| 5133 | 2699-2717 | CCUGUGGCAGCCCCUUAUUUU | 26 | AAUAAGGGGCUGCCACAGGUU | 156 |
| 4966; 5042; 5413 | 2704-2722 | GGCAGCCCCUUAUUGUUAUUU | 27 | AUAACAAUAAGGGGCUGCCUU | 157 |
| 5414; 6244 | 2702-2722 | GUGGCAGCCCCUUAUUGUUAU | 28 | AUAACAAUAAGGGGCUGCCACUU | 158 |
| 5417 | 2702-2722 | GUGGCAGCCCCUUAUUGUUA | 29 | AUAACAAUAAGGGGCUGCCACUU | 158 |
| 4967 | 2705-2723 | GCAGCCCCUUAUUGUUAUAUU | 30 | UAUAACAAUAAGGGGCUGCUU | 159 |
| 4599 | 2707-2725 | AGCCCCUUAUUGUUAUACGUU | 31 | CGUAUAACAAUAAGGGGCUUU | 160 |
| 6087 | 2707-2725 | AGCCCCUUAUUGUUAUACAUU | 32 | UGUAUAACAAUAAGGGGCUUU | 161 |
| 4969; 5409 | 2708-2726 | GCCCCUUAUUGUUAUACGAUU | 33 | UCGUAUAACAAUAAGGGGCUU | 162 |
| 5410 | 2706-2726 | CAGCCCCUUAUUGUUAUACG | 34 | UCGUAUAACAAUAAGGGGCUGUU | 163 |
| 4970 | 2709-2727 | CCCCUUAUUGUUAUACGAGUU | 35 | CUCGUAUAACAAUAAGGGGUU | 164 |
| 5430; 6245 | 2707-2727 | AGCCCCUUAUUGUUAUACGAG | 36 | CUCGUAUAACAAUAAGGGGCUUU | 165 |
| 5433 | 2707-2727 | AGCCCCUUAUUGUUAUACGA | 37 | CUCGUAUAACAAUAAGGGGCUUU | 165 |
| 6088 | 2709-2727 | CCCCUUAUUGUUAUACGAAUU | 38 | UUCGUAUAACAAUAAGGGGUU | 166 |
| 4971; 6183 | 2759-2777 | CUGACACAAUGCUCAGACGUU | 39 | CGUCUGAGCAUUGUGUCAGUU | 167 |
| 6089; 6138 | 2759-2777 | CUGACACAAUGCUCAGACAUU | 40 | UGUCUGAGCAUUGUGUCAGUU | 168 |
| 6139; 6140; 6143; 6144; 6145; 6146; 6147; 6148 | 2757-2777 | ACCUGACACAAUGCUCAGACA | 41 | UGUCUGAGCAUUGUGUCAGGUUU | 169 |

TABLE 1-continued

| Unmodified LPA siRNA sequences | | | | | |
|---|---|---|---|---|---|
| Duplex No. | Target site within NM_005577.4 | Sense Sequence (5'-3') | SEQ ID NO: | Antisense Sequence (5'-3') | SEQ ID NO: |
| 6141 | 2757-2777 | ACCUGACACAAUGCUCAGAC | 42 | UGUCUGAGCAUUGUGUCAGGUUU | 169 |
| 6174 | 2757-2777 | ACCUGACACAAUGCUCAGAC | 42 | CGUCUGAGCAUUGUGUCAGGUUU | 170 |
| 6236; 6246 | 2757-2777 | ACCUGACACAAUGCUCAGACG | 43 | CGUCUGAGCAUUGUGUCAGGUUU | 170 |
| 4972 | 2761-2779 | GACACAAUGCUCAGACGCAUU | 44 | UGCGUCUGAGCAUUGUGUCUU | 171 |
| 4973 | 2762-2780 | ACACAAUGCUCAGACGCAGUU | 45 | CUGCGUCUGAGCAUUGUGUUU | 172 |
| 6248 | 2760-2780 | UGACACAAUGCUCAGACGCAG | 46 | CUGCGUCUGAGCAUUGUGUCAUU | 173 |
| 7932; 7936; 7938; 11357 | 2760-2780 | UGACACAAUGCUCAGACGCAA | 47 | UUGCGUCUGAGCAUUGUGUCAUU | 174 |
| 7934; 8278; 11356 | 2760-2780 | UGACACAAUGCUCAGACGCA | 48 | UUGCGUCUGAGCAUUGUGUCAUU | 174 |
| 18448 | 2760-2780 | UGACACAAUGCUCAGACGCA | 48 | UUGCGUCUGAGCAUUGUGUCA | 176 |
| 10927; 11350 | 2762-2780 | ACACAAUGCUCAGACGCAAU | 49 | UUGCGUCUGAGCAUUGUGUUU | 175 |
| 11347; 11348; 11349 | 2762-2780 | ACACAAUGCUCAGACGCAAUU | 50 | UUGCGUCUGAGCAUUGUGUUU | 175 |
| 11351 | 2762-2780 | ACACAAUGCUCAGACGCA | 51 | UUGCGUCUGAGCAUUGUGUUU | 175 |
| 11352; 11354 | 2762-2780 | ACACAAUGCUCAGACGCAA | 52 | UUGCGUCUGAGCAUUGUGUUU | 175 |
| 4601; 5043; 6276; 7900 | 2824-2842 | CCUAGAGGCUCCUUCUGAAUU | 53 | UUCAGAAGGAGCCUCUAGGUU | 177 |
| 6247; 6278 | 2822-2842 | AGCCUAGAGGCUCCUUCUGAA | 54 | UUCAGAAGGAGCCUCUAGGCUUU | 178 |
| 6277; 7902 | 2822-2842 | AGCCUAGAGGCUCCUUCUGA | 55 | UUCAGAAGGAGCCUCUAGGCUUU | 178 |
| 4978 | 2827-2845 | AGAGGCUCCUUCUGAACAAUU | 56 | UUGUUCAGAAGGAGCCUCUUU | 179 |
| 6091 | 2845-2863 | AGCACCAACUGAGCAAAGAUU | 57 | UCUUUGCUCAGUUGGUGCUUU | 180 |
| 4984 | 3031-3049 | AAAUCCAGAUCCUGUGGCAUU | 58 | UGCCACAGGAUCUGGAUUUUU | 181 |
| 5044 | 3046-3064 | GGCAGCCCCUUGGUGUUAUUU | 59 | AUAACACCAAGGGGCUGCCUU | 182 |
| 4683; 6180 | 3278-3296 | AGAACUUGCCAAGCUUGGUUU | 60 | ACCAAGCUUGGCAAGUUCUUU | 183 |
| 6274; 6347 | 3276-3296 | GAAGAACUUGCCAAGCUUGGU | 61 | ACCAAGCUUGGCAAGUUCUUCUU | 184 |
| 6172 | 3276-3296 | GAAGAACUUGCCAAGCUUGG | 62 | ACCAAGCUUGGCAAGUUCUUCUU | 184 |
| 4792; 6181 | 3279-3297 | GAACUUGCCAAGCUUGGUUUU | 63 | AACCAAGCUUGGCAAGUUCUU | 185 |
| 6348; 6235 | 3277-3297 | AAGAACUUGCCAAGCUUGGUU | 64 | AACCAAGCUUGGCAAGUUCUUUU | 186 |
| 6173 | 3277-3297 | AAGAACUUGCCAAGCUUGGU | 65 | AACCAAGCUUGGCAAGUUCUUUU | 186 |
| 4818 | 3310-3328 | ACACCAGCAUAGUCGGACUUU | 66 | AGUCCGACUAUGCUGGUGUUU | 187 |

TABLE 1-continued

| Unmodified LPA siRNA sequences | | | | | |
|---|---|---|---|---|---|
| Duplex No. | Target site within NM_005577.4 | Sense Sequence (5'-3') | SEQ ID NO: | Antisense Sequence (5'-3') | SEQ ID NO: |
| 5129 | 3311-3329 | CACCAGCAUAGUCGGACCUUU | 67 | AGGUCCGACUAUGCUGGUGUU | 188 |
| 4705; 11313 | 3392-3410 | CGCCCUUGGUGUUACACCAUU | 68 | UGGUGUAACACCAAGGGCGUU | 189 |
| 20022 | 3392-3410 | CGCCCUUGGUGUUACACCAU | 610 | UGGUGUAACACCAAGGGCGUU | 189 |
| 8336 | 3390-3410 | UUCGCCCUUGGUGUUACACCA | 69 | UGGUGUAACACCAAGGGCGAAUU | 190 |
| 11315; 20033 | 3392-3410 | CGCCCUUGGUGUUACACC | 70 | UGGUGUAACACCAAGGGCGUU | 189 |
| 11316; 11318 | 3392-3410 | CGCCCUUGGUGUUACACCA | 71 | UGGUGUAACACCAAGGGCGUU | 189 |
| 11320; 11322; 20027 | 3390-3410 | UUCGCCCUUGGUGUUACACC | 72 | UGGUGUAACACCAAGGGCGAAUU | 190 |
| 20040; 20047 | 3390-3410 | UUCGCCCUUGGUGUUACACC | 72 | UGGUGUAACACCAAGGGCGAA | 611 |
| 4706 | 3393-3411 | GCCCUUGGUGUUACACCAUUU | 73 | AUGGUGUAACACCAAGGGCUU | 191 |
| 8207; 8213 | 3391-3411 | UCGCCCUUGGUGUUACACCA | 74 | AUGGUGUAACACCAAGGGCGAUU | 192 |
| 8918 | 3393-3411 | GCCCUUGGUGUUACACCAUU | 75 | AUGGUGUAACACCAAGGGCUU | 191 |
| 4800 | 3399-3417 | GGUGUUACACCAUGGAUCUUU | 76 | AGAUCCAUGGUGUAACACCUU | 193 |
| 4629; 17183 | 3464-3482 | GAAUCAAGUGUCCUUGCAAUU | 77 | UUGCAAGGACACUUGAUUCUU | 194 |
| 11372; 11582; 17203 | 3462-3482 | CAGAAUCAAGUGUCCUUGCA | 78 | UUGCAAGGACACUUGAUUCUGUU | 195 |
| 18434; 18439; 18444 | 3462-3482 | CAGAAUCAAGUGUCCUUGCA | 78 | UUGCAAGGACACUUGAUUCUG | 196 |
| 11374; 17194 | 3464-3482 | GAAUCAAGUGUCCUUGCAAU | 79 | UUGCAAGGACACUUGAUUCUU | 194 |
| 17197; 17198; 17201 | 3464-3482 | GAAUCAAGUGUCCUUGCA | 80 | UUGCAAGGACACUUGAUUCUU | 194 |
| 4630 | 3465-3483 | AAUCAAGUGUCCUUGCAACUU | 81 | GUUGCAAGGACACUUGAUUUU | 197 |
| 4804; 17184 | 3465-3483 | AAUCAAGUGUCCUUGCAAUUU | 82 | AUUGCAAGGACACUUGAUUUU | 198 |
| 11368; 17189 | 3463-3483 | AGAAUCAAGUGUCCUUGCAA | 83 | AUUGCAAGGACACUUGAUUCUUU | 199 |
| 18436; 18442; 18446 | 3465-3483 | AGAAUCAAGUGUCCUUGCAA | 83 | AUUGCAAGGACACUUGAUUCU | 200 |
| 11370 | 3463-3483 | AGAAUCAAGUGUCCUUGCAAU | 84 | AUUGCAAGGACACUUGAUUCUUU | 199 |
| 11580; 17187; 17190; 17192 | 3465-3483 | AAUCAAGUGUCCUUGCAAUU | 85 | AUUGCAAGGACACUUGAUUUU | 198 |
| 17188; 17191; 17193 | 3465-3483 | AAUCAAGUGUCCUUGCAA | 86 | AUUGCAAGGACACUUGAUUUU | 198 |
| 4805 | 3467-3485 | UCAAGUGUCCUUGCAACUUUU | 87 | AAGUUGCAAGGACACUUGAUU | 201 |

TABLE 1-continued

| Unmodified LPA siRNA sequences | | | | | |
|---|---|---|---|---|---|
| Duplex No. | Target site within NM_005577.4 | Sense Sequence (5'-3') | SEQ ID NO: | Antisense Sequence (5'-3') | SEQ ID NO: |
| 4823 | 3519-3537 | CUUCUGAAGAAGCACCAAUUU | 88 | AUUGGUGCUUCUUCAGAAGUU | 202 |
| 6093 | 3520-3538 | UUCUGAAGAAGCACCAACAUU | 89 | UGUUGGUGCUUCUUCAGAAUU | 203 |
| 5137; 11337 | 3632-3650 | UCUUGGUCCUCUAUGACAUUU | 90 | AUGUCAUAGAGGACCAAGAUU | 204 |
| 8395; 8401; 11344 | 3630-3650 | AGUCUUGGUCCUCUAUGACA | 91 | AUGUCAUAGAGGACCAAGACUUU | 205 |
| 11338 | 3632-3650 | UCUUGGUCCUCUAUGACAUU | 92 | AUGUCAUAGAGGACCAAGAUU | 204 |
| 11340; 11342 | 3632-3650 | UCUUGGUCCUCUAUGACAU | 93 | AUGUCAUAGAGGACCAAGAUU | 204 |
| 11341 | 3632-3650 | UCUUGGUCCUCUAUGACA | 94 | AUGUCAUAGAGGACCAAGAUU | 204 |
| 5134 | 3645-3663 | UGACACCACACUGGCAUCAUU | 95 | UGAUGCCAGUGUGGUGUCAUU | 206 |
| 11835 | 3667-3685 | GACAACAGAAUAUUAUCCAU | 96 | UGGAUAAUAUUCUGUUGUCUU | 207 |
| 4835 | 3780-3798 | GCAACCUGACACAAUGUCUUU | 97 | AGACAUUGUGUCAGGUUGCUU | 208 |
| 5102 | 3788-3806 | ACACAAUGUCCAGUGACAGUU | 98 | CUGUCACUGGACAUUGUGUUU | 209 |
| 6100 | 3788-3806 | ACACAAUGUCCAGUGACAAUU | 99 | UUGUCACUGGACAUUGUGUUU | 210 |
| 4733 | 3793-3811 | AUGUCCAGUGACAGAAUCAUU | 100 | UGAUUCUGUCACUGGACAUUU | 211 |
| 5105 | 3795-3813 | GUCCAGUGACAGAAUCAAGUU | 101 | CUUGAUUCUGUCACUGGACUU | 212 |
| 6101 | 3795-3813 | GUCCAGUGACAGAAUCAAAUU | 102 | UUUGAUUCUGUCACUGGACUU | 213 |
| 5106 | 3796-3814 | UCCAGUGACAGAAUCAAGUUU | 103 | ACUUGAUUCUGUCACUGGAUU | 214 |
| 5147; 17185 | 3797-3815 | CCAGUGACAGAAUCAAGUAUU | 104 | UACUUGAUUCUGUCACUGGUU | 215 |
| 11379 | 3795-3815 | GUCCAGUGACAGAAUCAAGUA | 105 | UACUUGAUUCUGUCACUGGACUU | 216 |
| 11838; 11839; 17204; 17205 | 3795-3815 | GUCCAGUGACAGAAUCAAGU | 106 | UACUUGAUUCUGUCACUGGACUU | 216 |
| 18450; 18455 | 3795-3815 | GUCCAGUGACAGAAUCAAGU | 106 | UACUUGAUUCUGUCACUGGAC | 217 |
| 11745; 17195; 17196 | 3797-3815 | CCAGUGACAGAAUCAAGUAU | 107 | UACUUGAUUCUGUCACUGGUU | 215 |
| 17199; 17200; 17202 | 3797-3815 | CCAGUGACAGAAUCAAGU | 108 | UACUUGAUUCUGUCACUGGUU | 215 |
| 5116 | 3922-3940 | CACCACUGUUACAGGAAGGUU | 109 | CCUUCCUGUAACAGUGGUGUU | 218 |
| 6102 | 3922-3940 | CACCACUGUUACAGGAAGAUU | 110 | UCUUCCUGUAACAGUGGUGUU | 219 |
| 11743 | 3990-4010 | CAGAAUACUACCCAAAUGGU | 111 | UACCAUUUGGGUAGUAUUCUGUU | 220 |
| 5122 | 4000-4018 | CCCAAAUGGUGGCCUGACCUU | 112 | GGUCAGGCCACCAUUUGGGUU | 221 |
| 5124 | 4064-4082 | UAUACCAUGGAUCCCAGUGUU | 113 | CACUGGGAUCCAUGGUAUAUU | 222 |
| 6106 | 4064-4082 | UAUACCAUGGAUCCCAGUAUU | 114 | UACUGGGAUCCAUGGUAUAUU | 223 |

TABLE 1-continued

| Unmodified LPA siRNA sequences | | | | | |
|---|---|---|---|---|---|
| Duplex No. | Target site within NM_005577.4 | Sense Sequence (5'-3') | SEQ ID NO: | Antisense Sequence (5'-3') | SEQ ID NO: |
| 4995; 6182; 7915 | 4180-4198 | UUCUGAAGAAGCACCAACUUU | 115 | AGUUGGUGCUUCUUCAGAAUU | 224 |
| 6149; 6152; 6153; 6154; 6155; 6156; 7922 | 4178-4198 | CCUUCUGAAGAAGCACCAACU | 116 | AGUUGGUGCUUCUUCAGAAGGUU | 225 |
| 6150; 6151; 7919 | 4178-4198 | CCUUCUGAAGAAGCACCAAC | 117 | AGUUGGUGCUUCUUCAGAAGGUU | 225 |
| 5049 | 4182-4200 | CUGAAGAAGCACCAACUGAUU | 118 | UCAGUUGGUGCUUCUUCAGUU | 226 |
| 4849 | 4189-4207 | AGCACCAACUGAAAACAGUUU | 119 | ACUGUUUUCAGUUGGUGCUUU | 227 |
| 11836 | 4187-4207 | GAAGCACCAACUGAAAACAG | 120 | ACUGUUUUCAGUUGGUGCUUCUU | 228 |
| 6109 | 4498-4516 | CCCGGUUCCAAGCACAGAAUU | 121 | UUCUGUGCUUGGAACCGGGUU | 229 |
| 6110 | 4508-4526 | AGCACAGAGGCUCCUUCUAUU | 122 | UAGAAGGAGCCUCUGUGCUUU | 230 |
| 4815 | 4520-4538 | CCUUCUGAACAAGCACCACUU | 123 | GUGGUGCUUGUUCAGAAGGUU | 231 |
| 4852 | 4520-4538 | CCUUCUGAACAAGCACCAUUU | 124 | AUGGUGCUUGUUCAGAAGGUU | 232 |
| 6113 | 4799-4817 | UCAGAAACAGAAUCAGGUAUU | 125 | UACCUGAUUCUGUUUCUGAUU | 233 |
| 5142 | 4806-4824 | CAGAAUCAGGUGUCCUAGAUU | 126 | UCUAGGACACCUGAUUCUGUU | 234 |
| 4861 | 4929-4947 | GUUAUCGAGGCACAUUCUUUU | 127 | AAGAAUGUGCCUCGAUAACUU | 235 |
| 5015 | 4930-4948 | UUAUCGAGGCACAUUCUCCUU | 128 | GGAGAAUGUGCCUCGAUAAUU | 236 |
| 4862 | 4930-4948 | UUAUCGAGGCACAUUCUCUUU | 129 | AGAGAAUGUGCCUCGAUAAUU | 237 |
| 6115 | 5132-5150 | ACGCGAUGCUCAGACACAAUU | 130 | UUGUGUCUGAGCAUCGCGUUU | 238 |
| 6116 | 5143-5161 | AGACACAGAAGGGACUGUAUU | 131 | UACAGUCCCUUCUGUGUCUUU | 239 |
| 6117 | 5507-5525 | UGUCCUGGAAGCAUUGUAAUU | 132 | UUACAAUGCUUCCAGGACAUU | 240 |
| 5140 | 5575-5593 | AACAAGGUUUGGAAAGCAUUU | 133 | AUGCUUUCCAAACCUUGUUUU | 241 |

TABLE 2

| Modified LPA siRNA sequences | | | | |
|---|---|---|---|---|
| Duplex No. | Sense Sequence (5'-3') | SEQ ID NO: | Antisense Sequence (5'-3') | SEQ ID NO: |
| 6078 | [GalNAc3]ccugagCfaAfAfGfCfcaugugasusu | 242 | [Phos]usCfsaCfaUfGfgcuuUfgCfucaggsusu | 437 |
| 5037 | [GalNAc3]CfuGfaGfcAfaAfGfCfCfauGfuGfgUfsusUf | 243 | [Phos]asCfscAfcAfUfggcuUfuGfcUfcAfgsUfsu | 438 |
| 5125 | [GalNAc3]guggucCfaGfGfAfUfugcuacususu | 244 | [Phos]asGfsuAfgCfAfauccUfgGfaccacsusu | 439 |
| 4930 | [GalNAc3]ccacagAfaAfAfCfUfacccaaasusu | 245 | [Phos]usUfsuGfgGfUfaguuUfuCfuguggsusu | 440 |
| 5126 | [GalNAc3]cagaagGfgAfCfUfGfccgucgususu | 246 | [Phos]asCfsgAfcGfGfcaguCfcCfuucugsusu | 441 |
| 4932 | [GalNAc3]agaaggGfaCfUfGfCfcgucgcgsusu | 247 | [Phos]csGfscGfaCfGfgcagUfcCfcuucususu | 442 |
| 6079 | [GalNAc3]agaaggGfaCfUfGfCfcgucgcasusu | 248 | [Phos]usGfscGfaCfGfgcagUfcCfcuucususu | 443 |
| 4776 | [GalNAc3]gcuccuUfcCfGfAfAfcaagcaususu | 249 | [Phos]asUfsgCfuUfGfuucgGfaAfggagcsusu | 444 |

TABLE 2-continued

| Modified LPA siRNA sequences | | | | |
|---|---|---|---|---|
| Duplex No. | Sense Sequence (5'-3') | SEQ ID NO: | Antisense Sequence (5'-3') | SEQ ID NO: |
| 4777 | [GalNAc3]cuccuuCfcGfAfAfCfaagcacususu | 250 | [Phos]asGfsuGfcUfUfguucGfgAfaggagsusu | 445 |
| 4938 | [GalNAc3]cuuccgAfaCfAfAfGfcaccgacsusu | 251 | [Phos]gsUfscGfgUfGfcuugUfuCfggaagsusu | 446 |
| 4778 | [GalNAc3]cuuccgAfaCfAfAfGfcaccgausus u | 252 | [Phos]asUfscGfgUfGfcuugUfuCfggaagsusu | 447 |
| 4613 | [GalNAc3]uuccgaAfcAfAfGfCfaccgacususu | 253 | [Phos]asGfsuCfgGfUfgcuuGfuUfcggaasusu | 448 |
| 6249 | [GalNAc3][invAb]CfcUfuCfcGfaAfcAfAfGf CfacCfgAfscsUf | 254 | [Phos]asGfsuCfgGfUfgcuuGfuUfcGfgAfaGf gsUfsu | 449 |
| 6279 | [GalNAc3][invAb]uuccgaAfcAfAfGfCfaccgacususu | 255 | [Phos]asGfsuCfgGfUfgcuuGfuUfcggaasusu | 448 |
| 6280 | [GalNAc3]ccuuccgaAfcAfAfGfCfaccgascsu | 256 | [Phos]asGfsuCfgGfUfgcuuGfuUfcggaaggsusu | 450 |
| 6281 | [GalNAc3][invAb]ccuuccgaAfcAfAfGfCfaccgacs [invAb] | 257 | [Phos]asGfsuCfgGfUfgcuuGfuUfcggaaggsusu | 450 |
| 6282 | [GalNAc3][invAb]ccuuccgaAfcAfAfGfCfaccgascsu | 258 | [Phos]asGfsuCfgGfUfgcuuGfuUfcggaaggsusu | 450 |
| 6081 | [GalNAc3]uccgaaCfaAfGfCfAfccgacuasusu | 259 | [Phos]usAfsgUfcGfGfugcuUfgUfucggasusu | 451 |
| 4941 | [GalNAc3]cgaacaAfgCfAfCfCfgacugagsusu | 260 | [Phos]csUfscAfgUfCfggugCfuUfguucgsusu | 452 |
| 6084 | [GalNAc3]agcaccGfaCfUfGfAfgcaaagasusu | 261 | [Phos]usCfsuUfuGfCfucagUfcGfgugcusus u | 453 |
| 4816 | [GalNAc3]gcaccgAfcUfGfAfGfcaaaggusus u | 262 | [Phos]asCfscUfuUfGfcucaGfuCfggugcsusu | 454 |
| 4948 | [GalNAc3]caccgaCfuGfAfGfCfaaaggccsusu | 263 | [Phos]gsGfscCfuUfUfgcucAfgUfcggugsusu | 455 |
| 6086 | [GalNAc3]aaggccUfgGfGfGfUfgcaggaasus u | 264 | [Phos]usUfscCfuGfCfacccCfaGfgccuusus u | 456 |
| 4956 | [GalNAc3]cuggggUfgCfAfGfGfagugcuasusu | 265 | [Phos]usAfsgCfaCfUfccugCfaCfcccagsusu | 457 |
| 11741 | [GalNAc3]scuggggUfgCfAfGfGfagugcuaus[invAb] | 266 | usAfsgcacUfccugCfaCfcccagsusu | 458 |
| 4614 | [GalNAc3]ggggugCfaGfGfAfGfugcuaccsusu | 267 | [Phos]gsGfsuAfgCfAfcuccUfgCfaccccsusu | 459 |
| 4961 | [GalNAc3]gaauccAfgAfUfCfCfuguggcasusu | 268 | [Phos]usGfscCfaCfAfggauCfuGfgauucsusu | 460 |
| 5133 | [GalNAc3]ccugugGfcAfGfCfCfccuuauusus u | 269 | [Phos]asAfsuAfaGfGfggcuGfcCfacaggsusu | 461 |
| 4966 | [GaINAc3]ggcagcCfcCfUfUfAfuuguuausus u | 270 | [Phos]asUfsaAfcAfAfuaagGfgGfcugccsusu | 462 |
| 5042 | [GaINAc3]GfgCfaGfcCfcCfUfUfAfuuGfuUfaUfsusUf | 271 | [Phos]asUfsaAfcAfAfuaagGfgGfcUfgCfcsUfsu | 463 |
| 5413 | [GalNAc3][invAb]ggcagcCfcCfUfUfAfuuguuausus u | 272 | [Phos]asUfsaAfcAfAfuaagGfgGfcugccsusu | 462 |
| 5414 | [GalNAc3]guggcagcCfcCfUfUfAfuuguusasu | 273 | [Phos]asUfsaAfcAfAfuaagGfgGfcugccacsusu | 464 |
| 5417 | [GalNAc3][invAb]guggcagcCfcCfUfUfAfuuguuas [invAb] | 274 | [Phos]asUfsaAfcAfAfuaagGfgGfcugccacsusu | 464 |
| 6244 | [GalNAc3][invAb]GfuGfgCfaGfcCfcCfUfUf AfuuGfuUfsasUf | 275 | [Phos]asUfsaAfcAfAfuaagGfgGfcUfgCfcAfcs Ufsu | 465 |
| 4967 | [GalNAc3]gcagccCfcUfUfAfUfuguuauasusu | 276 | [Phos]usAfsuAfaCfAfauaaGfgGfgcugcsusu | 466 |
| 4599 | [GalNAc3]agccccUfuAfUfUfGfuuauacgsusu | 277 | [Phos]csGfsuAfuAfAfcaauAfaGfgggcusus u | 467 |
| 6087 | [GalNAc3]agccccUfuAfUfUfGfuuauacasusu | 278 | [Phos]usGfsuAfuAfAfcaauAfaGfgggcusus u | 468 |
| 4969 | [GalNAc3]gccccuUfaUfUfGfUfuauacgasusu | 279 | [Phos]usCfsgUfaUfAfacaaUfaAfggggcsusu | 469 |
| 5409 | [GalNAc3][invAb]gccccuUfaUfUfGfUfuauacgasusu | 280 | [Phos]usCfsgUfaUfAfacaaUfaAfggggcsusu | 469 |
| 5410 | [GalNAc3]cagcccCfuUfAfUfUfguuauacgs[invAb] | 281 | [Phos]usCfsgUfaUfaAfCfaauaAfgGfggcugsusu | 470 |

TABLE 2-continued

| Modified LPA siRNA sequences | | | | |
|---|---|---|---|---|
| Duplex No. | Sense Sequence (5'-3') | SEQ ID NO: | Antisense Sequence (5'-3') | SEQ ID NO: |
| 4970 | [GalNAc3]ccccuuAfuUfGfUfUfauacgagsusu | 282 | [Phos]csUfscGfuAfUfaacaAfuAfaggggsusu | 471 |
| 5430 | [GaINAc3]agccccuuAfuUfGfUfUfauacgsasg | 283 | [Phos]csUfscGfuAfUfaacaAfuAfaggggcususu | 472 |
| 5433 | [GalNAc3][invAb]agccccuuAfuUfGfUfUfauacgas [invAb] | 284 | [Phos]csUfscGfuAfUfaacaAfuAfaggggcususu | 472 |
| 6088 | [GalNAc3]ccccuuAfuUfGfUfUfauacgaasusu | 285 | [Phos]usUfscGfuAfUfaacaAfuAfaggggsusu | 473 |
| 6245 | [GalNAc3][invAb]agccccuuAfuUfGfUfUfauacgsasg | 286 | [Phos]csUfscGfuAfUfaacaAfuAfaggggcususu | 472 |
| 4971 | [GalNAc3]cugacaCfaAfUfGfCfucagacgsusu | 287 | [Phos]csGfsuCfuGfAfgcauUfgUfgucagsusu | 474 |
| 6089 | [GalNAc3]cugacaCfaAfUfGfCfucagacasusu | 288 | [Phos]usGfsuCfuGfAfgcauUfgUfgucagsusu | 475 |
| 6138 | [GalNAc3][invAb]cugacaCfaAfUfGfCfucagacasusu | 289 | [Phos]usGfsuCfuGfAfgcauUfgUfgucagsusu | 475 |
| 6139 | [GalNAc3]accugacaCfaAfUfGfCfucagascsa | 290 | [Phos]usGfsuCfuGfAfgcauUfgUfgucaggususu | 476 |
| 6140 | [GalNAc3][invAb]AfcCfuGfaCfaCfaAfuGfC fucAfgAfscsAf | 291 | [Phos]usGfsuCfuGfAfgcAfuUfgUfgUfcAfgGfu sUfsu | 477 |
| 6141 | [GalNAc3][invAb]accugacaCfaAfUfGfCfucagacs [invAb] | 292 | [Phos]usGfsuCfuGfAfgcauUfgUfgucaggususu | 476 |
| 6143 | [GalNAc3][invAb]accugacaCfaAfUfGfCfucagascsa | 293 | [Phos]usGfsuCfuGfAfgcauUfgUfgucaggususu | 476 |
| 6144 | [GalNAc3][invAb]accugacaCfaAfUfGfCfucagascsa | 293 | [Phos]usGfsuCfugAfgcauUfgUfgucaggususu | 478 |
| 6145 | [GalNAc3][invAb]accugacaCfaAfUfGfCfucagascsa | 293 | [Phos]usGfsucuGfAfgcauUfgUfgucaggususu | 479 |
| 6146 | [GalNAc3][invAb]accugacaCfaAfUfGfCfucagascsa | 293 | [Phos]usGfsucugAfgcauUfgUfgucaggususu | 480 |
| 6147 | [GalNAc3][invAb]accugacaCfaAfUfGfCfucagascsa | 293 | [Phos]usGfsuCfuGfAfgcAfuUfgUfgucaggususu | 481 |
| 6148 | [GalNAc3][invAb]accugacaCfaAfUfGfCfucagascsa | 293 | [Phos]UfsgsUfcUfgAfgcauUfgUfgucaggususu | 482 |
| 6183 | [GalNAc3][invAb]cugacaCfaAfUfGfCfucagacgsusu | 294 | [Phos]csGfsuCfuGfAfgcauUfgUfgucagsusu | 474 |
| 6174 | [GalNAc3][invAb]accugacaCfaAfUfGfCfucagacs [invAb] | 292 | [Phos]csGfsuCfuGfAfgcauUfgUfgucaggususu | 483 |
| 6236 | [GalNAc3][invAb]accugacaCfaAfUfGfCfucagascsg | 295 | [Phos]csGfsuCfuGfAfgcauUfgUfgucaggususu | 483 |
| 6246 | [GalNAc3]accugacaCfaAfUfGfCfucagascsg | 296 | [Phos]csGfsuCfuGfAfgcauUfgUfgucaggususu | 483 |
| 4972 | [GalNAc3]gacacaAfuGfCfUfCfagacgcasusu | 297 | [Phos]usGfscGfuCfUfgagcAfuUfgugucsusu | 484 |
| 4973 | [GalNAc3]acacaaUfgCfUfCfAfgacgcagsusu | 298 | [Phos]csUfsgCfgUfCfugagCfaUfugugususu | 485 |
| 6248 | [GalNAc3][invAb]ugacacaaUfgCfUfCfAfgacgcsasg | 299 | [Phos]csUfsgCfgUfCfugagCfaUfugugucasusu | 486 |
| 7932 | [GalNAc3]sugacacaaUfgCfUfCfAfgacgcsasa | 300 | usUfsgCfgUfCfugagCfaUfugugucasusu | 487 |
| 7934 | [GalNAc3]sugacacAfaUfGfCfUfcagacgcas[invAb] | 301 | usUfsgCfgUfcUfGfagcaUfuGfugucasusu | 488 |
| 7936 | [GalNAc3]s[invAb]ugacacaaUfgCfUfCfAfgacgcsasa | 302 | usUfsgCfguCfugagCfaUfugugucasusu | 489 |
| 7938 | [GalNAc3]s[invAb]ugacacaaUfgCfUfCfAfgacgcsasa | 302 | usUfsgCfgUfCfugAfgCfaUfugugucasusu | 490 |
| 8278 | [GalNAc3]sugacacaaUfgCfUfCfAfgacgcas[invAb] | 303 | usUfsgcguCfugagCfaUfugugucasusu | 491 |
| 10927 | [GalNAc3]sacacaaUfgCfUfCfAfgacgcaaus[invAb] | 304 | usUfsgcguCfugagCfaUfugugususu | 492 |
| 11347 | [GalNAc3]s[invAb]acacaaUfgCfUfCfAfgacgcaasusu | 305 | usUfsgcguCfugagCfaUfugugususu | 492 |
| 11348 | [GalNAc3]s[invAb]acacaaUfgCfUfCfAfgacgcaasusu | 305 | usUfsgcguCfugagcaUfuGfugususu | 493 |
| 11349 | [GalNAc3]s[invAb]acacaaUfGfCfUfcagacgcaasusu | 306 | usUfsgcguCfugagCfaUfugugususu | 492 |
| 11350 | [GalNAc3]sacacaaUfgCfUfCfAfgacgcaaus[invAb] | 304 | usUfsgcguCfugagcaUfuGfugususu | 493 |
| 11351 | {GalNAc3]sacacaaUfgCfUfCfAfgacgcas[invAb] | 307 | usUfsgcguCfugagCfaUfugugususu | 492 |

TABLE 2-continued

| Modified LPA siRNA sequences | | | | |
|---|---|---|---|---|
| Duplex No. | Sense Sequence (5'-3') | SEQ ID NO: | Antisense Sequence (5'-3') | SEQ ID NO: |
| 11352 | [GalNAc3]s[invAb]acacaaUfgCfUfCfAfgacgcsasa | 308 | usUfsgcguCfugagCfaUfugugususu | 492 |
| 11354 | [GalNAc3]s[invAb]acacaaUfGfCfUfcagacgcsasa | 309 | usUfsgcguCfugagcaUfuGfugususu | 493 |
| 11356 | [GalNAc3]sugacacAfaUfGfCfUfcagacgcas[invAb] | 301 | usUfsgCfgUfcugagcaUfuGfugucasusu | 494 |
| 11357 | [GalNAc3]s[invAb]ugacacAfaUfGfCfUfcagacgcsasa | 310 | usUfsgcguCfugagcaUfuGfugucasusu | 495 |
| 18448 | [GalNAc3]sugacacaaUfgCfUfCfAfgacgcas[invAb] | 311 | usUfsgcguCfugagCfaUfuguguscsa | 496 |
| 4601 | [GalNAc3]ccuagaGfgCfUfCfCfuucugaasusu | 312 | [Phos]usUfscAfgAfAfggagCfcUfcuaggsusu | 497 |
| 5043 | [GalNAc3]CfcUfaGfaGfgCfUfCfCfuuCfuGfaAfsusUf | 313 | [Phos]usUfscAfgAfAfggagCfcUfcUfaGfgsUfsu | 498 |
| 6247 | [GalNAc3]agccuagaGfgCfUfCfCfuucugsasa | 314 | [Phos]usUfscAfgAfAfggagCfcUfcuaggcususu | 499 |
| 6276 | [GalNAc3][invAb]ccuagaGfgCfUfCfCfuucugaasusu | 315 | [Phos]usUfscAfgAfAfggagCfcUfcuaggsusu | 497 |
| 6277 | [GalNAc3][invAb]agccuagaGfgCfUfCfCfuucugas [invAb] | 316 | [Phos]usUfscAfgAfAfggagCfcUfcuaggcususu | 499 |
| 6278 | [GalNAc3][invAb]agccuagaGfgCfUfCfCfuucugsasa | 317 | [Phos]usUfscAfgAfAfggagCfcUfcuaggcususu | 499 |
| 7900 | [GalNAc3]s[invAb]ccuagaGfgCfUfCfCfuucugaasusu | 318 | usUfscAfgAfAfggagCfcUfcuaggsusu | 500 |
| 7902 | [GalNAc3]sagccuaGfaGfGfCfUfccuucugas[invAb] | 319 | usUfscAfgAfaGfGfagccUfcUfaggcususu | 501 |
| 4978 | [GalNAc3]agaggcUfcCfUfUfCfugaacaasusu | 320 | [Phos]usUfsgUfuCfAfgaagGfaGfccucususu | 502 |
| 6091 | [GalNAc3]agcaccAfaCfUfGfAfgcaaagasusu | 321 | [Phos]usCfsuUfuGfCfucagUfuGfgugcususu | 503 |
| 4984 | [GalNAc3]aaauccAfgAfUfCfCfuguggcasusu | 322 | [Phos]usGfscCfaCfAfggauCfuGfgauuususu | 504 |
| 5044 | [GalNAc3]GfgCfaGfcCfcCfUfUfGfguGfuUfaUfsusUf | 323 | [Phos]asUfsaAfcAfCfcaagGfgGfcUfgCfcsUfsu | 505 |
| 4683 | [GalNAc3]agaacuUfgCfCfAfAfgcuuggusus u | 324 | [Phos]asCfscAfaGfCfuuggCfaAfguucususu | 506 |
| 6180 | [GalNAc3][invAb]agaacuUfgCfCfAfAfgcuuggususu | 325 | [Phos]asCfscAfaGfCfuuggCfaAfguucususu | 506 |
| 6274 | [GalNAc3]gaagaacuUfgCfCfAfAfgcuugsgsu | 326 | [Phos]asCfscAfaGfCfuuggCfaAfguucuucsusu | 507 |
| 6172 | [GalNAc3][invAb]gaagaacuUfgCfCfAfAfgcuuggs [invAb] | 327 | [Phos]asCfscAfaGfCfuuggCfaAfguucuucsusu | 507 |
| 6347 | [GalNAc3][invAb]gaagaacuUfgCfCfAfAfgcuugsgsu | 328 | [Phos]asCfscAfaGfCfuuggCfaAfguucuucsusu | 507 |
| 4792 | [GalNAc3]gaacuuGfcCfAfAfGfcuugguusus u | 329 | [Phos]asAfscCfaAfGfcuugGfcAfaguucsusu | 508 |
| 6181 | [GalNAc3][invAb]gaacuuGfcCfAfAfGfcuugguususu | 330 | [Phos]asAfscCfaAfGfcuugGfcAfaguucsusu | 508 |
| 6348 | [GalNAc3]aagaacuuGfcCfAfAfGfcuuggsusu | 331 | [Phos]asAfscCfaAfGfcuugGfcAfaguucuususu | 509 |
| 6173 | [GalNAc3][invAb]aagaacuuGfcCfAfAfGfcuuggus [invAb] | 332 | [Phos]asAfscCfaAfGfcuugGfcAfaguucuususu | 509 |
| 6235 | [GalNAc3][invAb]aagaacuuGfcCfAfAfGfcuuggsusu | 333 | [Phos]asAfscCfaAfGfcuugGfcAfaguucuususu | 509 |
| 4818 | [GalNAc3]acaccaGfcAfUfAfGfucggacusus u | 334 | [Phos]asGfsuCfcGfAfcuauGfcUfggugususu | 510 |
| 5129 | [GalNAc3]caccagCfaUfAfGfUfcggaccusus u | 335 | [Phos]asGfsgUfcCfGfacuaUfgCfuggugsusu | 511 |
| 4705 | [GalNAc3]cgcccuUfgGfUfGfUfuacaccasus u | 336 | [Phos]usGfsgUfgUfAfacacCfaAfgggcgsusu | 512 |
| 8336 | [GalNAc3][invAb]uucgcccuUfgGfUfGfUfuacacscsa | 337 | usGfsguguAfacacCfaAfgggcgaasusu | 513 |
| 11313 | [GalNAc3]s[invAb]cgcccuUfGfGfUfguuacaccasusu | 338 | usGfsguguAfacacCfaAfgggcgsusu | 514 |
| 11315 | [GalNAc3]scgcccuUfgGfUfGfUfuacaccs[invAb] | 339 | usGfsguguAfacacCfaAfgggcgsusu | 514 |
| 11316 | [GalNAc3]s[invAb]cgcccuUfgGfUfGfUfuacacscsa | 340 | usGfsguguAfacacCfaAfgggcgsusu | 514 |
| 11318 | [GalNAc3]s[invAb]cgcccuUfGfGfUfguuacacscsa | 341 | usGfsguguAfacaccaAfgGfgcgsusu | 515 |
| 11320 | [GalNAc3]suucgccCfuUfGfGfUfguuacaccs[invAb] | 342 | usGfsgUfgUfaacaccaAfgGfgcgaasusu | 516 |

TABLE 2-continued

| Duplex No. | Sense Sequence (5'-3') | SEQ ID NO: | Antisense Sequence (5'-3') | SEQ ID NO: |
|---|---|---|---|---|
| Modified LPA siRNA sequences | | | | |
| 11322 | [GalNAc3]suucgccCfuUfGfGfUfguuacaccs[invAb] | 342 | usGfsguguaAfCfaccaAfgGfgcgaasusu | 517 |
| 4706 | [GalNAc3]gcccuuGfgUfGfUfUfacaccaususu | 343 | [Phos]asUfsgGfuGfUfaacaCfcAfagggcsusu | 518 |
| 8207 | [GalNAc3]sucgcccUfuGfGfUfGfuuacaccas[invAb] | 344 | asUfsgGfuGfuAfAfcaccAfaGfggcgasusu | 519 |
| 8213 | [GalNAc3]sucgcccuuGfgUfGfUfUfacaccas[invAb] | 345 | asUfsggugUfaacaCfcAfagggcgasusu | 520 |
| 8918 | [GalNAc3]sgcccuuGfgUfGfUfUfacaccauus[invAb] | 346 | asUfsggugUfaacaCfcAfagggcsusu | 521 |
| 4800 | [GalNAc3]gguguuAfcAfCfCfAfuggaucususu | 347 | [Phos]asGfsaUfcCfAfugguGfuAfacaccsusu | 522 |
| 4629 | [GalNAc3]gaaucaAfgUfGfUfCfcuugcaasusu | 348 | [Phos]usUfsgCfaAfGfgacaCfuUfgauucsusu | 523 |
| 11372 | [GalNAc3]scagaauCfaAfGfUfGfuccuugcas[invAb] | 349 | usUfsgCfaAfgGfAfcacuUfgAfuucugsusu | 524 |
| 11374 | [GalNAc3]sgaaucaAfgUfGfUfCfcuugcaaus[invAb] | 350 | usUfsgcaaGfgacaCfuUfgauucsusu | 525 |
| 11582 | [GalNAc3]scagaaucaAfgUfGfUfCfcuugcas[invAb] | 351 | usUfsgcaaGfgacaCfuUfgauucugsusu | 526 |
| 17183 | [GalNAc3]s[invAb]gaaucaAfGfUfGfuccuugcaasusu | 352 | usUfsgcaaGfgacaCfuUfgauucsusu | 525 |
| 17194 | [GalNAc3]sgaaucaAfgUfGfUfCfcuugcaaus[invAb] | 350 | usUfsgcaaGfgacaCfuUfgAfuucsusu | 527 |
| 17197 | [GalNAc3]sgaaucaAfgUfGfUfCfcuugcas[invAb] | 353 | usUfsgcaaGfgacaCfuUfgauucsusu | 525 |
| 17198 | [GalNAc3]sgaaucaAfgUfgUfCfcuugcas[invAb] | 354 | usUfsgcaaGfgacaCfuUfgauucsusu | 525 |
| 17201 | [GalNAc3]sgaaucaAfGfUfGfuccuugcas[invAb] | 355 | usUfsgcaaGfgacacuUfgAfuucsusu | 528 |
| 17203 | [GalNAc3]scagaauCfaAfGfUfGfuccuugcas[invAb] | 349 | usUfsgcaaGfgacacuUfgAfuucugsusu | 529 |
| 18434 | [GalNAc3]scagaaucaAfgUfGfUfCfcuugcas[invAb] | 351 | usUfsgcaaGfgacaCfuUfgauucsusg | 530 |
| 18439 | [GalNAc3]scagaaucaagUfGfUfCfcuugcas[invAb] | 356 | uslIfsgCfaAfggacaCfuUfgAfuucsusg | 531 |
| 18444 | [GalNAc3]scagaaucaAfGfUfGfuccuugcas[invAb] | 357 | usUfsgcaaGfgacaCfuUfgauucsusg | 530 |
| 4630 | [GalNAc3]aaucaaGfuGfUfCfCfuugcaacsusu | 358 | [Phos]gsUfsuGfcAfAfggacAfcUfugauususu | 532 |
| 4804 | [GalNAc3]aaucaaGfuGfUfCfCfuugcaausu | 359 | [Phos]asUfsuGfcAfAfggacAfcUfugauususu | 533 |
| 11368 | [GalNAc3]s[invAb]agaaucaaGfuGfUfCfCfuugcaas [invAb] | 360 | asUfsuGfcAfAfggacAfcUfugauucususu | 534 |
| 11370 | [GalNAc3]s[invAb]agaaucaaGfuGfUfCfCfuugcasasu | 361 | asUfsugcaAfggacAfcUfugauucususu | 535 |
| 11580 | [GalNAc3]saaucaaGfuGfUfCfCfuugcaauus[invAb] | 362 | asUfsugcaAfggacAfcUfugauususu | 536 |
| 17184 | [GalNAc3]s[invAb]aaucaaGfUfGfUfccuugcaaususu | 363 | asUfsugcaAfggacAfcUfugauususu | 536 |
| 17187 | [GalNAc3]saaucaaGfuGfUfCfCfuugcaauus[invAb] | 362 | asUfsugcaAfggacAfcUfuGfauususu | 537 |
| 17188 | [GalNAc3]saaucaaGfuGfuCfCfuugcaas[invAb] | 364 | asUfsugcaAfggacAfcUfugauususu | 536 |
| 17189 | [GalNAc3]sagaaucAfaGfuGfUfccuugcaas[invAb] | 365 | asUfsugcaAfggacAfcUfuGfauucususu | 538 |
| 17190 | [GalNAc3]saaucaaGfuGfuCfCfuugcaauus[invAb] | 366 | asUfsugcaAfggacAfcUfugauususu | 536 |
| 17191 | [GalNAc3]saaucaaGfuGfUfccuugcaas[invAb] | 367 | asUfsugcaAfggacAfcUfuGfauususu | 537 |
| 17192 | [GalNAc3]saaucaaGfUfGfUfccuugcaauus[invAb] | 368 | asUfsugcaAfggacacUfuGfauususu | 539 |
| 17193 | [GalNAc3]saaucaaGfUfGfUfccuugcaas[invAb] | 369 | asUfsugcaAfggacacUfuGfauususu | 539 |
| 18436 | [GalNAc3]sagaaucaaGfuGfUfCfCfuugcaas[invAb] | 370 | asUfsugcaAfggacAfcUfugauuscsu | 540 |
| 18442 | [GalNAc3]sagaaucaaguGfUfCfCfuugcaas[invAb] | 371 | asUfsuGfcAfaggacAfcUfuGfauuscsu | 541 |
| 18446 | [GalNAc3]sagaaucaaGfUfGfUfccuugcaas[invAb] | 372 | asUfsugcaAfggacAfcUfugauuscsu | 540 |
| 4805 | [GalNAc3]ucaaguGfuCfCfUfUfgcaacuususu | 373 | [Phos]asAfsgUfuGfCfaaggAfcAfcuugasusu | 542 |

TABLE 2-continued

| Modified LPA siRNA sequences | | | | |
|---|---|---|---|---|
| Duplex No. | Sense Sequence (5'-3') | SEQ ID NO: | Antisense Sequence (5'-3') | SEQ ID NO: |
| 4823 | [GalNAc3]cuucugAfaGfAfAfGfcaccaaususu | 374 | [Phos]asUfsuGfgUfGfcuucUfuCfagaagsusu | 543 |
| 6093 | [GalNAc3]uucugaAfgAfAfGfCfaccaacasusu | 375 | [Phos]usGfsuUfgGfUfgcuuCfuUfcagaasusu | 544 |
| 5137 | [GalNAc3]ucuuggUfcCfUfCfUfaugacausu su | 376 | [Phos]asUfsgUfcAfUfagagGfaCfcaagasusu | 545 |
| 8395 | [GalNAc3]sagucuuGfgUfCfCfUfcuaugacas[invAb] | 377 | asUfsgUfcAfuAfGfaggaCfcAfagacususu | 546 |
| 8401 | [GalNAc3]sagucuuggUfcCfUfCfUfaugacas[invAb] | 378 | asUfsgucaUfagagGfaCfcaagacususu | 547 |
| 11337 | [GalNAc3]s[invAb]ucuuggUfCfCfUfcuaugacaususu | 379 | asUfsgucaUfagagGfaCfcaagasusu | 548 |
| 11338 | [GalNAc3]sucuuggUfcCfUfCfUfaugacauus[invAb] | 380 | asUfsgucaUfagaggaCfcAfagasusu | 549 |
| 11340 | [GalNAc3]s[invAb]ucuuggUfcCfUfCfUfaugacsasu | 381 | asUfsgucaUfagagGfaCfcaagasusu | 548 |
| 11341 | [GalNAc3]sucuuggUfcCfUfCfUfaugacas[invAb] | 382 | asUfsgucaUfagaggaCfcAfagasusu | 549 |
| 11342 | [GalNAc3]s[invAb]ucuuggUfCfCfUfcuaugacsasu | 383 | asUfsgucaUfagaggaCfcAfagasusu | 549 |
| 11344 | [GalNAc3]sagucuuGfgUfCfCfUfcuaugacas[invAb] | 377 | asUfsgUfcAfuagaggaCfcAfagacususu | 550 |
| 5134 | [GalNAc3]ugacacCfaCfAfCfUfggcaucasusu | 384 | [Phos]usGfsaUfgCfCfagugUfgGfugucasusu | 551 |
| 11835 | [GalNAc3]sgacaacAfgAfAfUfAfuuauccaus[invAb] | 385 | usGfsgauaAfuauuCfuGfuugucsusu | 552 |
| 4835 | [GalNAc3]gcaaccUfgAfCfAfCfaaugucususu | 386 | [Phos]asGfsaCfaUfUfguguCfaGfguugcsusu | 553 |
| 5102 | [GalNAc3]acacaaUfgUfCfCfAfgugacagsusu | 387 | [Phos]csUfsgUfcAfCfuggaCfaUfugugususu | 554 |
| 6100 | [GalNAc3]acacaaUfgUfCfCfAfgugacaasusu | 388 | [Phos]usUfsgUfcAfCfuggaCfaUfugugususu | 555 |
| 4733 | [GalNAc3]auguccAfgUfGfAfCfagaaucasusu | 389 | [Phos]usGfsaUfuCfUfgucaCfuGfgacausu su | 556 |
| 5105 | [GalNAc3]guccagUfgAfCfAfGfaaucaagsusu | 390 | [Phos]csUfsuGfaUfUfcuguCfaCfuggacsusu | 557 |
| 6101 | [GalNAc3]guccagUfgAfCfAfGfaaucaaasusu | 391 | [Phos]usUfsuGfaUfUfcuguCfaCfuggacsusu | 558 |
| 5106 | [GalNAc3]uccaguGfaCfAfGfAfaucaagususu | 392 | [Phos]asCfsuUfgAfUfucugUfcAfcuggasusu | 559 |
| 5147 | [GalNAc3]ccagugAfcAfGfAfAfucaaguasusu | 393 | [Phos]usAfscUfuGfAfuucuGfuCfacuggsusu | 560 |
| 11379 | [GalNAc3]s[invAb]guccagugAfcAfGfAfAfucaagsusa | 394 | usAfscuugAfuucuGfuCfacuggacsusu | 561 |
| 11838 | [GalNAc3]sguccagUfgAfCfAfGfaaucaagus[invAb] | 395 | usAfscUfuGfaUfUfcuguCfaCfuggacsusu | 562 |
| 11839 | [GalNAc3]sguccagugAfcAfGfAfAfucaagus[invAb] | 396 | usAfscuugAfuucuGfuCfacuggacsusu | 561 |
| 11745 | [GalNAc3]sccagugAfcAfGfAfAfucaaguaus[invAb] | 397 | usAfscuugAfuucuGfuCfacuggsusu | 563 |
| 17185 | [GalNAc3]s[invAb]ccagugAfCfAfGfaaucaaguasusu | 398 | usAfscuugAfuucuGfuCfacuggsusu | 563 |
| 17195 | [GalNAc3]sccagugAfcAfgAfAfucaaguaus[invAb] | 399 | usAfscuugAfuucuGfuCfacuggsusu | 563 |
| 17196 | [GalNAc3]sccagugAfCfAfGfaaucaaguaus[invAb] | 400 | usAfscuugAfuucuguCfaCfuggsusu | 564 |
| 17199 | [GalNAc3]sccagugAfcAfgAfAfucaagus[invAb] | 401 | usAfscuugAfuucuGfuCfacuggsusu | 563 |
| 17200 | [GalNAc3]sccagugAfcAfGfaaucaagus[invAb] | 402 | usAfscuugAfuucuGfuCfaCfuggsusu | 565 |
| 17202 | [GalNAc3]sccagugAfCfAfGfaaucaagus[invAb] | 403 | usAfscuugaUfUfcuguCfaCfuggsusu | 566 |
| 17204 | [GalNAc3]sguccagUfgAfCfAfGfaaucaagus[invAb] | 395 | usAfscuugAfuucuguCfaCfuggacsusu | 567 |
| 17205 | [GalNAc3]sguccagUfgAfcAfGfaaucaagus[invAb] | 404 | usAfscuugAfuucuGfuCfaCfuggacsusu | 568 |
| 18450 | [GalNAc3]sguccagugAfcAfGfAfAfucaagus[invAb] | 396 | usAfscuugAfuucuGfuCfacuggsasc | 569 |
| 18455 | [GalNAc3]sguccagugAfCfAfGfaaucaagus[invAb] | 405 | usAfscuugAfuucuGfuCfacuggsasc | 569 |
| 5116 | [GalNAc3]caccacUfgUfUfAfCfaggaaggsusu | 406 | [Phos]csCfsuUfcCfUfguaaCfaGfuggugsusu | 570 |
| 6102 | [GalNAc3]caccacUfgUfUfAfCfaggaagasusu | 407 | [Phos]usCfsuUfcCfUfguaaCfaGfuggugsusu | 571 |

TABLE 2-continued

| Modified LPA siRNA sequences | | | | |
|---|---|---|---|---|
| Duplex No. | Sense Sequence (5'-3') | SEQ ID NO: | Antisense Sequence (5'-3') | SEQ ID NO: |
| 11743 | [GalNAc3]scagaauAfcUfAfCfCfcaaauggus[invAb] | 408 | usAfscCfaUfuUfGfgguaGfuAfuucugsusu | 572 |
| 5122 | [GalNAc3]cccaaaUfgGfUfGfGfccugaccsusu | 409 | [Phos]gsGfsuCfaGfGfccacCfaUfuugggsusu | 573 |
| 5124 | [GalNAc3]uauaccAfuGfGfAfUfcccagugsusu | 410 | [Phos]csAfscUfgGfGfauccAfuGfguauasusu | 574 |
| 6106 | [GalNAc3]uauaccAfuGfGfAfUfcccaguasusu | 411 | [Phos]usAfscUfgGfGfauccAfuGfguauasusu | 575 |
| 4995 | [GalNAc3]uucugaAfgAfAfGfCfaccaacusus u | 412 | [Phos]asGfsuUfgGfUfgcuuCfuUfcagaasusu | 576 |
| 6182 | [GalNAc3][invAb]uucugaAfgAfAfGfCfaccaacususu | 413 | [Phos]asGfsuUfgGfUfgcuuCfuUfcagaasusu | 576 |
| 6149 | [GalNAc3]ccuucugaAfgAfAfGfCfaccaascsu | 414 | [Phos]asGfsuUfgGfUfgcuuCfuUfcagaaggsusu | 577 |
| 6150 | [GalNAc3][invAb]ccuucugaAfgAfAfGfCfaccaacs [invAb] | 415 | [Phos]asGfsuUfgGfUfgcuuCfuUfcagaaggsusu | 577 |
| 6151 | [GalNAc3]ccuucuGfaAfGfAfAfgcaccaacs[invAb] | 416 | [Phos]asGfsuUfgGfuGfCfuucuUfcAfgaaggsusu | 578 |
| 6152 | [GalNAc3][invAb]ccuucugaAfgAfAfGfCfaccaascsu | 417 | [Phos]asGfsuUfgGfUfgcuuCfuUfcagaaggsusu | 577 |
| 6153 | [GalNAc3][invAb]ccuucugaAfgAfAfGfCfaccaascsu | 417 | [Phos]asGfsuUfggUfgcuuCfuUfcagaaggsusu | 579 |
| 6154 | [GalNAc3][invAb]ccuucugaAfgAfAfGfCfaccaascsu | 417 | [Phos]asGfsuugGfUfgcuuCfuUfcagaaggsusu | 580 |
| 6155 | [GalNAc3][invAb]ccuucugaAfgAfAfGfCfaccaascsu | 417 | [Phos]asGfsuuggUfgcuuCfuUfcagaaggsusu | 581 |
| 6156 | [GalNAc3][invAb]ccuucugaAfgAfAfGfCfaccaascsu | 417 | [Phos]asGfsuUfgGfUfgcUfuCfuUfcagaaggsusu | 582 |
| 7915 | [GalNAc3]s[invAb]uucugaAfgAfAfGfCfaccaacususu | 418 | asGfsuUfgGfUfgcuuCfuUfcagaasusu | 583 |
| 7919 | [GalNAc3]sccuucugaAfgAfAfGfCfaccaacs[invAb] | 419 | asGfsuUfgGfUfgcuuCfuUfcagaaggsusu | 584 |
| 7922 | [GalNAc3]s[invAb]ccuucugaAfgAfAfGfCfaccaascsu | 420 | asGfsuUfgGfUfgcUfuCfuUfcagaaggsusu | 585 |
| 5049 | [GalNAc3]CfuGfaAfgAfaGfCfAfCfcaAfcUfgAfsusUf | 421 | [Phos]usCfsaGfuUfGfgugcUfuCfuUfcAfgsUfsu | 586 |
| 4849 | [GalNAc3]agcaccAfaCfUfGfAfaaacagusus u | 422 | [Phos]asCfsuGfuUfUfucagUfuGfgugcusus u | 587 |
| 11836 | [GalNAc3]s[invAb]gaagcaccAfaCfUfGfAfaaacags [invAb] | 423 | asCfsuGfuUfUfucagUfuGfgugcuucsusu | 588 |
| 6109 | [GalNAc3]cccgguUfcCfAfAfGfcacagaasusu | 424 | [Phos]usUfscUfgUfGfcuugGfaAfccgggsusu | 589 |
| 6110 | [GalNAc3]agcacaGfaGfGfCfUfccuucuasusu | 425 | [Phos]usAfsgAfaGfGfagccUfcUfgugcusus u | 590 |
| 4815 | [GalNAc3]ccuucuGfaAfCfAfAfgcaccacsusu | 426 | [Phos]gsUfsgGfuGfCfuuguUfcAfgaaggsusu | 591 |
| 4852 | [GalNAc3]ccuucuGfaAfCfAfAfgcaccausus u | 427 | [Phos]asUfsgGfuGfCfuuguUfcAfgaaggsusu | 592 |
| 6113 | [GalNAc3]ucagaaAfcAfGfAfAfucagguasusu | 428 | [Phos]usAfscCfuGfAfuucuGfuUfucugasusu | 593 |
| 5142 | [GalNAc3]cagaauCfaGfGfUfGfuccuagasusu | 429 | [Phos]usCfsuAfgGfAfcaccUfgAfuucugsusu | 594 |
| 4861 | [GalNAc3]guuaucGfaGfGfCfAfcauucuusus u | 430 | [Phos]asAfsgAfaUfGfugccUfcGfauaacsusu | 595 |
| 5015 | [GalNAc3]uuaucgAfgGfCfAfCfauucuccsusu | 431 | [Phos]gsGfsaGfaAfUfgugcCfuCfgauaasusu | 596 |
| 4862 | [GalNAc3]uuaucgAfgGfCfAfCfauucucusus u | 432 | [Phos]asGfsaGfaAfUfgugcCfuCfgauaasusu | 597 |
| 6115 | [GalNAc3]acgcgaUfgCfUfCfAfgacacaasusu | 433 | [Phos]usUfsgUfgUfCfugagCfaUfcgcgusus u | 598 |
| 6116 | [GalNAc3]agacacAfgAfAfGfGfgacuguasusu | 434 | [Phos]usAfscAfgUfCfccuuCfuGfugucusus u | 599 |
| 6117 | [GalNAc3]uguccuGfgAfAfGfCfauuguaasusu | 435 | [Phos]usUfsaCfaAfUfgcuuCfcAfggacasusu | 600 |
| 5140 | [GalNAc3]aacaagGfuUfUfGfGfaaagcausus u | 436 | [Phos]asUfsgCfuUfUfccaaAfcCfuuguusus u | 601 |
| 20022 | [GalNAc3]scgcccuUfgGfuGfUfuacaccaus[invAb] | 612 | usGfsguguAfacacCfaAfgggcgsusu | 514 |
| 20027 | [GalNAc3]suucgccCfuUfgGfUfguuacaccs[invAb] | 613 | usGfsguguAfacacCfaAfgGfgcgaasusu | 617 |
| 20033 | [GalNAc3]scgcccuUfgGfUfguuacaccs[invAb] | 614 | usGfsguguAfacacCfaAfgGfgcgsusu | 618 |

TABLE 2-continued

| Modified LPA siRNA sequences | | | | |
|---|---|---|---|---|
| Duplex No. | Sense Sequence (5'-3') | SEQ ID NO: | Antisense Sequence (5'-3') | SEQ ID NO: |
| 20040 | [GalNAc3]suucgcccuUfGfGfUfguuacaccs[invAb] | 615 | usGfsguguAfacacCfaAfgggcgsasa | 619 |
| 20047 | [GalNAc3]suucgcccuUfgGfUfGfUfuacaccs[invAb] | 616 | usGfsguguAfacacCfaAfgggcgsasa | 619 |

Example 2. In Vitro Evaluation of LPA RNAi Constructs in Cell-Based Assays

Initially, 400 GalNAc-conjugated LPA siRNA molecules, which were based on 320 different sequences prioritized from the bioinformatics analysis described in Example 1, were evaluated at a single concentration (12 nM) for inhibition of LPA mRNA synthesis in an in vitro primary human hepatocyte assay. Following the manufacturers protocol, human primary hepatocyte cells (Xenotech/Sekisui donor lot #HC10-23) were thawed in OptiThaw media (Xenotech cat #K8000). Cells were centrifuged and post media aspiration, resuspended in OptiPlate hepatocyte media (Xenotech cat #K8200) and plated into 96 well collagen coated plates (Greiner cat #655950). Following a 3-4 hour incubation period, media was removed and replaced with OptiCulture hepatocyte media (Xenotech cat #K8300). 3-5 hours following the addition of OptiCulture media, GalNAc-conjugated siRNAs were delivered to cells via free uptake (no transfection reagent) in either single point (12 nM) or dose response format (0.2 μM to 4 μM). Cells were incubated approximately 66-72 hours at 37° C. and 5% $CO_2$. RNA extraction was performed on either a Qiagen QIACube HT (9001793) or a ThermoFisher KingFisher Flex (5400630) instrument. Using the Qiagen QIACube HT system, cells were lysed with Qiagen RLT buffer (79216)+1% 2-mercaptoethanol (Sigma, M-3148), and the lysates were stored at −20° C. RNA was purified using a Qiagen QIACube HT Kit (74171) on the Qiagen QIACube HT instrument according to manufacturer's instructions. Samples were analyzed using a QIAxpert system (9002340). Using the ThermoFisher KingFisher Flex system, cells were lysed using lysis/binding concentrate (ThermoFisher Scientific AM8500). Cell lysates were stored at −20° C. or in some cases, RNA extraction was performed immediately after cell lysis. RNA was purified using a ThermoFisher Scientific MagMAX™-96 Total RNA Isolation Kit (ThermoFisher Scientific AM1830) on a KingFisher Flex instrument according to manufacturer's instructions.

cDNA was synthesized from RNA samples using the Applied Biosystems High Capacity cDNA Reverse Transcription kit (4368813), reactions were assembled according to manufacturer's instructions, input RNA concentration varied by sample. Reverse transcription was carried out on a BioRad tetrad thermal cycler (model #PTC-0240G) under the following conditions: 25° C. 10 minutes, 37° C. 120 minutes, 85° C. 5 minutes followed by (an optional) 4° C. infinite hold. Droplet digital PCR (ddPCR) was performed using BioRad's QX200 AutoDG droplet digital PCR system according to manufacturer's instructions. Reactions were assembled into an Eppendorf clear 96 well PCR plate (951020303) using BioRad ddPCR Supermix for Probes (1863010), fluorescently labeled qPCR assays for LPA (IDT Hs.PT.58.1145110, ordered with primer to probe ratio 3.6:1, 45 nanomoles each forward and reverse primer, 12.5 nanomoles 6-FAM/ZEN/IBFQ labeled probe) and TATA Box binding protein (TBP) (IDT Hs.PT.53a.20105486, ordered with primer to probe ratio 3.6:1, 45 nanomoles each forward and reverse primer, 12.5 nanomoles HEX/ZEN/IBFQ labeled probe) and RNase free water (Ambion, AM9937). Primer/probe sequences are shown below. Final primer/probe concentration was 900 nM/250 nM respectively, input cDNA concentration varied among wells.

Droplets were formed using a BioRad Auto DG droplet generator (1864101) set up with manufacturer recommended consumables (BioRad DG32 cartridges 1864108, BioRad tips 1864121, Eppendorf blue 96well PCR plate 951020362, BioRad droplet generation oil for probes 1864110 and a BioRad droplet plate assembly). Droplets were amplified on a BioRad C1000 touch thermal cycler (1851197) using the following conditions: enzyme activation 95° C. 10 minutes, denaturation 94° C. 30 seconds followed by annealing/extension 60° C. for one minute, 40 cycles using a 2° C./second ramp rate, enzyme deactivation 98° C. 10 minutes followed by (an optional) 4° C. infinite hold. Samples were then read on a BioRad QX200 Droplet Reader measuring FAM/HEX signal that correlated to LPA or TBP mRNA concentration, respectively. Data was analyzed using BioRad's QuantaSoft software package. Samples were gated by channel (fluorescent label) to determine the concentration per sample. Each sample was then expressed as the ratio of the concentration of the gene of interest (LPA)/concentration of the housekeeping gene (TBP) to control for differences in sample loading. Data was then imported into Genedata Screener, where each test siRNA was normalized to the median of the neutral control wells (buffer only or control siRNA) and was expressed as the POC (percent of control).

```
ddPCR Assay Sequences
LPA:
Primer 1:
5'-CAAAATGGAACATAAGGAAGTGGT-3' (SEQ ID NO: 602)

Primer 2:
5'-GTGACAGTGGTGGAGTACG-3' (SEQ ID NO: 603)

Probe:
5'-/56-FAM/CATGGCTTT (SEQ ID NO: 604)/ZEN/

GCTCAGGTGCTGC (SEQ ID NO: 605)/3IABkFQ/-3'

TBP:
Primer 1:
5'-ATGACCCCCATCACTCCT-3' (SEQ ID NO: 606)

Primer 2:
5'-TCAAGTTTACAACCAAGATTCACTG-3' (SEQ ID NO: 607)

Probe:
5'-/5HEX/AGCTGCGGT (SEQ ID NO: 608)/ZEN/

ACAATCCCAGAACTC (SEQ ID NO: 609)/3IABkFQ/-3'
```

Based on the results of the single concentration assay, a subset of the GalNAc-conjugated LPA siRNA molecules was selected for further testing in a 10-point dose response format (0.2 μM to 4 μM) of the ddPCR assay in primary human hepatocytes. The ratio of the concentration of LPA mRNA to the concentration of TBP mRNA was measured after a 72-hour incubation period of the GalNAc-conjugated LPA siRNA molecules with the hepatocytes. EC50 values for each of the GalNAc-conjugated LPA siRNA molecules were calculated from the dose-response curves and are shown in Table 3 below along with the maximum antagonist activity for each molecule expressed as percent of LPA mRNA remaining (i.e. percent of control).

TABLE 3

In vitro inhibition of LPA mRNA in primary human hepatocytes

| Duplex No. | EC50 (nM) | Max Antagonist Activity (% LPA mRNA remaining) |
|---|---|---|
| 4599 | 92.1 | 35.0 |
| 4601 | 2.4 | 9.8 |
| 4613 | 14.6 | 15.0 |
| 4629 | 68.3 | 34.2 |
| 4630 | 2.98 | 20.0 |
| 4683 | 14.7 | 17.5 |
| 4733 | 82.7 | 43.7 |
| 4776 | 6.39 | 2.4 |
| 4778 | 6.22 | 30.0 |
| 4792 | 71.9 | 12.8 |
| 4804 | 24.6 | 4.7 |
| 4805 | 2.2 | 40.8 |
| 4815 | 1.57 | 27.0 |
| 4816 | 1.44 | 7.1 |
| 4818 | 49.5 | 63.5 |
| 4823 | 146 | 25.9 |
| 4849 | — | 77.6 |
| 4852 | 61.1 | 35.9 |
| 4861 | — | 48.8 |
| 4862 | 13.7 | 26.7 |
| 4932 | 8.54 | 14.5 |
| 4938 | 10.6 | 4.3 |
| 4941 | 9.53 | 4.7 |
| 4948 | 99.1 | 35.3 |
| 4956 | 7.17 | 3.8 |
| 4961 | 3.74 | 18.1 |
| 4966 | 19.9 | 4.1 |
| 4967 | 20.5 | 9.3 |
| 4969 | 87 | 13.0 |
| 4970 | 37.5 | 21.0 |
| 4971 | 3.71 | 18.3 |
| 4972 | 16.1 | 40.9 |
| 4973 | 11.8 | 5.5 |
| 4978 | 20.3 | 2.1 |
| 4984 | 7.25 | 14.3 |
| 4995 | 1.9 | 20.7 |
| 5015 | 7.79 | 16.5 |
| 5037 | 56.8 | 41.7 |
| 5042 | 1.38 | 8.3 |
| 5043 | 3.43 | 17.7 |
| 5044 | 101 | 36.5 |
| 5049 | 7.16 | 53.3 |
| 5102 | — | 57.6 |
| 5105 | — | 25.4 |
| 5106 | 108 | 21.7 |
| 5116 | — | 50.0 |
| 5122 | 39.2 | 10.8 |
| 5124 | — | 92.9 |
| 5125 | 157 | 37.2 |
| 5126 | 63.7 | 72.9 |
| 5129 | 836 | 32.1 |
| 5133 | 110 | 67.1 |
| 5134 | — | 66.1 |
| 5137 | 45.3 | 16.4 |
| 5140 | 64.7 | 35.8 |
| 5142 | 315 | 54.7 |
| 5147 | — | 49.6 |

TABLE 3-continued

In vitro inhibition of LPA mRNA in primary human hepatocytes

| Duplex No. | EC50 (nM) | Max Antagonist Activity (% LPA mRNA remaining) |
|---|---|---|
| 5409 | 14.5 | 9.1 |
| 5410 | 2.52 | 6.2 |
| 5413 | 3.06 | 11.3 |
| 5414 | 4.2 | 13.6 |
| 5430 | — | 6.8 |
| 6078 | 28.2 | 18.3 |
| 6079 | 102 | 10.3 |
| 6081 | 63.4 | 24.3 |
| 6084 | 2.95 | 3.8 |
| 6086 | — | 76.6 |
| 6087 | — | 13.0 |
| 6088 | 17.8 | 16.2 |
| 6089 | 7.41 | 17.3 |
| 6091 | 168 | 15.7 |
| 6093 | 16.7 | 7.0 |
| 6101 | 25 | 42.0 |
| 6102 | 311 | 33.0 |
| 6106 | — | 133.3 |
| 6109 | 50.3 | 18.9 |
| 6110 | 49.1 | 30.4 |
| 6113 | 24.2 | 36.7 |
| 6115 | 14.8 | 8.3 |
| 6116 | 262 | 24.8 |
| 6117 | 8.5 | 24.8 |
| 6138 | 5.08 | 7.1 |
| 6139 | — | 8.7 |
| 6140 | 8.32 | 5.0 |
| 6141 | 2.05 | 4.4 |
| 6143 | 5.06 | 6.1 |
| 6144 | 5.06 | 6.6 |
| 6145 | 18.2 | 10.5 |
| 6146 | — | 7.1 |
| 6147 | — | 8.3 |
| 6148 | 5.04 | 21.2 |
| 6150 | 18.1 | 18.1 |
| 6151 | 28.1 | 19.5 |
| 6153 | 42.1 | 20.1 |
| 6154 | 5.45 | 8.8 |
| 6155 | 37.9 | 17.1 |
| 6156 | 22.5 | 13.0 |
| 6172 | 2.63 | 21.3 |
| 6173 | 121 | 5.6 |
| 6174 | 4.73 | 21.9 |
| 6180 | — | 17.5 |
| 6181 | 4.02 | 11.3 |
| 6183 | 66 | 7.5 |
| 6235 | 2.81 | 14.1 |
| 6236 | 27.1 | 8.3 |
| 6244 | 5.11 | 19.5 |
| 6245 | 19.9 | 9.7 |
| 6246 | 33.4 | 11.7 |
| 6248 | 5.77 | 18.6 |
| 6249 | 4.16 | 3.7 |

Several of the LPA siRNA molecules exhibited maximum reductions of LPA mRNA levels over 85% relative to hepatocytes not treated with the siRNA molecules and had EC50 values in the single-digit nanomolar range.

A subset of the more potent siRNA molecules from Table 3 were selected and further tested in a second in vitro assay, which employed a dual luciferase reporter system. In addition, the dual luciferase reporter assay was used in combination with the transgenic mouse model described in Example 3 for the SAR studies, in which the placement and number of chemical modifications and/or the format of the siRNA molecule (e.g. length of strands and nature of the ends) was altered for select sequence families to optimize the magnitude and duration of inhibition of LPA gene expression.

The dual luciferase reporter plasmid (pMIR0660) was constructed from the commercially-available psiCHECK plasmid (Promega, Madison, WI), which comprises coding DNA sequences (CDS) for both *Renilla* luciferase and firefly luciferase. The portion of the human LPA CDS containing KIV-3 to KIV-10 was cloned into the plasmid to create a fusion of the *Renilla* luciferase CDS with the human LPA CDS. siRNA-mediated inhibition of translation of the LPA target sequence caused degradation of the fusion mRNA and a decrease in the *Renilla* luciferase signal. LPA gene knockdown was assessed by measuring *Renilla* luciferase levels normalized to the levels of firefly luciferase, which is constitutively expressed by the plasmid. Huh7 cells, a human hepatocellular carcinoma cell line, were plated in 96-well plates. After overnight incubation, cells were co-transfected with dual reporter plasmid pMIR0660 and the test siRNA molecule at different concentrations with Lipofectamine™ 2000 Transfection Reagent per manufacturer's instructions. An 8- to 11-point dose titration (0-10 nM) was performed (in triplicate). Dual luciferase activity was measured after a second overnight incubation on the Envision luminometer (Perkin Elmer, Waltham, MA). EC50 values and maximum antagonist activity (measured as the lowest ratio of *Renilla* luciferase level to firefly luciferase level) for each of the evaluated LPA siRNA molecules are reported in Table 4 below.

TABLE 4

Efficacy of LPA RNAi constructs in dual luciferase reporter assay in Huh7 cells

| Duplex No. | EC50 (pM) | Max Antagonist Activity (normalized Renilla luciferase-LPA expression level) |
|---|---|---|
| 4601 | 1.1 | 0.24 |
| 4613 | 10.4 | 0.04 |
| 4614 | 61.3 | 0.51 |
| 4683 | 1.1 | 0.27 |
| 4705 | 9.9 | 0.36 |
| 4706 | 1.7 | 0.39 |
| 4776 | 5.6 | 0.08 |
| 4792 | 7.4 | 0.22 |
| 4800 | 57.8 | 0.42 |
| 4804 | 0.5 | 0.21 |
| 4815 | 1.9 | 0.14 |
| 4816 | 10.1 | 0.18 |
| 4818 | 0.6 | 0.27 |
| 4823 | 1.6 | 0.17 |
| 4835 | 27.7 | 0.34 |
| 4852 | 6.9 | 0.09 |
| 4862 | 0.7 | 0.14 |
| 4930 | 12.8 | 0.44 |
| 4941 | 29.4 | 0.17 |
| 4956 | 9.8 | 0.19 |
| 4966 | — | 0.59 |
| 4970 | 6.4 | 0.47 |
| 4971 | 11.1 | 0.33 |
| 4972 | | 0.67 |
| 4973 | 15.1 | 0.42 |
| 4978 | 10.5 | 0.19 |
| 4995 | 35.5 | 0.29 |
| 5043 | 0.8 | 0.21 |
| 5137 | 64.4 | 0.24 |
| 5417 | — | 0.67 |
| 5433 | 11.8 | 0.29 |
| 6149 | 12.6 | 0.48 |
| 6150 | 10.5 | 0.23 |
| 6152 | 16.6 | 0.47 |
| 6182 | 7.9 | 0.15 |
| 6247 | 28.2 | 0.25 |
| 6248 | 10.2 | 0.28 |
| 6249 | 17.9 | 0.14 |
| 6274 | 2.4 | 0.46 |
| 6276 | 5.9 | 0.36 |
| 6277 | 12.3 | 0.42 |
| 6278 | 8.6 | 0.43 |

TABLE 4-continued

Efficacy of LPA RNAi constructs in dual luciferase reporter assay in Huh7 cells

| Duplex No. | EC50 (pM) | Max Antagonist Activity (normalized Renilla luciferase-LPA expression level) |
|---|---|---|
| 6279 | 6.2 | 0.15 |
| 6280 | 49.8 | 0.37 |
| 6281 | 17.0 | 0.40 |
| 6282 | 14.3 | 0.34 |
| 6347 | 4.2 | 0.55 |
| 6348 | 13.4 | 0.49 |
| 7900 | 19.2 | 0.26 |
| 7902 | 12.5 | 0.22 |
| 7915 | 60.2 | 0.29 |
| 7919 | 17.1 | 0.28 |
| 7922 | 10.7 | 0.33 |
| 7932 | 43.0 | 0.43 |
| 7934 | 44.0 | 0.42 |
| 7936 | 7.2 | 0.45 |
| 7938 | 32.7 | 0.37 |
| 8207 | 8.1 | 0.47 |
| 8213 | 5.0 | 0.78 |
| 8278 | 14.0 | 0.35 |
| 8336 | 106.0 | 0.35 |
| 8395 | 4.0 | 0.42 |
| 8401 | 2.6 | 0.45 |
| 8918 | 27.0 | 0.39 |
| 10927 | 83.9 | 0.37 |
| 11313 | 88.0 | 0.31 |
| 11315 | 487.0 | 0.49 |
| 11316 | 140.0 | 0.46 |
| 11318 | 17.0 | 0.33 |
| 11320 | 37.0 | 0.32 |
| 11322 | 56.7 | 0.46 |
| 11337 | 15.0 | 0.36 |
| 11338 | 320.0 | 0.45 |
| 11340 | 123.0 | 0.43 |
| 11341 | 206.0 | 0.41 |
| 11342 | 67.0 | 0.35 |
| 11344 | 41.0 | 0.33 |
| 11347 | 124.0 | 0.45 |
| 11348 | 82.0 | 0.33 |
| 11349 | 122.0 | 0.35 |
| 11350 | 95.0 | 0.37 |
| 11351 | 35.0 | 0.33 |
| 11352 | 65.4 | 0.40 |
| 11354 | 16.0 | 0.30 |
| 11356 | 13.0 | 0.33 |
| 11357 | 55.8 | 0.32 |
| 11368 | 2.0 | 0.33 |
| 11370 | 126.0 | 0.43 |
| 11372 | 80.0 | 0.44 |
| 11374 | 257.0 | 0.46 |
| 11379 | 125.0 | 0.52 |
| 11580 | 37.0 | 0.41 |
| 11582 | 11.0 | 0.43 |
| 11741 | 164.0 | 0.47 |
| 11743 | 10.0 | 0.39 |
| 11745 | 214.0 | 0.45 |
| 11835 | 403.0 | 0.54 |
| 11836 | 96.0 | 0.61 |
| 11838 | 42.2 | 0.56 |
| 11839 | 1.7 | 0.43 |
| 17183 | 39 | 0.34 |
| 17184 | 2.7 | 0.28 |
| 17185 | 58 | 0.33 |
| 17187 | 41 | 0.34 |
| 17188 | 5.5 | 0.27 |
| 17189 | 7.4 | 0.28 |
| 17190 | 23 | 0.25 |
| 17191 | 6 | 0.30 |
| 17192 | 23.8 | 0.33 |
| 17193 | 11.95 | 0.20 |
| 17194 | 105 | 0.33 |
| 17195 | 81.5 | 0.33 |
| 17196 | 211 | 0.34 |
| 17197 | 16 | 0.30 |
| 17198 | 0.7 | 0.36 |

TABLE 4-continued

| Efficacy of LPA RNAi constructs in dual luciferase reporter assay in Huh7 cells | | |
|---|---|---|
| Duplex No. | EC50 (pM) | Max Antagonist Activity (normalized Renilla luciferase-LPA expression level) |
| 17199 | 9 | 0.34 |
| 17200 | 1.1 | 0.27 |
| 17201 | 1.5 | 0.19 |
| 17202 | 6.2 | 0.60 |
| 17203 | 8.9 | 0.34 |
| 17204 | 125 | 0.37 |
| 17205 | 41 | 0.20 |
| 18434 | 4.62 | 0.32 |
| 18436 | 5.77 | 0.35 |
| 18439 | 36 | 0.32 |
| 18442 | 115 | 0.39 |
| 18444 | 8.19 | 0.32 |
| 18446 | 0.736 | 0.30 |
| 18448 | 7.13 | 0.21 |
| 18450 | 6.91 | 0.29 |
| 18455 | 5.73 | 0.36 |

Example 3. In Vivo Efficacy of LPA RNAi Constructs in Transgenic Mice Expressing Human Apolipoprotein(a)

To assess the efficacy of the LPA RNAi constructs in vivo, a double transgenic mouse model was used. There is no ortholog to the LPA gene in mice and apo(a) (encoded by the LPA gene) is generally expressed only in primates. Transgenic mice expressing human apo(a) from a yeast artificial chromosome (YAC) containing the full human LPA gene (Frazer et al., Nature Genetics, Vol. 9: 424-431, 1995) were crossed with transgenic mice expressing human apoB-100 (Linton et al., J. Clin. Invest., Vol. 92: 3029-3037, 1993). The resultant double transgenic mice express a fully functional human Lp(a) particle with serum baseline Lp(a) levels of about 50-60 mg/dL on average. Female double transgenic mice were randomized to different treatment groups in each study based on baseline Lp(a) serum levels, body weight, and age. Saline or LPA RNAi constructs were administered as a single subcutaneous injection at a dose of 0.5 mg/kg, 1 mg/kg, or 2 mg/kg. Serum samples were taken prior to injection and then post injection at weeks 1, 2, 3, 4, 6, 8, 10, and 12 or until serum Lp(a) levels returned to baseline levels. Lp(a) concentrations were measured in the serum using an Lp(a) ELISA assay (Cat. #10-1106-01, Mercodia AB, Uppsala, Sweden). A percentage change in Lp(a) level for each animal at a particular time point was calculated based on that animal's baseline Lp(a) level. Results of eleven separate studies in the transgenic mice with different LPA RNAi constructs are shown in Tables 5-15 below. Data are expressed as average percent change from baseline for each treatment group (n=4 or 5 animals/group, except for Studies 10 and 11 where n=6 animals/group).

TABLE 5

| Serum Lp(a) levels in double transgenic mice following administration of LPA RNAi constructs at 2 mg/kg - Study 1 | | | | |
|---|---|---|---|---|
| | Average Percent Change in Serum Lp(a) from Baseline | | | |
| Treatment | Week 1 | Week 2 | Week 3 | Week 4 |
| Saline | +72% | +29% | +56% | +69% |
| 4601 | −92% | −95% | −90% | −76% |
| 4613 | −85% | −92% | −85% | −62% |
| 4683 | −51% | −46% | +23% | +49% |
| 4792 | −59% | −47% | +33% | +54% |
| 4804 | +10% | +13% | +75% | +103% |
| 4970 | −14% | −76% | −64% | −59% |
| 4971 | −47% | −50% | −8% | +56% |
| 4973 | −66% | −73% | −50% | +16% |
| 4995 | −70% | −70% | −26% | +14% |
| 5042 | −77% | −81% | −52% | +46% |
| 5043 | −83% | −79% | −40% | −20% |

TABLE 6

| Serum Lp(a) levels in double transgenic mice following administration of LPA RNAi constructs at 2 mg/kg - Study 2 | | | |
|---|---|---|---|
| | Average Percent Change in Serum Lp(a) from Baseline | | |
| Treatment | Week 1 | Week 2 | Week 4 |
| Saline | −12% | −20% | +10% |
| 4966 | −81% | −83% | −19% |
| 6150 | −92% | −93% | −83% |
| 6182 | −87% | −82% | −45% |
| 6247 | −93% | −95% | −86% |
| 6248 | −73% | −77% | −37% |
| 6249 | −89% | −89% | +2% |

TABLE 7

| Serum Lp(a) levels in double transgenic mice following administration of LPA RNAi constructs at 0.5 mg/kg - Study 3 | | |
|---|---|---|
| | Average Percent Change in Serum Lp(a) from Baseline | |
| Treatment | Week 2 | Week 4 |
| Saline | −30% | −4% |
| 5417 | −37% | +6% |
| 5433 | −16% | −6% |
| 6276 | −66% | −20% |
| 6277 | −86% | −22% |
| 6279 | −26% | +25% |
| 6280 | −65% | −21% |
| 6282 | −70% | −32% |

TABLE 8

| Serum Lp(a) levels in double transgenic mice following administration of LPA RNAi constructs at 2 mg/kg - Study 4 | | | |
|---|---|---|---|
| | Average Percent Change in Serum Lp(a) from Baseline | | |
| Treatment | Week 2 | Week 3 | Week 4 |
| Saline | +28% | +35 | 0% |
| 4705 | −61% | −66% | −45% |
| 4930 | −88% | −79% | −67% |
| 5137 | −62% | −52% | −46% |

TABLE 9

Serum Lp(a) levels in double transgenic mice following administration of LPA RNAi constructs at 1 mg/kg - Study 5

| Treatment | Average Percent Change in Serum Lp(a) from Baseline | | |
|---|---|---|---|
| | Week 2 | Week 3 | Week 4 |
| Saline | +69% | +93% | +105% |
| 4706 | +12% | −13% | −13% |
| 8207 | +28% | +16% | +33% |
| 8213 | 0% | 0% | +27% |
| 8336 | −39% | −59% | −16% |
| 8395 | −79% | −84% | −59% |
| 8918 | +1% | +18% | +22% |

TABLE 10

Serum Lp(a) levels in double transgenic mice following administration of LPA RNAi constructs at 1 mg/kg - Study 6

| Treatment | Average Percent Change in Serum Lp(a) from Baseline | | |
|---|---|---|---|
| | Week 2 | Week 3 | Week 4 |
| Saline | +23% | +50% | +45% |
| 7934 | −77% | −76% | −28% |
| 7938 | −64% | −73% | +1% |
| 11313 | −51% | −54% | +3 |
| 11318 | −64% | −81% | −64% |
| 11351 | −85% | −89% | −68% |
| 11368 | −48% | −55% | +22% |
| 11372 | −72% | −75% | −13% |
| 11379 | −83% | −81% | −20% |

TABLE 11

Serum Lp(a) levels in double transgenic mice following administration of LPA RNAi constructs at 1 mg/kg - Study 7

| Treatment | Average Percent Change in Serum Lp(a) from Baseline | | |
|---|---|---|---|
| | Week 2 | Week 3 | Week 4 |
| Saline | −12% | −19% | +60% |
| 8401 | −90% | −82% | −58% |
| 10927 | −92% | −85% | −77% |
| 11315 | −74% | −46% | −12% |
| 11344 | −87% | −75% | −67% |
| 11356 | −75% | −60% | −23% |
| 11580 | −91% | −73% | −31% |
| 11741 | −70% | −42% | −11% |
| 11743 | −64% | −19% | −8% |

TABLE 12

Serum Lp(a) levels in double transgenic mice following administration of LPA RNAi constructs at 1 mg/kg - Study 8

| Treatment | Average Percent Change in Serum Lp(a) from Baseline | | |
|---|---|---|---|
| | Week 2 | Week 3 | Week 4 |
| Saline | +73% | +99% | +82% |
| 11320 | −61% | −43% | −34% |
| 11370 | −18% | +41% | +51% |
| 11374 | −74% | −54% | −47% |
| 11580 | −86% | −78% | −74% |
| 11582 | −50% | +1% | 0% |
| 11745 | −50% | −15% | +23% |

TABLE 13

Serum Lp(a) levels in double transgenic mice following administration of LPA RNAi constructs at 1 mg/kg - Study 9

| Treatment | Average Percent Change in Serum Lp(a) from Baseline | | |
|---|---|---|---|
| | Week 2 | Week 3 | Week 4 |
| Saline | −5% | +21% | +9% |
| 17183 | −56% | −37% | −16% |
| 17190 | −81% | −69% | −49% |
| 17205 | −59% | −40% | −46% |
| 18436 | −87% | −80% | −63% |
| 18444 | −75% | −70% | −44% |
| 18455 | −43% | −35% | −21% |

TABLE 14

Serum Lp(a) levels in double transgenic mice following administration of LPA RNAi constructs at 1 mg/kg - Study 10

| Treatment | Average Percent Change in Serum Lp(a) from Baseline | | |
|---|---|---|---|
| | Week 2 | Week 3 | Week 4 |
| 17188 | −89% | −75% | −66% |
| 17198 | −83% | −58% | −43% |
| 17200 | −77% | −23% | −18% |
| 18434 | −84% | −53% | −41% |
| 18446 | −94% | −79% | −69% |

TABLE 15

Serum Lp(a) levels in double transgenic mice following administration of LPA RNAi constructs at 1 mg/kg - Study 11

| Treatment | Average Percent Change in Serum Lp(a) from Baseline | | |
|---|---|---|---|
| | Week 2 | Week 3 | Week 4 |
| 11379 | −89% | −55% | −46% |
| 17199 | −80% | −30% | −20% |
| 20022 | −76% | −32% | −43% |
| 20027 | −89% | −55% | −45% |
| 20040 | −79% | −42% | −38% |

Most of the LPA RNAi constructs tested reduced serum Lp(a) levels by at least 50% two weeks after a single subcutaneous injection of a dose of 1 mg/kg or 2 mg/kg in the transgenic animals. Some RNAi constructs produced prolonged inhibition of Lp(a) serum levels out to four weeks with a single injection. For example, Lp(a) serum levels were still reduced by about 50% or more at 4 weeks following a single 1 mg/kg or 2 mg/kg injection of constructs 4601, 4613, 4930, 4970, 6150, 6182, 6247, 8395, 8401, 10927, 11318, 11344, 11351, 11374, 11580, 17188, 18436, 18444, and 18446.

Example 4. In Vivo Efficacy of LPA RNAi Constructs in Non-Human Primates

Efficacy of select LPA RNAi constructs was assessed in cynomolgus monkeys in three separate studies. The RNAi constructs had sequences that cross-reacted with the sequence of the cynomolgus LPA gene (NCBI Reference Sequence No. XM_015448520.1). In a first study, cynomolgus monkeys (n=3 per treatment group) received a single subcutaneous injection of 2 mg/kg of LPA RNAi constructs 4601, 4613, or 4970. Blood samples were collected on day −1 (prior to dosing) and on day 4, 7, 14, 21, 28, 35, 42, 49, 56, 63, 70, 77, 84, 91, 98, 105, 112, 119, 126, 133, and 140 following dosing on day 1. Lp(a) serum levels in each sample were analyzed using an Lp(a) ELISA assay (Cat. #10-1106-01, Mercodia AB, Uppsala, Sweden). The results of the first study are shown in FIG. 2. Data are expressed as percentage of Lp(a) serum levels remaining relative to pre-dose baseline. Constructs 4601 and 4613 suppressed serum Lp(a) levels over 80% relative to baseline levels for at least six weeks (e.g. out to at least day 42).

Figure 3:
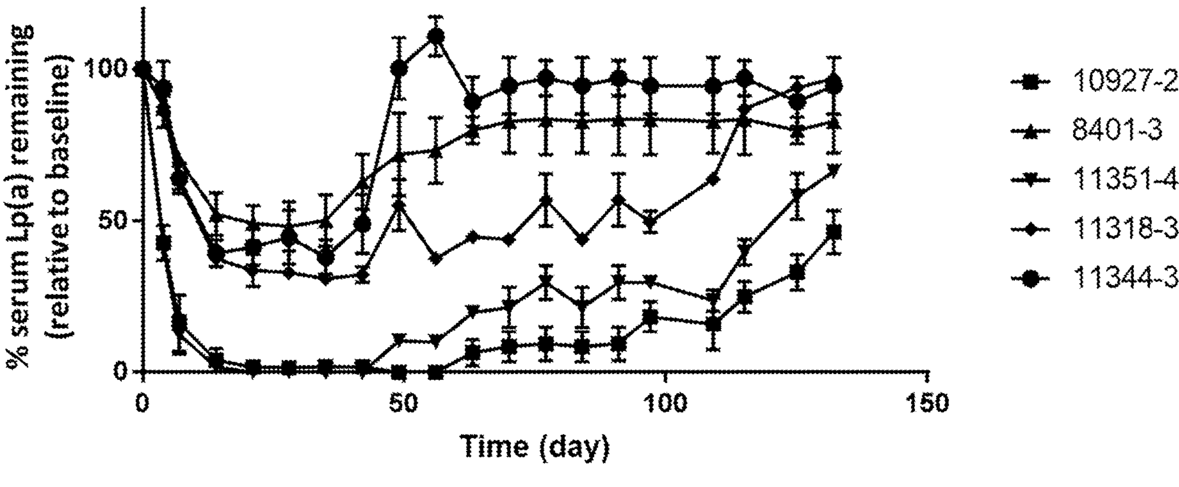
FIG. 3 shows the percentage of serum Lp(a) remaining relative to pre-dose baseline levels in cynomolgus monkeys following administration of a single subcutaneous injection of 2 mg/kg of the indicated LPA RNAi constructs on day 1.

In a second study, cynomolgus monkeys (n=3 per treatment group) received a single subcutaneous injection of 2 mg/kg of LPA RNAi constructs 8401, 10927, 11318, 11344, or 11351. Blood samples were taken at the same time points as in the first study and analyzed for Lp(a) levels in the serum as described above. The results of the second study are shown in FIG. 3. Data are expressed as percentage of Lp(a) serum levels remaining relative to pre-dose baseline. Remarkably, constructs 10927 and 11351 nearly completed suppressed Lp(a) serum levels through eight weeks. Significant reduction in serum Lp(a) levels was still observed through day 112, almost four months after the single dose injection. In contrast, constructs 8401 and 11344 produced more modest and transient reductions in serum Lp(a) levels. Construct 11318 suppressed Lp(a) in the serum to levels that were about 40% of baseline, and this level of reduction was sustained for several weeks.

Figure 4:
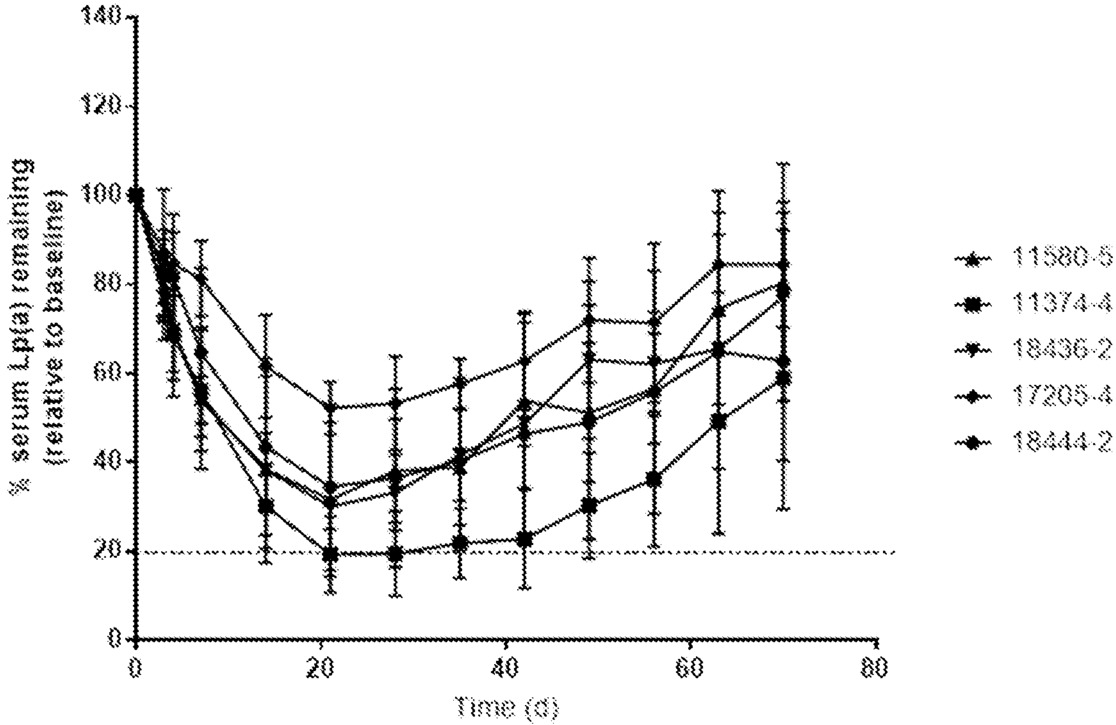
FIG. 4 shows the percentage of serum Lp(a) remaining relative to pre-dose baseline levels in cynomolgus monkeys following administration of a single subcutaneous injection of 2 mg/kg of the indicated LPA RNAi constructs on day 1.

In a third study, cynomolgus monkeys (n=3 per treatment group) received a single subcutaneous injection of 2 mg/kg of LPA RNAi constructs 11374, 11580, 17205, 18444, or 18436. Blood samples were taken at the same time points and analyzed for Lp(a) levels in the serum as in the previous two studies described above. The results of the third study are shown in FIG. 4. Data are expressed as percentage of Lp(a) serum levels remaining relative to pre-dose baseline. Construct 11374 was the most potent of this group of molecules, suppressing Lp(a) serum levels to 20% of baseline levels for about six weeks following a single subcutaneous injection.

Example 5. Viscosity Assessment of LPA RNAi Constructs

The viscosity of LPA RNAi construct 11374 in phosphate buffered saline (PBS) was assessed at different concentrations. Lyophilized 11374 was formulated with PBS to prepare a stock solution. Dilutions of the stock solution with PBS were made to prepare the different formulations of the 11374 construct at concentrations ranging from 150 to 350 mg/mL. For comparison purposes, the viscosity of LPA RNAi construct AD03851 (described in WO 2017/059223) was also assessed in parallel. The modified nucleotide sequences for AD03851 are set forth below:

```
Sense sequence:
                                        (SEQ ID NO: 620)
5'-csagccccuUfAfUfuguuauacgs(invdA)-3'
```

-continued

```
Antisense sequence:
                                        (SEQ ID NO: 621)
5'-usCfsgUfaUfaacaaUfaAfgGfgGfcsUfsg-3'
```

where a, u, g, and c=corresponding 2'-O-methyl ribonucleotide; Af, Uf, Gf, and Cf=corresponding 2'-deoxy-2'-fluoro ribonucleotide; invdA=an inverted deoxyadenosine nucleotide (i.e. 3'-3' linked); and s=a phosphorothioate internucleotide linkage. The 5' end of the sense strand was covalently attached to a trivalent GalNAc moiety (NAG25, the structure of which is described in WO 2017/059223) via a phosphorothioate bond.

To calculate the concentration of 11374 formulations, the absorbance of the samples at 260 nm was measured using an Agilent 8453 G1103A UV-Visible spectrophotometer. An approximated extinction coefficient of 19.1 mL*mg$^{-1}$*cm$^{-1}$, which is the measured extinction coefficient for AD03851 at 260 nm, and a 1 cm pathlength was then used to calculate the formulation concentrations using Beer's law.

Viscosity of each formulation was measured using an Anton Paar MCR 302 cone and plate rheometer at a shear rate of 1000 s$^{-1}$ at 25° C. The viscosity measurements for the two LPA RNAi constructs at different concentrations in PBS are shown below in Table 16.

TABLE 16

Viscosity of LPA RNAi Constructs in PBS

| Construct 11374 | | Construct AD03851 | |
|---|---|---|---|
| Concentration (mg/mL) | Viscosity (cP) | Concentration (mg/mL) | Viscosity (cP) |
| 144.8 | 2.4 | 153.9 | 3.9 |
| 192.1 | 3.9 | 202.5 | 8.3 |
| 240.1 | 6.4 | 251.5 | 24.0 |
| 287.0 | 11.4 | 300.6 | 200.7 |
| 344.8 | 22.3 | 341.5 | 613.8 |
| 490.9 | 1047.2 | — | — |

The LPA RNAi construct 11374 has a lower viscosity as a function of concentration in comparison to AD03851, a benchmark RNAi construct, which could enable higher concentration formulations and reduced injection volumes.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. An RNAi construct comprising a sense strand and an antisense strand, wherein the antisense strand comprises a region having a sequence that is complementary to a lipoprotein (a) (LPA) mRNA sequence, wherein the sense strand comprises or consists of the sequence of SEQ ID NO: 79 or SEQ ID NO: 80 and the antisense strand comprises or consists of the sequence of SEQ ID NO: 194, and wherein all of the nucleotides in the sense and antisense strands are a combination of 2'-O-methyl modified nucleotides and 2'-fluoro modified nucleotides.

2. The RNAi construct of claim 1, wherein the sense strand further comprises an abasic nucleotide as the terminal nucleotide at its 3' end, its 5' end, or both its 3' and 5' ends.

3. The RNAi construct of claim 2, wherein the abasic nucleotide is linked to the adjacent nucleotide through a 3'-3' internucleotide linkage or a 5'-5' internucleotide linkage.

4. The RNAi construct of claim 1, wherein the sense strand, the antisense strand, or both the sense and antisense strands comprise one or more phosphorothioate internucleotide linkages.

5. The RNAi construct of claim 4, wherein the antisense strand comprises two consecutive phosphorothioate internucleotide linkages between the terminal nucleotides at both the 3' and 5' ends.

6. The RNAi construct of claim 4, wherein the sense strand comprises a single phosphorothioate internucleotide linkage between the terminal nucleotides at the 3' end.

7. The RNAi construct of claim 4, wherein the sense strand comprises two consecutive phosphorothioate internucleotide linkages between the terminal nucleotides at the 3' end.

8. The RNAi construct of claim 1, wherein the RNAi construct further comprises a ligand.

9. The RNAi construct of claim 8, wherein the ligand comprises a cholesterol moiety, a vitamin, a steroid, a bile acid, a folate moiety, a fatty acid, a carbohydrate, a glycoside, or antibody or antigen-binding fragment thereof.

10. The RNAi construct of claim 8, wherein the ligand comprises galactose, galactosamine, or N-acetyl-galactosamine.

11. The RNAi construct of claim 10, wherein the ligand comprises a multivalent galactose moiety or multivalent N-acetyl-galactosamine moiety.

12. The RNAi construct of claim 11, wherein the multivalent galactose moiety or multivalent N-acetyl-galactosamine moiety is trivalent or tetravalent.

13. The RNAi construct of claim 8, wherein the ligand is covalently attached to the sense strand optionally through a linker.

14. The RNAi construct of claim 13, wherein the ligand is covalently attached to the 5' end of the sense strand.

15. The RNAi construct of claim 8, wherein the ligand comprises the structure of:

[Structure 1]

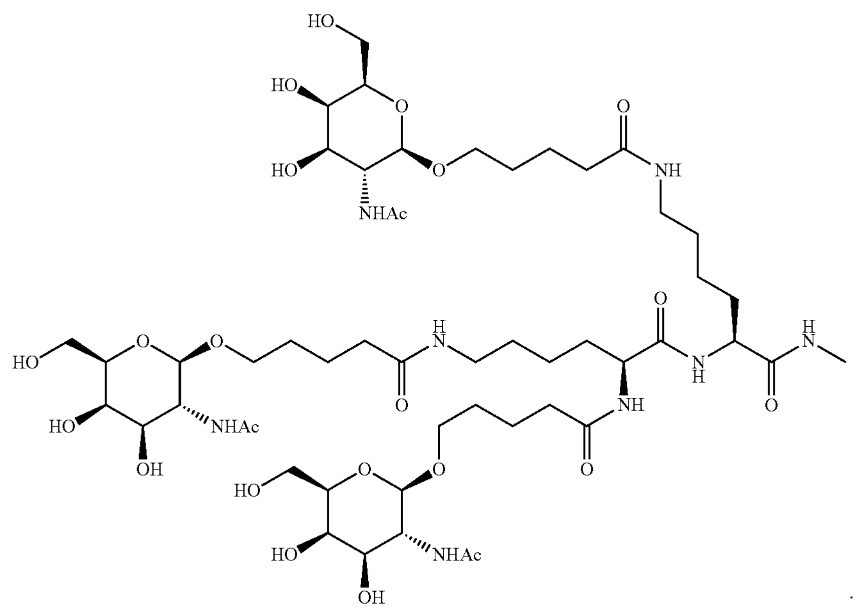

16. The RNAi construct of claim 1, wherein the RNAi construct further comprises a ligand covalently attached to the 5' end of the sense strand through a linker, and wherein the ligand and linker have the structure of Formula VII:

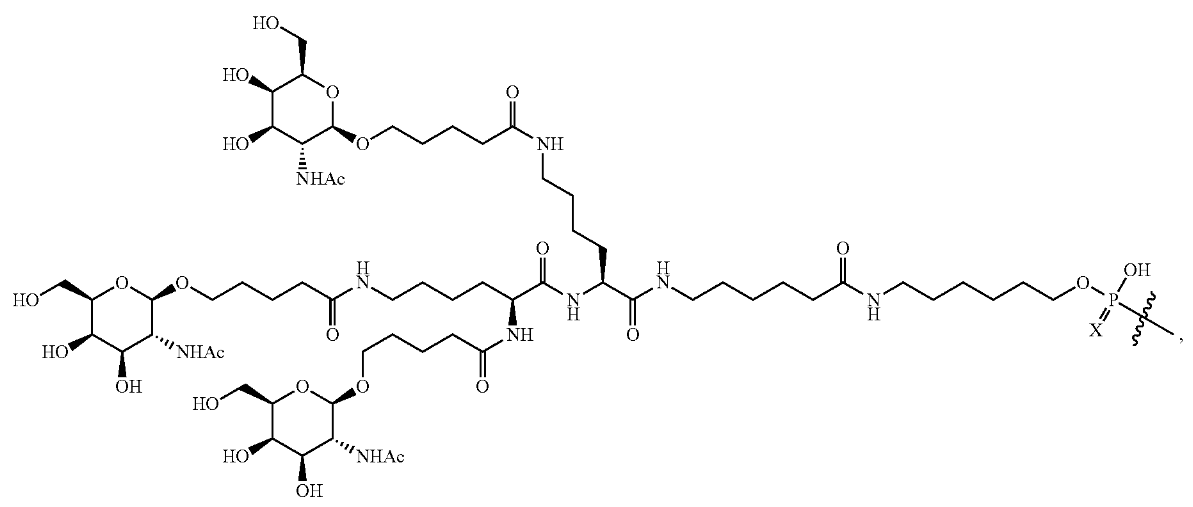

wherein X=O or S.

17. A pharmaceutical composition comprising the RNAi construct of claim 1 and a pharmaceutically acceptable carrier or excipient.

18. A method for reducing the expression of the LPA gene in a patient in need thereof comprising administering to the patient the RNAi construct of claim 1.

19. A method for reducing serum or plasma Lp(a) particle levels in a patient in need thereof comprising administering to the patient the RNAi construct of claim 1.

20. A method for treating cardiovascular disease in a patient in need thereof comprising administering to the patient the RNAi construct of claim 1.

21. A method for reducing the risk of myocardial infarction in a patient in need thereof comprising administering to the patient the RNAi construct of claim 1.

22. An RNAi construct comprising a sense strand and an antisense strand, wherein the antisense strand comprises a region having a sequence that is complementary to an LPA mRNA sequence, wherein the sense strand comprises or consists of the sequence of modified nucleotides according to SEQ ID NO: 350 and the antisense strand comprises or consists of the sequence of modified nucleotides according to SEQ ID NO: 525.

23. The RNAi construct of claim 22, wherein the sense strand consists of the sequence of modified nucleotides according to SEQ ID NO: 350 and the antisense strand consists of the sequence of modified nucleotides according to SEQ ID NO: 525.

24. A pharmaceutical composition comprising the RNAi construct of claim 23 and a pharmaceutically acceptable carrier or excipient.

25. A method for reducing serum or plasma Lp(a) particle levels in a patient in need thereof comprising administering to the patient the RNAi construct of claim 23.

26. A method for treating cardiovascular disease in a patient in need thereof comprising administering to the patient the RNAi construct of claim 23.

27. An RNAi construct comprising a sense strand and an antisense strand, wherein the antisense strand comprises a region having a sequence that is complementary to an LPA mRNA sequence, wherein the sense strand comprises or consists of the sequence of modified nucleotides according to SEQ ID NO: 350 and the antisense strand comprises or consists of the sequence of modified nucleotides according to SEQ ID NO: 527.

28. The RNAi construct of claim 27, wherein the sense strand consists of the sequence of modified nucleotides according to SEQ ID NO: 350 and the antisense strand consists of the sequence of modified nucleotides according to SEQ ID NO: 527.

29. A pharmaceutical composition comprising the RNAi construct of claim 28 and a pharmaceutically acceptable carrier or excipient.

30. A method for reducing serum or plasma Lp(a) particle levels in a patient in need thereof comprising administering to the patient the RNAi construct of claim 28.

31. A method for treating cardiovascular disease in a patient in need thereof comprising administering to the patient the RNAi construct of claim 28.

32. An RNAi construct comprising a sense strand and an antisense strand, wherein the antisense strand comprises a region having a sequence that is complementary to an LPA mRNA sequence, wherein the sense strand comprises or consists of the sequence of modified nucleotides according to SEQ ID NO: 354 and the antisense strand comprises or consists of the sequence of modified nucleotides according to SEQ ID NO: 525.

33. The RNAi construct of claim 32, wherein the sense strand consists of the sequence of modified nucleotides according to SEQ ID NO: 354 and the antisense strand consists of the sequence of modified nucleotides according to SEQ ID NO: 525.

34. A pharmaceutical composition comprising the RNAi construct of claim 33 and a pharmaceutically acceptable carrier or excipient.

35. A method for reducing serum or plasma Lp(a) particle levels in a patient in need thereof comprising administering to the patient the RNAi construct of claim 33.

36. A method for treating cardiovascular disease in a patient in need thereof comprising administering to the patient the RNAi construct of claim 33.

* * * * *

SEQUENCE LISTING

```
<160> NUMBER OF SEQ ID NOS: 621

<210> SEQ ID NO 1
<211> LENGTH: 6431
<212> TYPE: DNA
<213> ORGANISM: Homo sapiens
```

<400> SEQUENCE: 1

```
gtaagtcaac aatgtcctgg gattgggaca cactttctgg gcactgctgg ccagtcccaa     60
aatggaacat aaggaagtgg ttcttctact tcttttattt ctgaaatcag cagcacctga    120
gcaaagccat gtggtccagg attgctacca tggtgatgga cagagttatc gaggcacgta    180
ctccaccact gtcacaggaa ggacctgcca agcttggtca tctatgacac cacatcaaca    240
taataggacc acagaaaact acccaaatgc tggcttgatc atgaactact gcaggaatcc    300
agatgctgtg gcagctcctt attgttatac gagggatccc ggtgtcaggt gggagtactg    360
caacctgacg caatgctcag acgcagaagg gactgccgtc gcgcctccga ctgttacccc    420
ggttccaagc ctagaggctc cttccgaaca agcaccgact gagcaaaggc ctggggtgca    480
ggagtgctac catggtaatg gacagagtta tcgaggcaca tactccacca ctgtcacagg    540
aagaacctgc caagcttggt catctatgac accacactcg catagtcgga ccccagaata    600
ctacccaaat gctggcttga tcatgaacta ctgcaggaat ccagatgctg tggcagctcc    660
ttattgttat acgagggatc ccggtgtcag gtgggagtac tgcaacctga cgcaatgctc    720
agacgcagaa gggactgccg tcgcgcctcc gactgttacc ccggttccaa gcctagaggc    780
tccttccgaa caagcaccga ctgagcaaag gcctggggtg caggagtgct accatggtaa    840
tggacagagt tatcgaggca catactccac cactgtcaca ggaagaacct gccaagcttg    900
gtcatctatg acaccacact cgcatagtcg gaccccagaa tactacccaa atgctggctt    960
gatcatgaac tactgcagga atccagatgc tgtggcagct ccttattgtt atacgaggga   1020
tcccggtgtc aggtgggagt actgcaacct gacgcaatgc tcagacgcag aagggactgc   1080
cgtcgcgcct ccgactgtta ccccggttcc aagcctagag gctccttccg aacaagcacc   1140
gactgagcag aggcctgggg tgcaggagtg ctaccacggt aatggacaga gttatcgagg   1200
cacatactcc accactgtca ctggaagaac ctgccaagct tggtcatcta tgacaccaca   1260
ctcgcatagt cggaccccag aatactaccc aaatgctggc ttgatcatga actactgcag   1320
gaatccagat gctgtggcag ctccttattg ttatacgagg gatcccggtg tcaggtggga   1380
gtactgcaac ctgacgcaat gctcagacgc agaagggact gccgtcgcgc ctccgactgt   1440
taccccggtt ccaagcctag aggctccttc cgaacaagca ccgactgagc aaaggcctgg   1500
ggtgcaggag tgctaccatg gtaatggaca gagttatcga ggcacatact ccaccactgt   1560
cacaggaaga acctgccaag cttggtcatc tatgacacca cactcgcata gtcggacccc   1620
agaatactac ccaaatgctg gcttgatcat gaactactgc aggaatccag atgctgtggc   1680
agctccttat tgttatacga gggatcccgg tgtcaggtgg gagtactgca acctgacgca   1740
atgctcagac gcagaaggga ctgccgtcgc gcctccgact gttaccccgg ttccaagcct   1800
agaggctcct tccgaacaag caccgactga gcaaaggcct ggggtgcagg agtgctacca   1860
tggtaatgga cagagttatc gaggcacata ctccaccact gtcacaggaa gaacctgcca   1920
agcttggtca tctatgacac cacactcgca tagtcggacc ccagaatact acccaaatgc   1980
tggcttgatc atgaactact gcaggaatcc agatgctgtg gcagctcctt attgttatac   2040
gagggatccc ggtgtcaggt gggagtactg caacctgacg caatgctcag acgcagaagg   2100
gactgccgtc gcgcctccga ctgttacccc ggttccaagc ctagaggctc cttccgaaca   2160
agcaccgact gagcaaaggc ctggggtgca ggagtgctac catggtaatg gacagagtta   2220
tcgaggcaca tactccacca ctgtcacagg aagaacctgc caagcttggt catctatgac   2280
```

-continued

```
accacactcg catagtcgga ccccagaata ctacccaaat gctggcttga tcatgaacta   2340
ctgcaggaat ccagatgctg tggcagctcc ttattgttat acgagggatc ccggtgtcag   2400
gtgggagtac tgcaacctga cgcaatgctc agacgcagaa gggactgccg tcgcgcctcc   2460
gactgttacc ccggttccaa gcctagaggc tccttccgaa caagcaccga ctgagcagag   2520
gcctggggtg caggagtgct accacggtaa tggacagagt tatcgaggca catactccac   2580
cactgtcact ggaagaacct gccaagcttg gtcatctatg acaccacact cgcatagtcg   2640
gaccccagaa tactacccaa atgctggctt gatcatgaac tactgcagga atccagatcc   2700
tgtggcagcc ccttattgtt atacgaggga tcccagtgtc aggtgggagt actgcaacct   2760
gacacaatgc tcagacgcag aagggactgc cgtcgcgcct ccaactatta ccccgattcc   2820
aagcctagag gctccttctg aacaagcacc aactgagcaa aggcctgggg tgcaggagtg   2880
ctaccacgga aatggacaga gttatcaagg cacatacttc attactgtca caggaagaac   2940
ctgccaagct tggtcatcta tgacaccaca ctcgcatagt cggaccccag catactaccc   3000
aaatgctggc ttgatcaaga actactgccg aaatccagat cctgtggcag ccccttggtg   3060
ttatacaaca gatcccagtg tcaggtggga gtactgcaac ctgacacgat gctcagatgc   3120
agaatggact gccttcgtcc ctccgaatgt tattctggct ccaagcctag aggctttttt   3180
tgaacaagca ctgactgagg aaacccccgg ggtacaggac tgctactacc attatggaca   3240
gagttaccga ggcacatact ccaccactgt cacaggaaga acttgccaag cttggtcatc   3300
tatgacacca caccagcata gtcggacccc agaaaactac ccaaatgctg gcctgaccag   3360
gaactactgc aggaatccag atgctgagat tcgcccttgg tgttacacca tggatcccag   3420
tgtcaggtgg gagtactgca acctgacaca atgcctggtg acagaatcaa gtgtccttgc   3480
aactctcacg gtggtcccag atccaagcac agaggcttct tctgaagaag caccaacgga   3540
gcaaagcccc ggggtccagg attgctacca tggtgatgga cagagttatc gaggctcatt   3600
ctctaccact gtcacaggaa ggacatgtca gtcttggtcc tctatgacac cacactggca   3660
tcagaggaca acagaatatt atccaaatgg tggcctgacc aggaactact gcaggaatcc   3720
agatgctgag attagtcctt ggtgttatac catggatccc aatgtcagat gggagtactg   3780
caacctgaca caatgtccag tgacagaatc aagtgtcctt gcgacgtcca cggctgtttc   3840
tgaacaagca ccaacggagc aaagccccac agtccaggac tgctaccatg gtgatggaca   3900
gagttatcga ggctcattct ccaccactgt tacaggaagg acatgtcagt cttggtcctc   3960
tatgacacca cactggcatc agagaaccac agaatactac ccaaatggtg gcctgaccag   4020
gaactactgc aggaatccag atgctgagat tcgcccttgg tgttatacca tggatcccag   4080
tgtcagatgg gagtactgca acctgacgca atgtccagtg atggaatcaa ctctcctcac   4140
aactcccacg gtggtcccag ttccaagcac agagcttcct tctgaagaag caccaactga   4200
aaacagcact ggggtccagg actgctaccg aggtgatgga cagagttatc gaggcacact   4260
ctccaccact atcacaggaa gaacatgtca gtcttggtcg tctatgacac cacattggca   4320
tcggaggatc ccattatact atccaaatgc tggcctgacc aggaactact gcaggaatcc   4380
agatgctgag attcgccctt ggtgttacac catggatccc agtgtcaggt gggagtactg   4440
caacctgaca cgatgtccag tgacagaatc gagtgtcctc acaactccca cagtggcccc   4500
ggttccaagc acagaggctc cttctgaaca agcaccacct gagaaaagcc ctgtggtcca   4560
ggattgctac catggtgatg gacggagtta tcgaggcata tcctccacca ctgtcacagg   4620
aaggacctgt caatcttggt catctatgat accacactgg catcagagga ccccagaaaa   4680
```

-continued

```
ctacccaaat gctggcctga ccgagaacta ctgcaggaat ccagattctg ggaaacaacc   4740

ctggtgttac acaaccgatc cgtgtgtgag gtgggagtac tgcaatctga cacaatgctc   4800

agaaacagaa tcaggtgtcc tagagactcc cactgttgtt ccagttccaa gcatggaggc   4860

tcattctgaa gcagcaccaa ctgagcaaac ccctgtggtc cggcagtgct accatggtaa   4920

tggccagagt tatcgaggca cattctccac cactgtcaca ggaaggacat gtcaatcttg   4980

gtcatccatg acaccacacc ggcatcagag gaccccagaa aactacccaa atgatggcct   5040

gacaatgaac tactgcagga atccagatgc cgatacaggc ccttggtgtt ttaccatgga   5100

ccccagcatc aggtgggagt actgcaacct gacgcgatgc tcagacacag aagggactgt   5160

ggtcgctcct ccgactgtca tccaggttcc aagcctaggg cctccttctg aacaagactg   5220

tatgtttggg aatgggaaag gataccgggg caagaaggca accactgtta ctgggacgcc   5280

atgccaggaa tgggctgccc aggagcccca tagacacagc acgttcattc cagggacaaa   5340

taaatgggca ggtctggaaa aaaattactg ccgtaaccct gatggtgaca tcaatggtcc   5400

ctggtgctac acaatgaatc caagaaaact tttgactac tgtgatatcc ctctctgtgc    5460

atcctcttca tttgattgtg ggaagcctca agtggagccg aagaaatgtc ctggaagcat   5520

tgtagggggg tgtgtggccc acccacattc ctggccctgg caagtcagtc tcagaacaag   5580

gtttggaaag cacttctgtg gaggcacctt aatatcccca gagtgggtgc tgactgctgc   5640

tcactgcttg aagaagtcct caaggccttc atcctacaag gtcatcctgg gtgcacacca   5700

agaagtgaac ctcgaatctc atgttcagga aatagaagtg tctaggctgt tcttggagcc   5760

cacacaagca gatattgcct tgctaaagct aagcaggcct gccgtcatca ctgacaaagt   5820

aatgccagct tgtctgccat ccccagacta catggtcacc gccaggactg aatgttacat   5880

cactggctgg ggagaaaccc aaggtacctt tgggactggc cttctcaagg aagcccagct   5940

ccttgttatt gagaatgaag tgtgcaatca ctataagtat atttgtgctg agcatttggc   6000

cagaggcact gacagttgcc agggtgacag tggagggcct ctggtttgct tcgagaagga   6060

caaatacatt ttacaaggag tcacttcttg ggtcttggc tgtgcacgcc ccaataagcc    6120

tggtgtctat gctcgtgttt caaggtttgt tacttggatt gagggaatga tgagaaataa   6180

ttaattggac gggagacaga gtgaagcatc aacctactta gaagctgaaa cgtgggtaag   6240

gatttagcat gctggaaata atagacagca atcaaacgaa gacactgttc ccagctacca   6300

gctatgccaa accttggcat tttggtattt tttgtgtata agcttttaag gtctgactga   6360

caaattctgt attaaggtgt catagctatg acatttgtta aaaataaact ctgcacttat   6420

tttgatttga a                                                        6431
```

<210> SEQ ID NO 2
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 2

```
ccugagcaaa gccaugugau u                                               21
```

<210> SEQ ID NO 3
<211> LENGTH: 21
<212> TYPE: RNA
<213> ORGANISM: Artificial Sequence
<220> FEATURE:

<223> OTHER INFORMATION: synthetic unmodified polynucleotide

<400> SEQUENCE: 3
cugagcaaag ccauguggu u 21

<210> SEQ ID NO 4
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 4
gugguccagg auugcuacuu u 21

<210> SEQ ID NO 5
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 5
ccacagaaaa cuacccaaau u 21

<210> SEQ ID NO 6
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 6
cagaagggac ugccgucguu u 21

<210> SEQ ID NO 7
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 7
agaagggacu gccgucgcgu u 21

<210> SEQ ID NO 8
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 8
agaagggacu gccgucgcau u 21

<210> SEQ ID NO 9
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 9
gcuccuuccg aacaagcauu u 21

-continued

<210> SEQ ID NO 10
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 10
cuccuuccga acaagcacuu u 21

<210> SEQ ID NO 11
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 11
cuuccgaaca agcaccgacu u 21

<210> SEQ ID NO 12
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 12
cuuccgaaca agcaccgauu u 21

<210> SEQ ID NO 13
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 13
uuccgaacaa gcaccgacuu u 21

<210> SEQ ID NO 14
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 14
ccuuccgaac aagcaccgac u 21

<210> SEQ ID NO 15
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 15
ccuuccgaac aagcaccgac 20

<210> SEQ ID NO 16
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 16
uccgaacaag caccgacuau u 21

<210> SEQ ID NO 17
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 17
cgaacaagca ccgacugagu u 21

<210> SEQ ID NO 18
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 18
agcaccgacu gagcaaagau u 21

<210> SEQ ID NO 19
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 19
gcaccgacug agcaaagguu u 21

<210> SEQ ID NO 20
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 20
caccgacuga gcaaaggccu u 21

<210> SEQ ID NO 21
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 21
aaggccuggg gugcaggaau u 21

<210> SEQ ID NO 22
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 22
cuggggugca ggagugcuau u 21

<210> SEQ ID NO 23
<211> LENGTH: 20

<212> TYPE: RNA
<213> ORGANISM: Artificial Sequence
<220> FEATURE:
<223> OTHER INFORMATION: synthetic unmodified polynucleotide

<400> SEQUENCE: 23
cuggggugca ggagugcuau 20

<210> SEQ ID NO 24
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 24
ggggugcagg agugcuaccu u 21

<210> SEQ ID NO 25
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 25
gaauccagau ccuguggcau u 21

<210> SEQ ID NO 26
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 26
ccuguggcag ccccuuauuu u 21

<210> SEQ ID NO 27
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 27
ggcagccccu uauuguuauu u 21

<210> SEQ ID NO 28
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 28
guggcagccc cuuauuguua u 21

<210> SEQ ID NO 29
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 29
guggcagccc cuuauuguua 20

<210> SEQ ID NO 30
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 30
gcagccccuu auuguuauau u 21

<210> SEQ ID NO 31
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 31
agccccuuau uguuauacgu u 21

<210> SEQ ID NO 32
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 32
agccccuuau uguuauacau u 21

<210> SEQ ID NO 33
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 33
gccccuuauu guuauacgau u 21

<210> SEQ ID NO 34
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 34
cagccccuua uuguuauacg 20

<210> SEQ ID NO 35
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 35
ccccuuauug uuauacgagu u 21

<210> SEQ ID NO 36
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 36
agccccuuau uguuauacga g 21

<210> SEQ ID NO 37
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 37
agccccuuau uguuauacga 20

<210> SEQ ID NO 38
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 38
ccccuuauug uuauacgaau u 21

<210> SEQ ID NO 39
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 39
cugacacaau gcucagacgu u 21

<210> SEQ ID NO 40
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 40
cugacacaau gcucagacau u 21

<210> SEQ ID NO 41
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 41
accugacaca augcucagac a 21

<210> SEQ ID NO 42
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 42
accugacaca augcucagac 20

<210> SEQ ID NO 43
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 43
accugacaca augcucagac g 21

<210> SEQ ID NO 44
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 44
gacacaaugc ucagacgcau u 21

<210> SEQ ID NO 45
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 45
acacaaugcu cagacgcagu u 21

<210> SEQ ID NO 46
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 46
ugacacaaug cucagacgca g 21

<210> SEQ ID NO 47
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 47
ugacacaaug cucagacgca a 21

<210> SEQ ID NO 48
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 48
ugacacaaug cucagacgca 20

<210> SEQ ID NO 49
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 49
acacaaugcu cagacgcaau 20

<210> SEQ ID NO 50
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 50
acacaaugcu cagacgcaau u 21

<210> SEQ ID NO 51
<211> LENGTH: 18
<212> TYPE: RNA
<213> ORGANISM: Artificial Sequence
<220> FEATURE:
<223> OTHER INFORMATION: synthetic unmodified polynucleotide

<400> SEQUENCE: 51
acacaaugcu cagacgca 18

<210> SEQ ID NO 52
<211> LENGTH: 19
<212> TYPE: RNA
<213> ORGANISM: Artificial Sequence
<220> FEATURE:
<223> OTHER INFORMATION: synthetic unmodified polynucleotide

<400> SEQUENCE: 52
acacaaugcu cagacgcaa 19

<210> SEQ ID NO 53
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 53
ccuagaggcu ccuucugaau u 21

<210> SEQ ID NO 54
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 54
agccuagagg cuccuucuga a 21

<210> SEQ ID NO 55
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 55
agccuagagg cuccuucuga 20

<210> SEQ ID NO 56

<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 56
agaggcuccu ucugaacaau u 21

<210> SEQ ID NO 57
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 57
agcaccaacu gagcaaagau u 21

<210> SEQ ID NO 58
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 58
aaauccagau ccuguggcau u 21

<210> SEQ ID NO 59
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 59
ggcagccccu ugguguuauu u 21

<210> SEQ ID NO 60
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 60
agaacuugcc aagcuugguu u 21

<210> SEQ ID NO 61
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 61
gaagaacuug ccaagcuugg u 21

<210> SEQ ID NO 62
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 62
gaagaacuug ccaagcuugg 20

<210> SEQ ID NO 63
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 63
gaacuugcca agcuugguuu u 21

<210> SEQ ID NO 64
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 64
aagaacuugc caagcuuggu u 21

<210> SEQ ID NO 65
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 65
aagaacuugc caagcuuggu 20

<210> SEQ ID NO 66
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 66
acaccagcau agucggacuu u 21

<210> SEQ ID NO 67
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 67
caccagcaua gucggaccuu u 21

<210> SEQ ID NO 68
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 68
cgcccuuggu guuacaccau u 21

<210> SEQ ID NO 69
<211> LENGTH: 21
<212> TYPE: RNA

<213> ORGANISM: Artificial Sequence
<220> FEATURE:
<223> OTHER INFORMATION: synthetic unmodified polynucleotide

<400> SEQUENCE: 69
uucgcccuug guguuacacc a 21

<210> SEQ ID NO 70
<211> LENGTH: 18
<212> TYPE: RNA
<213> ORGANISM: Artificial Sequence
<220> FEATURE:
<223> OTHER INFORMATION: synthetic unmodified polynucleotide

<400> SEQUENCE: 70
cgcccuuggu guuacacc 18

<210> SEQ ID NO 71
<211> LENGTH: 19
<212> TYPE: RNA
<213> ORGANISM: Artificial Sequence
<220> FEATURE:
<223> OTHER INFORMATION: synthetic unmodified polynucleotide

<400> SEQUENCE: 71
cgcccuuggu guuacacca 19

<210> SEQ ID NO 72
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 72
uucgcccuug guguuacacc 20

<210> SEQ ID NO 73
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 73
gcccuuggug uuacaccauu u 21

<210> SEQ ID NO 74
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 74
ucgcccuugg uguuacacca 20

<210> SEQ ID NO 75
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 75
gcccuuggug uuacaccauu 20

<210> SEQ ID NO 76
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 76
gguguuacac cauggaucuu u 21

<210> SEQ ID NO 77
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 77
gaaucaagug uccuugcaau u 21

<210> SEQ ID NO 78
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 78
cagaaucaag uguccuugca 20

<210> SEQ ID NO 79
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 79
gaaucaagug uccuugcaau 20

<210> SEQ ID NO 80
<211> LENGTH: 18
<212> TYPE: RNA
<213> ORGANISM: Artificial Sequence
<220> FEATURE:
<223> OTHER INFORMATION: synthetic unmodified polynucleotide

<400> SEQUENCE: 80
gaaucaagug uccuugca 18

<210> SEQ ID NO 81
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 81
aaucaagugu ccuugcaacu u 21

<210> SEQ ID NO 82
<211> LENGTH: 21
<212> TYPE: RNA
<213> ORGANISM: Artificial Sequence
<220> FEATURE:

<223> OTHER INFORMATION: synthetic unmodified polynucleotide

<400> SEQUENCE: 82
aaucaagugu ccuugcaauu u 21

<210> SEQ ID NO 83
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 83
agaaucaagu guccuugcaa 20

<210> SEQ ID NO 84
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 84
agaaucaagu guccuugcaa u 21

<210> SEQ ID NO 85
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 85
aaucaagugu ccuugcaauu 20

<210> SEQ ID NO 86
<211> LENGTH: 18
<212> TYPE: RNA
<213> ORGANISM: Artificial Sequence
<220> FEATURE:
<223> OTHER INFORMATION: synthetic unmodified polynucleotide

<400> SEQUENCE: 86
aaucaagugu ccuugcaa 18

<210> SEQ ID NO 87
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 87
ucaagugucc uugcaacuuu u 21

<210> SEQ ID NO 88
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 88
cuucugaaga agcaccaauu u 21

<210> SEQ ID NO 89
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 89
uucugaagaa gcaccaacau u 21

<210> SEQ ID NO 90
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 90
ucuugguccu cuaugacauu u 21

<210> SEQ ID NO 91
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 91
agucuugguc cucuaugaca 20

<210> SEQ ID NO 92
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 92
ucuugguccu cuaugacauu 20

<210> SEQ ID NO 93
<211> LENGTH: 19
<212> TYPE: RNA
<213> ORGANISM: Artificial Sequence
<220> FEATURE:
<223> OTHER INFORMATION: synthetic unmodified polynucleotide

<400> SEQUENCE: 93
ucuugguccu cuaugacau 19

<210> SEQ ID NO 94
<211> LENGTH: 18
<212> TYPE: RNA
<213> ORGANISM: Artificial Sequence
<220> FEATURE:
<223> OTHER INFORMATION: synthetic unmodified polynucleotide

<400> SEQUENCE: 94
ucuugguccu cuaugaca 18

<210> SEQ ID NO 95
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 95
ugacaccaca cuggcaucau u 21

<210> SEQ ID NO 96
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 96
gacaacagaa uauuauccau 20

<210> SEQ ID NO 97
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 97
gcaaccugac acaaugucuu u 21

<210> SEQ ID NO 98
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 98
acacaauguc cagugacagu u 21

<210> SEQ ID NO 99
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 99
acacaauguc cagugacaau u 21

<210> SEQ ID NO 100
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 100
auguccagug acagaaucau u 21

<210> SEQ ID NO 101
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 101
guccagugac agaaucaagu u 21

<210> SEQ ID NO 102
<211> LENGTH: 21

<212> TYPE: RNA
<213> ORGANISM: Artificial Sequence
<220> FEATURE:
<223> OTHER INFORMATION: synthetic unmodified polynucleotide

<400> SEQUENCE: 102
guccagugac agaaucaaau u 21

<210> SEQ ID NO 103
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 103
uccagugaca gaaucaaguu u 21

<210> SEQ ID NO 104
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 104
ccagugacag aaucaaguau u 21

<210> SEQ ID NO 105
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 105
guccagugac agaaucaagu a 21

<210> SEQ ID NO 106
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 106
guccagugac agaaucaagu 20

<210> SEQ ID NO 107
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 107
ccagugacag aaucaaguau 20

<210> SEQ ID NO 108
<211> LENGTH: 18
<212> TYPE: RNA
<213> ORGANISM: Artificial Sequence
<220> FEATURE:
<223> OTHER INFORMATION: synthetic unmodified polynucleotide

<400> SEQUENCE: 108
ccagugacag aaucaagu 18

<210> SEQ ID NO 109
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 109
caccacuguu acaggaaggu u 21

<210> SEQ ID NO 110
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 110
caccacuguu acaggaagau u 21

<210> SEQ ID NO 111
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 111
cagaauacua cccaaauggu 20

<210> SEQ ID NO 112
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 112
cccaaauggu ggccugaccu u 21

<210> SEQ ID NO 113
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 113
uauaccaugg aucccagugu u 21

<210> SEQ ID NO 114
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 114
uauaccaugg aucccaguau u 21

<210> SEQ ID NO 115
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 115
uucugaagaa gcaccaacuu u 21

<210> SEQ ID NO 116
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 116
ccuucugaag aagcaccaac u 21

<210> SEQ ID NO 117
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 117
ccuucugaag aagcaccaac 20

<210> SEQ ID NO 118
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 118
cugaagaagc accaacugau u 21

<210> SEQ ID NO 119
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 119
agcaccaacu gaaaacaguu u 21

<210> SEQ ID NO 120
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 120
gaagcaccaa cugaaaacag 20

<210> SEQ ID NO 121
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 121
cccgguucca agcacagaau u 21

<210> SEQ ID NO 122
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 122
agcacagagg cuccuucuau u 21

<210> SEQ ID NO 123
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 123
ccuucugaac aagcaccacu u 21

<210> SEQ ID NO 124
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 124
ccuucugaac aagcaccauu u 21

<210> SEQ ID NO 125
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 125
ucagaaacag aaucagguau u 21

<210> SEQ ID NO 126
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 126
cagaaucagg uguccuagau u 21

<210> SEQ ID NO 127
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 127
guuaucgagg cacauucuuu u 21

<210> SEQ ID NO 128
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 128
uuaucgaggc acauucuccu u 21

<210> SEQ ID NO 129
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 129
uuaucgaggc acauucucuu u 21

<210> SEQ ID NO 130
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 130
acgcgaugcu cagacacaau u 21

<210> SEQ ID NO 131
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 131
agacacagaa gggacuguau u 21

<210> SEQ ID NO 132
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 132
uguccuggaa gcauuguaau u 21

<210> SEQ ID NO 133
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 133
aacaagguuu ggaaagcauu u 21

<210> SEQ ID NO 134
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 134
ucacauggcu uugcucaggu u 21

<210> SEQ ID NO 135

<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 135
accacauggc uuugcucagu u 21

<210> SEQ ID NO 136
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 136
aguagcaauc cuggaccacu u 21

<210> SEQ ID NO 137
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 137
uuuggguagu uuucuguggu u 21

<210> SEQ ID NO 138
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 138
acgacggcag ucccuucugu u 21

<210> SEQ ID NO 139
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 139
cgcgacggca gucccuucuu u 21

<210> SEQ ID NO 140
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 140
ugcgacggca gucccuucuu u 21

<210> SEQ ID NO 141
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 141
augcuuguuc ggaaggagcu u 21

<210> SEQ ID NO 142
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 142
agugcuuguu cggaaggagu u 21

<210> SEQ ID NO 143
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 143
gucggugcuu guucggaagu u 21

<210> SEQ ID NO 144
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 144
aucggugcuu guucggaagu u 21

<210> SEQ ID NO 145
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 145
agucggugcu uguucggaau u 21

<210> SEQ ID NO 146
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 146
agucggugcu uguucggaag guu 23

<210> SEQ ID NO 147
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 147
uagucggugc uuguucggau u 21

<210> SEQ ID NO 148
<211> LENGTH: 21
<212> TYPE: RNA

<213> ORGANISM: Artificial Sequence
<220> FEATURE:
<223> OTHER INFORMATION: synthetic unmodified polynucleotide

<400> SEQUENCE: 148
cucagucggu gcuuguucgu u 21

<210> SEQ ID NO 149
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 149
ucuuugcuca gucggugcuu u 21

<210> SEQ ID NO 150
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 150
accuuugcuc agucggugcu u 21

<210> SEQ ID NO 151
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 151
ggccuuugcu cagucggugu u 21

<210> SEQ ID NO 152
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 152
uuccugcacc ccaggccuuu u 21

<210> SEQ ID NO 153
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 153
uagcacuccu gcaccccagu u 21

<210> SEQ ID NO 154
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 154
gguagcacuc cugcaccccu u 21

<210> SEQ ID NO 155
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 155
ugccacagga ucuggauucu u 21

<210> SEQ ID NO 156
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 156
aauaaggggc ugccacaggu u 21

<210> SEQ ID NO 157
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 157
auaacaauaa ggggcugccu u 21

<210> SEQ ID NO 158
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 158
auaacaauaa ggggcugcca cuu 23

<210> SEQ ID NO 159
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 159
uauaacaaua aggggcugcu u 21

<210> SEQ ID NO 160
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 160
cguauaacaa uaaggggcuu u 21

<210> SEQ ID NO 161
<211> LENGTH: 21
<212> TYPE: RNA
<213> ORGANISM: Artificial Sequence
<220> FEATURE:

<223> OTHER INFORMATION: synthetic unmodified polynucleotide

<400> SEQUENCE: 161
uguauaacaa uaaggggcuu u 21

<210> SEQ ID NO 162
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 162
ucguauaaca auaaggggcu u 21

<210> SEQ ID NO 163
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 163
ucguauaaca auaaggggcu guu 23

<210> SEQ ID NO 164
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 164
cucguauaac aauaaggggu u 21

<210> SEQ ID NO 165
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 165
cucguauaac aauaaggggc uuu 23

<210> SEQ ID NO 166
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 166
uucguauaac aauaaggggu u 21

<210> SEQ ID NO 167
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 167
cgucugagca uugugucagu u 21

<210> SEQ ID NO 168
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 168
ugucugagca uugugucagu u 21

<210> SEQ ID NO 169
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 169
ugucugagca uugugucagg uuu 23

<210> SEQ ID NO 170
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 170
cgucugagca uugugucagg uuu 23

<210> SEQ ID NO 171
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 171
ugcgucugag cauugugucu u 21

<210> SEQ ID NO 172
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 172
cugcgucuga gcauuguguu u 21

<210> SEQ ID NO 173
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 173
cugcgucuga gcauuguguc auu 23

<210> SEQ ID NO 174
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 174
uugcgucuga gcauuguguc auu 23

<210> SEQ ID NO 175
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 175
uugcgucuga gcauuguguu u 21

<210> SEQ ID NO 176
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 176
uugcgucuga gcauuguguc a 21

<210> SEQ ID NO 177
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 177
uucagaagga gccucuaggu u 21

<210> SEQ ID NO 178
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 178
uucagaagga gccucuaggc uuu 23

<210> SEQ ID NO 179
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 179
uuguucagaa ggagccucuu u 21

<210> SEQ ID NO 180
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 180
ucuuugcuca guuggugcuu u 21

<210> SEQ ID NO 181
<211> LENGTH: 21

<212> TYPE: RNA
<213> ORGANISM: Artificial Sequence
<220> FEATURE:
<223> OTHER INFORMATION: synthetic unmodified polynucleotide

<400> SEQUENCE: 181
ugccacagga ucuggauuuu u 21

<210> SEQ ID NO 182
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 182
auaacaccaa ggggcugccu u 21

<210> SEQ ID NO 183
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 183
accaagcuug gcaaguucuu u 21

<210> SEQ ID NO 184
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 184
accaagcuug gcaaguucuu cuu 23

<210> SEQ ID NO 185
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 185
aaccaagcuu ggcaaguucu u 21

<210> SEQ ID NO 186
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 186
aaccaagcuu ggcaaguucu uuu 23

<210> SEQ ID NO 187
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 187
aguccgacua ugcugguguu u 21

<210> SEQ ID NO 188
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 188
agguccgacu augcuggugu u 21

<210> SEQ ID NO 189
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 189
ugguguaaca ccaagggcgu u 21

<210> SEQ ID NO 190
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 190
ugguguaaca ccaagggcga auu 23

<210> SEQ ID NO 191
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 191
augguguaac accaagggcu u 21

<210> SEQ ID NO 192
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 192
augguguaac accaagggcg auu 23

<210> SEQ ID NO 193
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 193
agauccaugg uguaacaccu u 21

<210> SEQ ID NO 194
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 194
uugcaaggac acuugauucu u 21

<210> SEQ ID NO 195
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 195
uugcaaggac acuugauucu guu 23

<210> SEQ ID NO 196
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 196
uugcaaggac acuugauucu g 21

<210> SEQ ID NO 197
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 197
guugcaagga cacuugauuu u 21

<210> SEQ ID NO 198
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 198
auugcaagga cacuugauuu u 21

<210> SEQ ID NO 199
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 199
auugcaagga cacuugauuc uuu 23

<210> SEQ ID NO 200
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 200
auugcaagga cacuugauuc u 21

<210> SEQ ID NO 201
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 201
aaguugcaag gacacuugau u 21

<210> SEQ ID NO 202
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 202
auuggugcuu cuucagaagu u 21

<210> SEQ ID NO 203
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 203
uguuggugcu ucuucagaau u 21

<210> SEQ ID NO 204
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 204
augucauaga ggaccaagau u 21

<210> SEQ ID NO 205
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 205
augucauaga ggaccaagac uuu 23

<210> SEQ ID NO 206
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 206
ugaugccagu guggugucau u 21

<210> SEQ ID NO 207
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 207
uggauaauau ucuguugucu u 21

<210> SEQ ID NO 208
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 208
agacauugug ucagguugcu u 21

<210> SEQ ID NO 209
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 209
cugucacugg acauuguguu u 21

<210> SEQ ID NO 210
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 210
uugucacugg acauuguguu u 21

<210> SEQ ID NO 211
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 211
ugauucuguc acuggacauu u 21

<210> SEQ ID NO 212
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 212
cuugauucug ucacuggacu u 21

<210> SEQ ID NO 213
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 213
uuugauucug ucacuggacu u 21

<210> SEQ ID NO 214

<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 214
acuugauucu gucacuggau u 21

<210> SEQ ID NO 215
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 215
uacuugauuc ugucacuggu u 21

<210> SEQ ID NO 216
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 216
uacuugauuc ugucacugga cuu 23

<210> SEQ ID NO 217
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 217
uacuugauuc ugucacugga c 21

<210> SEQ ID NO 218
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 218
ccuuccugua acaguggugu u 21

<210> SEQ ID NO 219
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 219
ucuuccugua acaguggugu u 21

<210> SEQ ID NO 220
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 220
uaccauuugg guaguauucu guu 23

<210> SEQ ID NO 221
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 221
ggucaggcca ccauuugggu u 21

<210> SEQ ID NO 222
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 222
cacugggauc caugguauau u 21

<210> SEQ ID NO 223
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 223
uacugggauc caugguauau u 21

<210> SEQ ID NO 224
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 224
aguuggugcu ucuucagaau u 21

<210> SEQ ID NO 225
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 225
aguuggugcu ucuucagaag guu 23

<210> SEQ ID NO 226
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 226
ucaguuggug cuucuucagu u 21

<210> SEQ ID NO 227
<211> LENGTH: 21
<212> TYPE: RNA

<213> ORGANISM: Artificial Sequence
<220> FEATURE:
<223> OTHER INFORMATION: synthetic unmodified polynucleotide

<400> SEQUENCE: 227
acuguuuuca guuggugcuu u 21

<210> SEQ ID NO 228
<211> LENGTH: 23
<212> TYPE: RNA
<213> ORGANISM: Artificial Sequence
<220> FEATURE:
<223> OTHER INFORMATION: synthetic unmodified polynucleotide

<400> SEQUENCE: 228
acuguuuuca guuggugcuu cuu 23

<210> SEQ ID NO 229
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 229
uucugugcuu ggaaccgggu u 21

<210> SEQ ID NO 230
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 230
uagaaggagc cucugugcuu u 21

<210> SEQ ID NO 231
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 231
guggugcuug uucagaaggu u 21

<210> SEQ ID NO 232
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 232
auggugcuug uucagaaggu u 21

<210> SEQ ID NO 233
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 233
uaccugauuc uguuucugau u 21

<210> SEQ ID NO 234
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 234
ucuaggacac cugauucugu u 21

<210> SEQ ID NO 235
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 235
aagaaugugc cucgauaacu u 21

<210> SEQ ID NO 236
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 236
ggagaaugug ccucgauaau u 21

<210> SEQ ID NO 237
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 237
agagaaugug ccucgauaau u 21

<210> SEQ ID NO 238
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 238
uugugucuga gcaucgcguu u 21

<210> SEQ ID NO 239
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 239
uacagucccu ucugugucuu u 21

<210> SEQ ID NO 240
<211> LENGTH: 21
<212> TYPE: RNA
<213> ORGANISM: Artificial Sequence
<220> FEATURE:

<223> OTHER INFORMATION: synthetic unmodified polynucleotide

<400> SEQUENCE: 240
uuacaaugcu uccaggacau u 21

<210> SEQ ID NO 241
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 241
augcuuucca aaccuuguuu u 21

<210> SEQ ID NO 242
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 242
ccugagcaaa gccaugugau u 21

<210> SEQ ID NO 243
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 243
cugagcaaag ccaugugguu u 21

<210> SEQ ID NO 244
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 244
gugguccagg auugcuacuu u 21

<210> SEQ ID NO 245
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)

-continued

<223> OTHER INFORMATION: combination of 2'-fluoro, 2'-O-methyl, phosphorothioate linked ribonucleotides

<400> SEQUENCE: 245
ccacagaaaa cuacccaaau u 21

<210> SEQ ID NO 246
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 246
cagaagggac ugccgucguu u 21

<210> SEQ ID NO 247
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 247
agaagggacu gccgucgcgu u 21

<210> SEQ ID NO 248
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 248
agaagggacu gccgucgcau u 21

<210> SEQ ID NO 249
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 249
gcuccuuccg aacaagcauu u 21

<210> SEQ ID NO 250
<211> LENGTH: 21
<212> TYPE: RNA

<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 250
cuccuuccga acaagcacuu u 21

<210> SEQ ID NO 251
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 251
cuuccgaaca agcaccgacu u 21

<210> SEQ ID NO 252
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 252
cuuccgaaca agcaccgauu u 21

<210> SEQ ID NO 253
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 253
uuccgaacaa gcaccgacuu u 21

<210> SEQ ID NO 254
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 254

-continued ccuuccgaac aagcaccgac u 21

<210> SEQ ID NO 255
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 255
uuccgaacaa gcaccgacuu u 21

<210> SEQ ID NO 256
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 256
ccuuccgaac aagcaccgac u 21

<210> SEQ ID NO 257
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 257
ccuuccgaac aagcaccgac 20

<210> SEQ ID NO 258
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 258
ccuuccgaac aagcaccgac u 21

<210> SEQ ID NO 259
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 259
uccgaacaag caccgacuau u 21

<210> SEQ ID NO 260
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 260
cgaacaagca ccgacugagu u 21

<210> SEQ ID NO 261
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 261
agcaccgacu gagcaaagau u 21

<210> SEQ ID NO 262
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 262
gcaccgacug agcaaagguu u 21

<210> SEQ ID NO 263
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 263
caccgacuga gcaaaggccu u 21

<210> SEQ ID NO 264
<211> LENGTH: 21

<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 264
aaggccuggg gugcaggaau u 21

<210> SEQ ID NO 265
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 265
cuggggugca ggagugcuau u 21

<210> SEQ ID NO 266
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 266
cuggggugca ggagugcuau 20

<210> SEQ ID NO 267
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 267
ggggugcagg agugcuaccu u 21

<210> SEQ ID NO 268
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 268
gaauccagau ccuguggcau u 21

<210> SEQ ID NO 269
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 269
ccuguggcag ccccuuauuu u 21

<210> SEQ ID NO 270
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 270
ggcagccccu uauuguuauu u 21

<210> SEQ ID NO 271
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 271
ggcagccccu uauuguuauu u 21

<210> SEQ ID NO 272
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 272
ggcagccccu uauuguuauu u 21

<210> SEQ ID NO 273
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:

```
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 273

guggcagccc cuuauuguua u                                              21


<210> SEQ ID NO 274
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 274

guggcagccc cuuauuguua                                                20


<210> SEQ ID NO 275
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
      abasic, phosphorothioate linked ribonucleotides

<400> SEQUENCE: 275

guggcagccc cuuauuguua u                                              21


<210> SEQ ID NO 276
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 276

gcagccccuu auuguuauau u                                              21


<210> SEQ ID NO 277
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 277

agccccuuau uguuauacgu u                                              21


<210> SEQ ID NO 278
```

<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 278
agccccuuau uguuauacau u 21

<210> SEQ ID NO 279
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 279
gccccuuauu guuauacgau u 21

<210> SEQ ID NO 280
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 280
gccccuuauu guuauacgau u 21

<210> SEQ ID NO 281
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 281
cagccccuua uuguuauacg 20

<210> SEQ ID NO 282
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 282
ccccuuauug uuauacgagu u 21

<210> SEQ ID NO 283
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 283
agccccuuau uguuauacga g 21

<210> SEQ ID NO 284
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 284
agccccuuau uguuauacga 20

<210> SEQ ID NO 285
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 285
ccccuuauug uuauacgaau u 21

<210> SEQ ID NO 286
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 286
agccccuuau uguuauacga g 21

<210> SEQ ID NO 287
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 287
cugacacaau gcucagacgu u 21

<210> SEQ ID NO 288
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 288
cugacacaau gcucagacau u 21

<210> SEQ ID NO 289
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 289
cugacacaau gcucagacau u 21

<210> SEQ ID NO 290
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 290
accugacaca augcucagac a 21

<210> SEQ ID NO 291
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 291
accugacaca augcucagac a 21

```
<210> SEQ ID NO 292
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 292

accugacaca augcucagac                                              20


<210> SEQ ID NO 293
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
      abasic, phosphorothioate linked ribonucleotides

<400> SEQUENCE: 293

accugacaca augcucagac a                                            21


<210> SEQ ID NO 294
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
      abasic, phosphorothioate linked ribonucleotides

<400> SEQUENCE: 294

cugacacaau gcucagacgu u                                            21


<210> SEQ ID NO 295
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
      abasic, phosphorothioate linked ribonucleotides

<400> SEQUENCE: 295

accugacaca augcucagac g                                            21


<210> SEQ ID NO 296
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides
```

<400> SEQUENCE: 296
accugacaca augcucagac g 21

<210> SEQ ID NO 297
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 297
gacacaaugc ucagacgcau u 21

<210> SEQ ID NO 298
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 298
acacaaugcu cagacgcagu u 21

<210> SEQ ID NO 299
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 299
ugacacaaug cucagacgca g 21

<210> SEQ ID NO 300
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 300
ugacacaaug cucagacgca a 21

<210> SEQ ID NO 301
<211> LENGTH: 20
<212> TYPE: RNA
<213> ORGANISM: Artificial Sequence
<220> FEATURE:

<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 301
ugacacaaug cucagacgca 20

<210> SEQ ID NO 302
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 302
ugacacaaug cucagacgca a 21

<210> SEQ ID NO 303
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 303
ugacacaaug cucagacgca 20

<210> SEQ ID NO 304
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 304
acacaaugcu cagacgcaau 20

<210> SEQ ID NO 305
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 305
acacaaugcu cagacgcaau u 21

```
<210> SEQ ID NO 306
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
      abasic, phosphorothioate linked ribonucleotides

<400> SEQUENCE: 306

acacaaugcu cagacgcaau u                                              21


<210> SEQ ID NO 307
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted
      abasic, phosphorothioate linked ribonucleotides

<400> SEQUENCE: 307

acacaaugcu cagacgca                                                  18


<210> SEQ ID NO 308
<211> LENGTH: 19
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(19)
<223> OTHER INFORMATION: combination of 2'-fluoro, 2'-O-methyl, inverted
      abasic, phosphorothioate linked ribonucleotides

<400> SEQUENCE: 308

acacaaugcu cagacgcaa                                                 19


<210> SEQ ID NO 309
<211> LENGTH: 19
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(19)
<223> OTHER INFORMATION: combination of 2'-fluoro, 2'-O-methyl, inverted
      abasic, phosphorothioate linked ribonucleotides

<400> SEQUENCE: 309

acacaaugcu cagacgcaa                                                 19


<210> SEQ ID NO 310
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
```

abasic, phosphorothioate linked ribonucleotides

<400> SEQUENCE: 310
ugacacaaug cucagacgca a 21

<210> SEQ ID NO 311
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 311
ugacacaaug cucagacgca 20

<210> SEQ ID NO 312
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 312
ccuagaggcu ccuucugaau u 21

<210> SEQ ID NO 313
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 313
ccuagaggcu ccuucugaau u 21

<210> SEQ ID NO 314
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 314
agccuagagg cuccuucuga a 21

<210> SEQ ID NO 315
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 315
ccuagaggcu ccuucugaau u 21

<210> SEQ ID NO 316
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 316
agccuagagg cuccuucuga 20

<210> SEQ ID NO 317
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 317
agccuagagg cuccuucuga a 21

<210> SEQ ID NO 318
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 318
ccuagaggcu ccuucugaau u 21

<210> SEQ ID NO 319
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 319
agccuagagg cuccuucuga 20

<210> SEQ ID NO 320
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 320
agaggcuccu ucugaacaau u 21

<210> SEQ ID NO 321
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 321
agcaccaacu gagcaaagau u 21

<210> SEQ ID NO 322
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 322
aaauccagau ccuguggcau u 21

<210> SEQ ID NO 323
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 323
ggcagccccu ugguguuauu u 21

<210> SEQ ID NO 324
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)

<223> OTHER INFORMATION: combination of 2'-fluoro, 2'-O-methyl,
      phosphorothioate linked ribonucleotides

<400> SEQUENCE: 324
agaacuugcc aagcuugguu u                                            21

<210> SEQ ID NO 325
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
      abasic, phosphorothioate linked ribonucleotides

<400> SEQUENCE: 325
agaacuugcc aagcuugguu u                                            21

<210> SEQ ID NO 326
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 326
gaagaacuug ccaagcuugg u                                            21

<210> SEQ ID NO 327
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 327
gaagaacuug ccaagcuugg                                              20

<210> SEQ ID NO 328
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
      abasic, phosphorothioate linked ribonucleotides

<400> SEQUENCE: 328
gaagaacuug ccaagcuugg u                                            21

<210> SEQ ID NO 329
<211> LENGTH: 21
<212> TYPE: RNA

<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 329
gaacuugcca agcuugguuu u 21

<210> SEQ ID NO 330
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 330
gaacuugcca agcuugguuu u 21

<210> SEQ ID NO 331
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 331
aagaacuugc caagcuuggu u 21

<210> SEQ ID NO 332
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 332
aagaacuugc caagcuuggu 20

<210> SEQ ID NO 333
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 333
aagaacuugc caagcuuggu u 21

<210> SEQ ID NO 334
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 334
acaccagcau agucggacuu u 21

<210> SEQ ID NO 335
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 335
caccagcaua gucggaccuu u 21

<210> SEQ ID NO 336
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 336
cgcccuuggu guuacaccau u 21

<210> SEQ ID NO 337
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 337
uucgcccuug guguuacacc a 21

<210> SEQ ID NO 338
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
abasic, phosphorothioate linked ribonucleotides

<400> SEQUENCE: 338
cgcccuuggu guuacaccau u 21

<210> SEQ ID NO 339
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted
abasic, phosphorothioate linked ribonucleotides

<400> SEQUENCE: 339
cgcccuuggu guuacacc 18

<210> SEQ ID NO 340
<211> LENGTH: 19
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(19)
<223> OTHER INFORMATION: combination of 2'-fluoro, 2'-O-methyl, inverted
abasic, phosphorothioate linked ribonucleotides

<400> SEQUENCE: 340
cgcccuuggu guuacacca 19

<210> SEQ ID NO 341
<211> LENGTH: 19
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(19)
<223> OTHER INFORMATION: combination of 2'-fluoro, 2'-O-methyl, inverted
abasic, phosphorothioate linked ribonucleotides

<400> SEQUENCE: 341
cgcccuuggu guuacacca 19

<210> SEQ ID NO 342
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
abasic, phosphorothioate linked ribonucleotides

<400> SEQUENCE: 342
uucgcccuug guguuacacc 20

<210> SEQ ID NO 343
<211> LENGTH: 21

```
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 343

gcccuuggug uuacaccauu u                                              21


<210> SEQ ID NO 344
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 344

ucgcccuugg uguuacacca                                                20


<210> SEQ ID NO 345
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 345

ucgcccuugg uguuacacca                                                20


<210> SEQ ID NO 346
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 346

gcccuuggug uuacaccauu                                                20


<210> SEQ ID NO 347
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 347
```

```
gguguuacac cauggaucuu u                                              21


<210> SEQ ID NO 348
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 348

gaaucaagug uccuugcaau u                                              21


<210> SEQ ID NO 349
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 349

cagaaucaag uguccuugca                                                20


<210> SEQ ID NO 350
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 350

gaaucaagug uccuugcaau                                                20


<210> SEQ ID NO 351
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 351

cagaaucaag uguccuugca                                                20


<210> SEQ ID NO 352
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
```

<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 352
gaaucaagug uccuugcaau u 21

<210> SEQ ID NO 353
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 353
gaaucaagug uccuugca 18

<210> SEQ ID NO 354
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 354
gaaucaagug uccuugca 18

<210> SEQ ID NO 355
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 355
gaaucaagug uccuugca 18

<210> SEQ ID NO 356
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 356
cagaaucaag uguccuugca 20

<210> SEQ ID NO 357

<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 357
cagaaucaag uguccuugca 20

<210> SEQ ID NO 358
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 358
aaucaagugu ccuugcaacu u 21

<210> SEQ ID NO 359
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 359
aaucaagugu ccuugcaauu u 21

<210> SEQ ID NO 360
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 360
agaaucaagu guccuugcaa 20

<210> SEQ ID NO 361
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 361
agaaucaagu guccuugcaa u 21

<210> SEQ ID NO 362
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 362
aaucaagugu ccuugcaauu 20

<210> SEQ ID NO 363
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 363
aaucaagugu ccuugcaauu u 21

<210> SEQ ID NO 364
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 364
aaucaagugu ccuugcaa 18

<210> SEQ ID NO 365
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 365
agaaucaagu guccuugcaa 20

<210> SEQ ID NO 366
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 366
aaucaagugu ccuugcaauu 20

<210> SEQ ID NO 367
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 367
aaucaagugu ccuugcaa 18

<210> SEQ ID NO 368
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 368
aaucaagugu ccuugcaauu 20

<210> SEQ ID NO 369
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 369
aaucaagugu ccuugcaa 18

<210> SEQ ID NO 370
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 370
agaaucaagu guccuugcaa 20

<210> SEQ ID NO 371
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 371
agaaucaagu guccuugcaa 20

<210> SEQ ID NO 372
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 372
agaaucaagu guccuugcaa 20

<210> SEQ ID NO 373
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 373
ucaagugucc uugcaacuuu u 21

<210> SEQ ID NO 374
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 374
cuucugaaga agcaccaauu u 21

<210> SEQ ID NO 375
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 375
uucugaagaa gcaccaacau u 21

<210> SEQ ID NO 376
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 376 ucuuggucu cuaugacauu u 21

<210> SEQ ID NO 377
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 377
agucuugguc cucuaugaca 20

<210> SEQ ID NO 378
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 378
agucuugguc cucuaugaca 20

<210> SEQ ID NO 379
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 379 ucuuggucu cuaugacauu u 21

<210> SEQ ID NO 380
<211> LENGTH: 20
<212> TYPE: RNA
<213> ORGANISM: Artificial Sequence
<220> FEATURE:

<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 380
ucuugguccu cuaugacauu 20

<210> SEQ ID NO 381
<211> LENGTH: 19
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(19)
<223> OTHER INFORMATION: combination of 2'-fluoro, 2'-O-methyl, inverted abasic, phosphorothioate linked ribonucleotides

<400> SEQUENCE: 381
ucuugguccu cuaugacau 19

<210> SEQ ID NO 382
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 382
ucuugguccu cuaugaca 18

<210> SEQ ID NO 383
<211> LENGTH: 19
<212> TYPE: RNA
<213> ORGANISM: Artificial Sequence
<220> FEATURE:
<223> OTHER INFORMATION: combination of 2'-fluoro, 2'-O-methyl, inverted abasic, phosphorothioate linked ribonucleotides
<220> FEATURE:
<221> NAME/KEY: modified_base
<222> LOCATION: (1)..(19)
<223> OTHER INFORMATION: combination of 2'-fluoro, 2'-O-methyl, inverted abasic, phosphorothioate linked ribonucleotides

<400> SEQUENCE: 383
ucuugguccu cuaugacau 19

<210> SEQ ID NO 384
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 384
ugacaccaca cuggcaucau u 21

<210> SEQ ID NO 385
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 385
gacaacagaa uauuauccau 20

<210> SEQ ID NO 386
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 386
gcaaccugac acaaugucuu u 21

<210> SEQ ID NO 387
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 387
acacaauguc cagugacagu u 21

<210> SEQ ID NO 388
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 388
acacaauguc cagugacaau u 21

<210> SEQ ID NO 389
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)

<223> OTHER INFORMATION: combination of 2'-fluoro, 2'-O-methyl,
      phosphorothioate linked ribonucleotides

<400> SEQUENCE: 389
auguccagug acagaaucau u                                              21

<210> SEQ ID NO 390
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 390
guccagugac agaaucaagu u                                              21

<210> SEQ ID NO 391
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 391
guccagugac agaaucaaau u                                              21

<210> SEQ ID NO 392
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 392
uccagugaca gaaucaaguu u                                              21

<210> SEQ ID NO 393
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 393
ccagugacag aaucaaguau u                                              21

<210> SEQ ID NO 394
<211> LENGTH: 21
<212> TYPE: RNA

<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 394
guccagugac agaaucaagu a 21

<210> SEQ ID NO 395
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 395
guccagugac agaaucaagu 20

<210> SEQ ID NO 396
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 396
guccagugac agaaucaagu 20

<210> SEQ ID NO 397
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 397
ccagugacag aaucaaguau 20

<210> SEQ ID NO 398
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 398
ccagugacag aaucaaguau u 21

<210> SEQ ID NO 399
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 399
ccagugacag aaucaaguau 20

<210> SEQ ID NO 400
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 400
ccagugacag aaucaaguau 20

<210> SEQ ID NO 401
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 401
ccagugacag aaucaagu 18

<210> SEQ ID NO 402
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 402
ccagugacag aaucaagu 18

<210> SEQ ID NO 403
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted abasic, phosphorothioate linked ribonucleotides

<400> SEQUENCE: 403
ccagugacag aaucaagu 18

<210> SEQ ID NO 404
<211> LENGTH: 19
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(19)
<223> OTHER INFORMATION: combination of 2'-fluoro, 2'-O-methyl, inverted abasic, phosphorothioate linked ribonucleotides

<400> SEQUENCE: 404
guccagugac agaaucaau 19

<210> SEQ ID NO 405
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 405
guccagugac agaaucaagu 20

<210> SEQ ID NO 406
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 406
caccacuguu acaggaaggu u 21

<210> SEQ ID NO 407
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 407
caccacuguu acaggaagau u 21

<210> SEQ ID NO 408
<211> LENGTH: 20

<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 408
cagaauacua cccaaauggu 20

<210> SEQ ID NO 409
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 409
cccaaauggu ggccugaccu u 21

<210> SEQ ID NO 410
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 410
uauaccaugg aucccagugu u 21

<210> SEQ ID NO 411
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 411
uauaccaugg aucccaguau u 21

<210> SEQ ID NO 412
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 412
uucugaagaa gcaccaacuu u 21

<210> SEQ ID NO 413
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted abasic, phosphorothioate linked ribonucleotides

<400> SEQUENCE: 413
uucugaagaa gcaccaacuu u 21

<210> SEQ ID NO 414
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 414
ccuucugaag aagcaccaac u 21

<210> SEQ ID NO 415
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 415
ccuucugaag aagcaccaac 20

<210> SEQ ID NO 416
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 416
ccuucugaag aagcaccaac 20

<210> SEQ ID NO 417
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:

<221> NAME/KEY: modified_base
<222> LOCATION: (1)..(21)
<223> OTHER INFORMATION: combination of 2'-fluoro, 2'-O-methyl, inverted
abasic, phosphorothioate linked ribonucleotides

<400> SEQUENCE: 417
ccuucugaag aagcaccaac u 21

<210> SEQ ID NO 418
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
abasic, phosphorothioate linked ribonucleotides

<400> SEQUENCE: 418
uucugaagaa gcaccaacuu u 21

<210> SEQ ID NO 419
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
abasic, phosphorothioate linked ribonucleotides

<400> SEQUENCE: 419
ccuucugaag aagcaccaac 20

<210> SEQ ID NO 420
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, inverted
abasic, phosphorothioate linked ribonucleotides

<400> SEQUENCE: 420
ccuucugaag aagcaccaac u 21

<210> SEQ ID NO 421
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
phosphorothioate linked ribonucleotides

<400> SEQUENCE: 421
cugaagaagc accaacugau u 21

<210> SEQ ID NO 422

<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 422
agcaccaacu gaaaacaguu u 21

<210> SEQ ID NO 423
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 423
gaagcaccaa cugaaaacag 20

<210> SEQ ID NO 424
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 424
cccgguucca agcacagaau u 21

<210> SEQ ID NO 425
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 425
agcacagagg cuccuucuau u 21

<210> SEQ ID NO 426
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 426
ccuucugaac aagcaccacu u 21

<210> SEQ ID NO 427
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 427
ccuucugaac aagcaccauu u 21

<210> SEQ ID NO 428
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 428
ucagaaacag aaucagguau u 21

<210> SEQ ID NO 429
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 429
cagaaucagg uguccuagau u 21

<210> SEQ ID NO 430
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 430
guuaucgagg cacauucuuu u 21

<210> SEQ ID NO 431
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 431
uuaucgaggc acauucuccu u 21

<210> SEQ ID NO 432
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 432
uuaucgaggc acauucucuu u 21

<210> SEQ ID NO 433
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 433
acgcgaugcu cagacacaau u 21

<210> SEQ ID NO 434
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 434
agacacagaa gggacuguau u 21

<210> SEQ ID NO 435
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 435
uguccuggaa gcauuguaau u 21

```
<210> SEQ ID NO 436
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 436

aacaagguuu ggaaagcauu u                                              21


<210> SEQ ID NO 437
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 437

ucacauggcu uugcucaggu u                                              21


<210> SEQ ID NO 438
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 438

accacauggc uuugcucagu u                                              21


<210> SEQ ID NO 439
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 439

aguagcaauc cuggaccacu u                                              21


<210> SEQ ID NO 440
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides
```

<400> SEQUENCE: 440
uuuggguagu uuucuguggu u 21

<210> SEQ ID NO 441
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 441
acgacggcag ucccuucugu u 21

<210> SEQ ID NO 442
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 442
cgcgacggca gucccuucuu u 21

<210> SEQ ID NO 443
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 443
ugcgacggca gucccuucuu u 21

<210> SEQ ID NO 444
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 444
augcuuguuc ggaaggagcu u 21

<210> SEQ ID NO 445
<211> LENGTH: 21
<212> TYPE: RNA
<213> ORGANISM: Artificial Sequence
<220> FEATURE:

<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 445
agugcuuguu cggaaggagu u 21

<210> SEQ ID NO 446
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 446
gucggugcuu guucggaagu u 21

<210> SEQ ID NO 447
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 447
aucggugcuu guucggaagu u 21

<210> SEQ ID NO 448
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 448
agucggugcu uguucggaau u 21

<210> SEQ ID NO 449
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 449
agucggugcu uguucggaag guu 23

<210> SEQ ID NO 450
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 450
agucggugcu uguucggaag guu 23

<210> SEQ ID NO 451
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 451
uagucggugc uuguucggau u 21

<210> SEQ ID NO 452
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 452
cucagucggu gcuuguucgu u 21

<210> SEQ ID NO 453
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 453
ucuuugcuca gucggugcuu u 21

<210> SEQ ID NO 454
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 454
accuuugcuc agucggugcu u 21

<210> SEQ ID NO 455
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 455
ggccuuugcu cagucggugu u 21

<210> SEQ ID NO 456
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 456
uuccugcacc ccaggccuuu u 21

<210> SEQ ID NO 457
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 457
uagcacuccu gcaccccagu u 21

<210> SEQ ID NO 458
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 458
uagcacuccu gcaccccagu u 21

<210> SEQ ID NO 459
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 459
gguagcacuc cugcaccccu u 21

<210> SEQ ID NO 460
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 460
ugccacagga ucuggauucu u 21

<210> SEQ ID NO 461
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 461
aauaaggggc ugccacaggu u 21

<210> SEQ ID NO 462
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 462
auaacaauaa ggggcugccu u 21

<210> SEQ ID NO 463
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 463
auaacaauaa ggggcugccu u 21

<210> SEQ ID NO 464
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 464
auaacaauaa ggggcugcca cuu 23

<210> SEQ ID NO 465
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 465
auaacaauaa ggggcugcca cuu 23

<210> SEQ ID NO 466
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 466
uauaacaaua aggggcugcu u 21

<210> SEQ ID NO 467
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 467
cguauaacaa uaaggggcuu u 21

<210> SEQ ID NO 468
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)

<223> OTHER INFORMATION: combination of 2'-fluoro, 2'-O-methyl,
      phosphorothioate linked ribonucleotides

<400> SEQUENCE: 468
uguauaacaa uaaggggcuu u                                                21

<210> SEQ ID NO 469
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 469
ucguauaaca auaaggggcu u                                                21

<210> SEQ ID NO 470
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 470
ucguauaaca auaaggggcu guu                                              23

<210> SEQ ID NO 471
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 471
cucguauaac aauaaggggu u                                                21

<210> SEQ ID NO 472
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 472
cucguauaac aauaaggggc uuu                                              23

<210> SEQ ID NO 473
<211> LENGTH: 21
<212> TYPE: RNA

-continued

<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 473
uucguauaac aauaaggggu u 21

<210> SEQ ID NO 474
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 474
cgucugagca uugugucagu u 21

<210> SEQ ID NO 475
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 475
ugucugagca uugugucagu u 21

<210> SEQ ID NO 476
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 476
ugucugagca uugugucagg uuu 23

<210> SEQ ID NO 477
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 477
ugucugagca uugugucagg uuu 23

<210> SEQ ID NO 478
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 478
ugucugagca uugugucagg uuu 23

<210> SEQ ID NO 479
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 479
ugucugagca uugugucagg uuu 23

<210> SEQ ID NO 480
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 480
ugucugagca uugugucagg uuu 23

<210> SEQ ID NO 481
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 481
ugucugagca uugugucagg uuu 23

<210> SEQ ID NO 482
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 482
ugucugagca uugugucagg uuu 23

<210> SEQ ID NO 483
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 483
cgucugagca uugugucagg uuu 23

<210> SEQ ID NO 484
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 484
ugcgucugag cauugugucu u 21

<210> SEQ ID NO 485
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 485
cugcgucuga gcauuguguu u 21

<210> SEQ ID NO 486
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 486
cugcgucuga gcauuguguc auu 23

<210> SEQ ID NO 487
<211> LENGTH: 23

<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 487
uugcgucuga gcauuguguc auu 23

<210> SEQ ID NO 488
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 488
uugcgucuga gcauuguguc auu 23

<210> SEQ ID NO 489
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 489
uugcgucuga gcauuguguc auu 23

<210> SEQ ID NO 490
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 490
uugcgucuga gcauuguguc auu 23

<210> SEQ ID NO 491
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 491
uugcgucuga gcauuguguc auu 23

<210> SEQ ID NO 492
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 492
uugcgucuga gcauuguguu u 21

<210> SEQ ID NO 493
<211> LENGTH: 21
<212> TYPE: DNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 493
uugcgucuga gcauuguguu u 21

<210> SEQ ID NO 494
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 494
uugcgucuga gcauuguguc auu 23

<210> SEQ ID NO 495
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 495
uugcgucuga gcauuguguc auu 23

<210> SEQ ID NO 496
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:

<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 496
uugcgucuga gcauuguguc a 21

<210> SEQ ID NO 497
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 497
uucagaagga gccucuaggu u 21

<210> SEQ ID NO 498
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 498
uucagaagga gccucuaggu u 21

<210> SEQ ID NO 499
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 499
uucagaagga gccucuaggc uuu 23

<210> SEQ ID NO 500
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 500
uucagaagga gccucuaggu u 21

<210> SEQ ID NO 501

```
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 501

uucagaagga gccucuaggc uuu                                              23


<210> SEQ ID NO 502
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 502

uuguucagaa ggagccucuu u                                                21


<210> SEQ ID NO 503
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 503

ucuuugcuca guuggugcuu u                                                21


<210> SEQ ID NO 504
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 504

ugccacagga ucuggauuuu u                                                21


<210> SEQ ID NO 505
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides
```

<400> SEQUENCE: 505
auaacaccaa ggggcugccu u 21

<210> SEQ ID NO 506
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 506
accaagcuug gcaaguucuu u 21

<210> SEQ ID NO 507
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 507
accaagcuug gcaaguucuu cuu 23

<210> SEQ ID NO 508
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 508
aaccaagcuu ggcaaguucu u 21

<210> SEQ ID NO 509
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 509
aaccaagcuu ggcaaguucu uuu 23

<210> SEQ ID NO 510
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 510
aguccgacua ugcugguguu u                                               21

<210> SEQ ID NO 511
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 511
agguccgacu augcuggugu u                                               21

<210> SEQ ID NO 512
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 512
ugguguaaca ccaagggcgu u                                               21

<210> SEQ ID NO 513
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 513
ugguguaaca ccaagggcga auu                                             23

<210> SEQ ID NO 514
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 514
ugguguaaca ccaagggcgu u                                               21

```
<210> SEQ ID NO 515
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 515

ugguguaaca ccaagggcgu u                                            21


<210> SEQ ID NO 516
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 516

ugguguaaca ccaagggcga auu                                          23


<210> SEQ ID NO 517
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 517

ugguguaaca ccaagggcga auu                                          23


<210> SEQ ID NO 518
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 518

augguguaac accaagggcu u                                            21


<210> SEQ ID NO 519
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides
```

<400> SEQUENCE: 519 auggguaac accaagggcg auu 23

<210> SEQ ID NO 520
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 520
augguguaac accaagggcg auu 23

<210> SEQ ID NO 521
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 521
augguguaac accaagggcu u 21

<210> SEQ ID NO 522
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 522
agauccaugg uguaacaccu u 21

<210> SEQ ID NO 523
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 523
uugcaaggac acuugauucu u 21

<210> SEQ ID NO 524
<211> LENGTH: 23
<212> TYPE: RNA
<213> ORGANISM: Artificial Sequence
<220> FEATURE:

<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 524
uugcaaggac acuugauucu guu 23

<210> SEQ ID NO 525
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 525
uugcaaggac acuugauucu u 21

<210> SEQ ID NO 526
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 526
uugcaaggac acuugauucu guu 23

<210> SEQ ID NO 527
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 527
uugcaaggac acuugauucu u 21

<210> SEQ ID NO 528
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 528
uugcaaggac acuugauucu u 21

<210> SEQ ID NO 529
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 529
uugcaaggac acuugauucu guu 23

<210> SEQ ID NO 530
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 530
uugcaaggac acuugauucu g 21

<210> SEQ ID NO 531
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 531
uugcaaggac acuugauucu g 21

<210> SEQ ID NO 532
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 532
guugcaagga cacuugauuu u 21

<210> SEQ ID NO 533
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 533
auugcaagga cacuugauuu u 21

<210> SEQ ID NO 534
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 534
auugcaagga cacuugauuc uuu 23

<210> SEQ ID NO 535
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 535
auugcaagga cacuugauuc uuu 23

<210> SEQ ID NO 536
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 536
auugcaagga cacuugauuu u 21

<210> SEQ ID NO 537
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 537
auugcaagga cacuugauuu u 21

<210> SEQ ID NO 538
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 538
auugcaagga cacuugauuc uuu 23

<210> SEQ ID NO 539
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 539
auugcaagga cacuugauuu u 21

<210> SEQ ID NO 540
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 540
auugcaagga cacuugauuc u 21

<210> SEQ ID NO 541
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 541
auugcaagga cacuugauuc u 21

<210> SEQ ID NO 542
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 542
aaguugcaag gacacuugau u 21

<210> SEQ ID NO 543
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 543
auuggugcuu cuucagaagu u 21

<210> SEQ ID NO 544
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 544
uguuggugcu ucuucagaau u 21

<210> SEQ ID NO 545
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 545
augucauaga ggaccaagau u 21

<210> SEQ ID NO 546
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 546
augucauaga ggaccaagac uuu 23

<210> SEQ ID NO 547
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)

<223> OTHER INFORMATION: combination of 2'-fluoro, 2'-O-methyl, phosphorothioate linked ribonucleotides

<400> SEQUENCE: 547
augucauaga ggaccaagac uuu 23

<210> SEQ ID NO 548
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 548
augucauaga ggaccaagau u 21

<210> SEQ ID NO 549
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 549
augucauaga ggaccaagau u 21

<210> SEQ ID NO 550
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 550
augucauaga ggaccaagac uuu 23

<210> SEQ ID NO 551
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 551
ugaugccagu guggugucau u 21

<210> SEQ ID NO 552
<211> LENGTH: 21
<212> TYPE: RNA

<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 552
uggauaauau ucuguugucu u 21

<210> SEQ ID NO 553
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 553
agacauugug ucagguugcu u 21

<210> SEQ ID NO 554
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 554
cugucacugg acauuguguu u 21

<210> SEQ ID NO 555
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 555
uugucacugg acauuguguu u 21

<210> SEQ ID NO 556
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 556
ugauucuguc acuggacauu u 21

<210> SEQ ID NO 557
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 557
cuugauucug ucacuggacu u 21

<210> SEQ ID NO 558
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 558
uuugauucug ucacuggacu u 21

<210> SEQ ID NO 559
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 559
acuugauucu gucacuggau u 21

<210> SEQ ID NO 560
<211> LENGTH: 21
<212> TYPE: RNA
<213> ORGANISM: Artificial Sequence
<220> FEATURE:
<223> OTHER INFORMATION: combination of 2'-fluoro, 2'-O-methyl, phosphorothioate linked ribonucleotides
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 560
uacuugauuc ugucacuggu u 21

<210> SEQ ID NO 561
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:

```
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 561

uacuugauuc ugucacugga cuu                                        23


<210> SEQ ID NO 562
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 562

uacuugauuc ugucacugga cuu                                        23


<210> SEQ ID NO 563
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 563

uacuugauuc ugucacuggu u                                          21


<210> SEQ ID NO 564
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 564

uacuugauuc ugucacuggu u                                          21


<210> SEQ ID NO 565
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 565

uacuugauuc ugucacuggu u                                          21


<210> SEQ ID NO 566
```

<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
phosphorothioate linked ribonucleotides

<400> SEQUENCE: 566
uacuugauuc ugucacuggu u 21

<210> SEQ ID NO 567
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
phosphorothioate linked ribonucleotides

<400> SEQUENCE: 567
uacuugauuc ugucacugga cuu 23

<210> SEQ ID NO 568
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
phosphorothioate linked ribonucleotides

<400> SEQUENCE: 568
uacuugauuc ugucacugga cuu 23

<210> SEQ ID NO 569
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
phosphorothioate linked ribonucleotides

<400> SEQUENCE: 569
uacuugauuc ugucacugga c 21

<210> SEQ ID NO 570
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
phosphorothioate linked ribonucleotides

<400> SEQUENCE: 570
ccuuccugua acaguggugu u 21

<210> SEQ ID NO 571
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 571
ucuuccugua acaguggugu u 21

<210> SEQ ID NO 572
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 572
uaccauuugg guaguauucu guu 23

<210> SEQ ID NO 573
<211> LENGTH: 21
<212> TYPE: RNA
<213> ORGANISM: Artificial Sequence
<220> FEATURE:
<223> OTHER INFORMATION: synthetic modified polynucleotide

<400> SEQUENCE: 573
ggucaggcca ccauuugggu u 21

<210> SEQ ID NO 574
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 574
cacugggauc caugguauau u 21

<210> SEQ ID NO 575
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 575
uacugggauc caugguauau u 21

<210> SEQ ID NO 576
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 576
aguuggugcu ucuucagaau u 21

<210> SEQ ID NO 577
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 577
aguuggugcu ucuucagaag guu 23

<210> SEQ ID NO 578
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 578
aguuggugcu ucuucagaag guu 23

<210> SEQ ID NO 579
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 579
aguuggugcu ucuucagaag guu 23

<210> SEQ ID NO 580
<211> LENGTH: 23
<212> TYPE: RNA
<213> ORGANISM: Artificial Sequence
<220> FEATURE:

```
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 580

aguuggugcu ucuucagaag guu                                          23


<210> SEQ ID NO 581
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 581

aguuggugcu ucuucagaag guu                                          23


<210> SEQ ID NO 582
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 582

aguuggugcu ucuucagaag guu                                          23


<210> SEQ ID NO 583
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 583

aguuggugcu ucuucagaau u                                            21


<210> SEQ ID NO 584
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl,
      phosphorothioate linked ribonucleotides

<400> SEQUENCE: 584

aguuggugcu ucuucagaag guu                                          23
```

<210> SEQ ID NO 585
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 585
aguuggugcu ucuucagaag guu 23

<210> SEQ ID NO 586
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 586
ucaguuggug cuucuucagu u 21

<210> SEQ ID NO 587
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 587
acuguuuuca guuggugcuu u 21

<210> SEQ ID NO 588
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 588
acuguuuuca guuggugcuu cuu 23

<210> SEQ ID NO 589
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 589
uucugugcuu ggaaccgggu u 21

<210> SEQ ID NO 590
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 590
uagaaggagc cucugugcuu u 21

<210> SEQ ID NO 591
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 591
guggugcuug uucagaaggu u 21

<210> SEQ ID NO 592
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 592
auggugcuug uucagaaggu u 21

<210> SEQ ID NO 593
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 593
uaccugauuc uguuucugau u 21

<210> SEQ ID NO 594
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 594
ucuaggacac cugauucugu u 21

<210> SEQ ID NO 595
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 595
aagaaugugc cucgauaacu u 21

<210> SEQ ID NO 596
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 596
ggagaaugug ccucgauaau u 21

<210> SEQ ID NO 597
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 597
agagaaugug ccucgauaau u 21

<210> SEQ ID NO 598
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 598
uugugucuga gcaucgcguu u 21

<210> SEQ ID NO 599
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 599
uacagucccu ucugugucuu u 21

<210> SEQ ID NO 600
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 600
uuacaaugcu uccaggacau u 21

<210> SEQ ID NO 601
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 601
augcuuucca aaccuuguuu u 21

<210> SEQ ID NO 602
<211> LENGTH: 24
<212> TYPE: DNA
<213> ORGANISM: Artificial Sequence
<220> FEATURE:
<223> OTHER INFORMATION: synthetic unmodified polynucleotide

<400> SEQUENCE: 602
caaaatggaa cataaggaag tggt 24

<210> SEQ ID NO 603
<211> LENGTH: 19
<212> TYPE: DNA
<213> ORGANISM: Artificial Sequence
<220> FEATURE:
<223> OTHER INFORMATION: synthetic unmodified polynucleotide

<400> SEQUENCE: 603
gtgacagtgg tggagtacg 19

<210> SEQ ID NO 604
<211> LENGTH: 9

<212> TYPE: DNA
<213> ORGANISM: Artificial Sequence
<220> FEATURE:
<223> OTHER INFORMATION: synthetic unmodified polynucleotide

<400> SEQUENCE: 604 catggcttt 9

<210> SEQ ID NO 605
<211> LENGTH: 13
<212> TYPE: DNA
<213> ORGANISM: Artificial Sequence
<220> FEATURE:
<223> OTHER INFORMATION: synthetic unmodified polynucleotide

<400> SEQUENCE: 605
gctcaggtgc tgc 13

<210> SEQ ID NO 606
<211> LENGTH: 18
<212> TYPE: DNA
<213> ORGANISM: Artificial Sequence
<220> FEATURE:
<223> OTHER INFORMATION: synthetic unmodified polynucleotide

<400> SEQUENCE: 606
atgaccccca tcactcct 18

<210> SEQ ID NO 607
<211> LENGTH: 25
<212> TYPE: DNA
<213> ORGANISM: Artificial Sequence
<220> FEATURE:
<223> OTHER INFORMATION: synthetic unmodified polynucleotide

<400> SEQUENCE: 607
tcaagtttac aaccaagatt cactg 25

<210> SEQ ID NO 608
<211> LENGTH: 9
<212> TYPE: DNA
<213> ORGANISM: Artificial Sequence
<220> FEATURE:
<223> OTHER INFORMATION: synthetic unmodified polynucleotide

<400> SEQUENCE: 608 agctgcggt 9

<210> SEQ ID NO 609
<211> LENGTH: 15
<212> TYPE: DNA
<213> ORGANISM: Artificial Sequence
<220> FEATURE:
<223> OTHER INFORMATION: synthetic unmodified polynucleotide

<400> SEQUENCE: 609
acaatcccag aactc 15

<210> SEQ ID NO 610
<211> LENGTH: 20
<212> TYPE: RNA
<213> ORGANISM: Artificial Sequence
<220> FEATURE:
<223> OTHER INFORMATION: synthetic unmodified polynucleotide

<400> SEQUENCE: 610

```
cgcccuuggu guuacaccau                                                20


<210> SEQ ID NO 611
<211> LENGTH: 21
<212> TYPE: RNA
<213> ORGANISM: Artificial Sequence
<220> FEATURE:
<223> OTHER INFORMATION: synthetic unmodified polynucleotide

<400> SEQUENCE: 611

ugguguaaca ccaagggcga a                                              21


<210> SEQ ID NO 612
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 612

cgcccuuggu guuacaccau                                                20


<210> SEQ ID NO 613
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      abasic, phosphorothioate linked ribonucleotides

<400> SEQUENCE: 613

uucgcccuug guguuacacc                                                20


<210> SEQ ID NO 614
<211> LENGTH: 18
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(18)
<223> OTHER INFORMATION: combination of 2'-fluoro, 2'-O-methyl, inverted
      abasic, phosphorothioate linked ribonucleotides

<400> SEQUENCE: 614

cgcccuuggu guuacacc                                                  18
```

<210> SEQ ID NO 615
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 615
uucgcccuug guguuacacc 20

<210> SEQ ID NO 616
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted abasic, phosphorothioate linked ribonucleotides

<400> SEQUENCE: 616
uucgcccuug guguuacacc 20

<210> SEQ ID NO 617
<211> LENGTH: 23
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(23)
<223> OTHER INFORMATION: combination of 2'-fluoro, 2'-O-methyl, phosphorothioate linked ribonucleotides

<400> SEQUENCE: 617
ugguguaaca ccaagggcga auu 23

<210> SEQ ID NO 618
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl, phosphorothioate linked ribonucleotides

<400> SEQUENCE: 618
ugguguaaca ccaagggcgu u 21

<210> SEQ ID NO 619
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:

```
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 619

ugguguaaca ccaagggcga a                                              21


<210> SEQ ID NO 620
<211> LENGTH: 20
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(20)
<223> OTHER INFORMATION: combination of 2'-fluoro, 2'-O-methyl, inverted
      deoxyadenosine, phosphorothioate linked ribonucleotides

<400> SEQUENCE: 620

cagccccuua uuguuauacg                                                20


<210> SEQ ID NO 621
<211> LENGTH: 21
<212> TYPE: RNA
<213> ORGANISM: Artificial Sequence
<220> FEATURE:
<223> OTHER INFORMATION: synthetic modified polynucleotide
<220> FEATURE:
<221> NAME/KEY: modified_base
<222> LOCATION: (1)..(21)
<223> OTHER INFORMATION: combination of 2'-fluoro, 2'-O-methyl,
      phosphorothioate linked ribonucleotides

<400> SEQUENCE: 621

ucguauaaca auaaggggcu g                                              21
```